US008822160B2

(12) United States Patent
Bayley et al.

(10) Patent No.: US 8,822,160 B2
(45) Date of Patent: Sep. 2, 2014

(54) MOLECULAR ADAPTORS

(75) Inventors: John Hagan Bayley, Oxford (GB); Haichen Wu, Oxford (GB); Giovanni Maglia, Oxford (GB); Yann Astier, Oeiras (PT)

(73) Assignee: Isis Innovation Limited, Oxford (GB)

( * ) Notice: Subject to any disclaimer, the term of this patent is extended or adjusted under 35 U.S.C. 154(b) by 0 days.

(21) Appl. No.: 12/681,643

(22) PCT Filed: Oct. 6, 2008

(86) PCT No.: PCT/GB2008/003372
§ 371 (c)(1),
(2), (4) Date: Jun. 15, 2010

(87) PCT Pub. No.: WO2009/044170
PCT Pub. Date: Apr. 9, 2009

(65) Prior Publication Data
US 2010/0297638 A1    Nov. 25, 2010

(30) Foreign Application Priority Data

Oct. 5, 2007    (GB) .................................... 0719531.6

(51) Int. Cl.
*C12Q 1/68* (2006.01)
*G01N 27/00* (2006.01)
*C07K 14/00* (2006.01)
(52) U.S. Cl.
USPC ............... 435/6.19; 435/6; 435/6.1; 436/149; 530/350
(58) Field of Classification Search
None
See application file for complete search history.

(56) References Cited

U.S. PATENT DOCUMENTS

| | | | |
|---|---|---|---|
| 5,777,078 A | 7/1998 | Bayley et al. | |
| 5,795,782 A | 8/1998 | Church et al. | |
| 5,817,771 A | 10/1998 | Bayley et al. | |
| 6,015,714 A | 1/2000 | Baldarelli et al. | |
| 6,123,819 A | 9/2000 | Peeters | |
| 6,127,166 A | 10/2000 | Bayley et al. | |
| 6,251,610 B1 | 6/2001 | Gupte et al. | |
| 6,362,002 B1 | 3/2002 | Denison et al. | |
| 6,426,231 B1 | 7/2002 | Bayley et al. | |
| 6,451,563 B1 | 9/2002 | Wittig et al. | |
| 6,627,067 B1 | 9/2003 | Branton et al. | |
| 6,824,659 B2 | 11/2004 | Bayley et al. | |
| 6,863,833 B1 | 3/2005 | Bloom et al. | |
| 6,916,665 B2 * | 7/2005 | Bayley et al. | ................ 436/149 |
| 6,927,070 B1 | 8/2005 | Bayley et al. | |
| 7,087,729 B1 | 8/2006 | Prive | |
| 7,189,503 B2 | 3/2007 | Akeson et al. | |
| 8,105,846 B2 | 1/2012 | Bayley et al. | |
| 2002/0028458 A1 | 3/2002 | Lexow | |
| 2002/0094526 A1 | 7/2002 | Bayley et al. | |
| 2003/0044816 A1 | 3/2003 | Denison et al. | |
| 2003/0099951 A1 | 5/2003 | Akeson et al. | |
| 2003/0108902 A1 | 6/2003 | Abarzua | |
| 2003/0211502 A1 | 11/2003 | Sauer et al. | |
| 2003/0215881 A1 | 11/2003 | Bayley et al. | |
| 2004/0214177 A1 | 10/2004 | Bension | |
| 2005/0053961 A1 | 3/2005 | Akeson et al. | |
| 2005/0260655 A1 | 11/2005 | Liu et al. | |
| 2007/0015182 A1 | 1/2007 | Abarzua | |
| 2008/0311582 A1 | 12/2008 | Bayley et al. | |
| 2009/0298075 A1 | 12/2009 | Travers et al. | |
| 2011/0177498 A1 | 7/2011 | Clarke et al. | |
| 2011/0229877 A1 | 9/2011 | Jayasinghe et al. | |

FOREIGN PATENT DOCUMENTS

| | | |
|---|---|---|
| GB | 2130219 | 5/1984 |
| GB | 2453377 | 4/2009 |
| JP | 11-137260 | 5/1999 |
| WO | 99/05167 A1 | 2/1999 |
| WO | 00/28312 A1 | 5/2000 |
| WO | 01/40516 A2 | 6/2001 |
| WO | 01/42782 A1 | 6/2001 |
| WO | 01/59453 A2 | 8/2001 |
| WO | 02/42496 A2 | 5/2002 |
| WO | 03/095669 A1 | 11/2003 |
| WO | 2005/056750 A2 | 6/2005 |
| WO | 2006/020775 A2 | 2/2006 |
| WO | 2006/028508 A2 | 3/2006 |
| WO | 2006/100484 A2 | 9/2006 |
| WO | 2007/057668 A1 | 5/2007 |
| WO | 2007/075987 A2 | 7/2007 |
| WO | 2007/084103 A2 | 7/2007 |
| WO | 2008/045575 A2 | 4/2008 |
| WO | 2008/083554 A1 | 7/2008 |
| WO | 2008/102120 A1 | 8/2008 |

(Continued)

OTHER PUBLICATIONS

Howorka, Stefan et al., "DNA Duplex Formation of Individual DNA Strands within a Single Protein Pore," Biophysical Journal, vol. 82(1, pt. 2):508a, No. 2482-Plat (2002).
Howorka, Stefan et al., "Sequence-specific detection of individual DNA strands using engineered nanopores," Nature Biotechnology, vol. 19:636-639 (2001).
Movileanu, Llviu et al., "Detecting protein analytes that modulate transmembrane movement of a polymer chain within a single protein pore," Nature Biotechnology, vol. 18:1091-1095 (2001).
Xie, Hongzhi et al., "Single-Molecule Observation of the Catalytic Subunit of cAMP-Dependent Protein Kinase Binding to an Inhibitor Peptide," Chemistry & Biology, vol. 12:109-120 (2005).

(Continued)

*Primary Examiner* — Ruixiang Li
(74) *Attorney, Agent, or Firm* — Nelson Mullins Riley & Scarborough LLP; Jane E. Remillard, Esq.; Christopher L. Frank

(57) ABSTRACT

The invention relates to transmembrane protein pore for use in detecting a analyte in a sample. The pore comprises a molecular adaptor that facilitates an interaction between the pore and the analyte. The adaptor is covalently attached to the pore in an orientation that allows the analyte to be detected using the pore.

8 Claims, 13 Drawing Sheets

(56) References Cited

FOREIGN PATENT DOCUMENTS

| WO | 2008/102121 A1 | 8/2008 |
|---|---|---|
| WO | 2008/124107 A1 | 10/2008 |
| WO | 2010/004265 A1 | 1/2010 |
| WO | 2010/034018 A2 | 3/2010 |

OTHER PUBLICATIONS

International Preliminary Report on Patentability for Application No. PCT/GB2008/003372, dated Apr. 7, 2010.
Astier, Yann et al., "Toward Single Molecule DNA Sequencing: Direct Identification of Ribonucleoside and Deoxyribonucleoside 5'-Monophosphates by Using an Engineered Protein Nanopore Equipped with a Molecular Adapter," J. Am. Chem. Soc., vol. 128:1705-1710 (2006).
Bayley, Hagan, "Sequencing single molecules of DNA," Current Opinion in Chemical Biology, vol. 10:628-637 (2006).
Bayley, Hagan et al., "Stochastic sensors inspired by biology," Nature, vol. 413:226-230 (2001).
Braha, Orit et al., "Carriers versus Adapters in Stochastic Sensing," ChemPhysChem, vol. 6:889-892 (2005).
Braha, Orit et al., "Designed protein pores as components for biosensors," Chemistry & Biology, vol. 4:497-505 (1997).
Cheley, Stephen et al., "A functional protein pore with a 'retro' transmembrane domain," Protein Science, vol. 8:1257-1267 (1999).
Cheley, Stephen et al., "A Genetically Encoded Pore for the Stochastic Detection of a Protein Kinase," ChemBioChem, vol. 7:1923-1927 (2006).
Cheley, Stephen et al., "Stochastic Sensing of Nanomolar Inositol 1,4,5-Trisphosphate with an Engineered Pore," Chemistry & Biology, vol. 9:829-838 (2002).
Gu, Li-Qun et al., "Capture of a Single Molecule in a Nanocavity," Science, vol. 291:636-640 (2001).
Gu, Li-Qun et al., "Electroosmotic enhancement of the binding of a neutral molecule to a transmembrane pore," PNAS, vol. 100(26):15498-15503 (2003).
Gu, Li-Qun et al., "Reversal of charge selectivity in transmembrane protein pores by using noncovalent molecular adapters," PNAS, vol. 97(8):3959-3964 (2000).
Gu, Li-Qun et al., "Stochastic sensing of organic analytes by a pore-forming protein containing a molecular adapter," Nature, vol. 398:686-690 (1999).
Holden, Matthew A. et al., "Functional Bionetworks from Nanoliter Water Droplets," J. Am. Chem. Soc., vol. 129:8650-8655 (2007).
Hwang, William L. et al., "Electrical Behavior of Droplet Interface Bilayer Networks: Experimental Analysis and Modeling," J. Am. Chem. Soc., vol. 129:11854-11864 (2007).
Kang, Xiao-feng et al., "Single Protein Pores Containing Molecular Adapters at High Temperatures," Angew. Chem. Int. Ed., vol. 44:1495-1499 (2005).
Sanchez-Quesada, Jorge et al., "Cyclic Peptides as Molecular Adapters for a Pore-Forming Protein," Journal of the American Chemical Society, vol. 122(48):11757-11766 (2000).
Shin, Seong-Ho et al., "Kinetics of a Reversible Covalent-Bond-Forming Reaction Observed at the Single-Molecular Level," Angew. Chem. Int. Ed., vol. 41(19):3707-3709 (2002).
Notice of Allowance mailed Sep. 27, 2011, in co-pending U.S. Appl. No. 12/093,610.
Office Action mailed Apr. 4, 2011, in co-pending U.S. Appl. No. 12/093,610.
Office Action mailed Sep. 29, 2010, in co-pending U.S. Appl. No. 12/093,610.
Office Action mailed Jan. 22, 2010, in co-pending U.S. Appl. No. 12/093,610.
Office Action mailed Oct. 6, 2009, in co-pending U.S. Appl. No. 12/093,610.
Office Action mailed Dec. 21, 2012, in co-pending U.S. Appl. No. 13/002,709.
Office Action mailed Dec. 20, 2012, in co-pending U.S. Appl. No. 13/002,717.

Wang, Hui et al., "Nanopores with a spark for single-molecule detection," Nature Biotechnology, vol. 19:622-623 (2001).
Wang, Qian et al., "Bioconjugation by Copper(I)-Catalyzed Azide-Alkyne [3+2] Cycloaddition," J. Am. Chem. Soc., vol. 125:3192-3193 (2003).
Wanunu, Meni et al., "DNA Translocation Governed by Interactions with Solid-State Nanopores," Biophysical Journal, vol. 95:4716-4725 (2008).
Wemmer, David E. et al., "Preparation and melting of single strand circular DNA loops," Nucleic Acids Research, vol. 13(23):8611-8621 (1985).
Winters-Hilt, Stephen et al., "Highly Accurate Classification of Watson-Crick Basepairs on Termini of Single DNA Molecules," Biophysical Journal, vol. 84:967-976 (2003).
Wolfe, Aaron J. et al., "Catalyzing the Translocation of Polypeptides through Attractive Interactions," J. Am. Chem. Soc., vol. 129:14034-14041 (2007).
Wong, C.T.A. et al., "Polymer capture by electro-osmotic flow of oppositely charged nanopores," The Journal of Chemical Physics, vol. 126:164903-1-164903-6 (2007).
Wu, Hai-Chen et al., "Protein Nanopores with Covalently Attached Molecular Adapters," J. Am. Chem. Soc., vol. 129:16142-16148 (2007).
Yamagata, Atsushi et al., "Overexpression, purification and characterization of RecJ protein from *Thermus thermophilus* HB8 and its core domain," Nucleic Acids Research, vol. 29(22):4617-4624 (2001).
International Preliminary Report on Patentability and Written Opinion for Application No. PCT/GB2009/001679, 6 pages, dated Jan. 11, 2011.
International Preliminary Report on Patentability and Written Opinion for Appliction No. PCT/GB2009/001690, 9 pages, dated Jan. 11, 2011.
International Preliminary Report on Patentability for Application No. PCT/GB2006/004265, 7 pages, dated May 20, 2008.
International Search Report for Application No. PCT/GB2009/001679, 3 pages, dated Nov. 5, 2009.
International Search Report for Application No. PCT/GB2009/001690, 3 pages, dated Oct. 13, 2009.
U.S. Office Action for U.S. Appl. No. 13/338,794, filed Dec. 28, 2011, First Named Inventor Hagen Bayley, mailed Mar. 5, 2013.
U.S. Office Action for U.S. Appl. No. 13/338,794, filed Dec. 28, 2011, First Named Inventor Hagen Bayley, mailed Sep. 24, 2012.
U.S. Office Action for U.S. Appl. No. 13/338,794, filed Dec. 28, 2011, First Named Inventor Hagen Bayley, mailed Jul. 19, 2012.
U.S. Office Action for U.S. Appl. No. 13/129,278, filed Aug. 26, 2011, First Named Inventor Giovanni Maglia, mailed Feb. 27, 2013.
U.S. Office Action for U.S. Appl. No. 13/147,171, filed Nov. 10, 2011, First Named Inventor Ruth Moysey, mailed May 6, 2013.
U.S. Office Action for U.S. Appl. No. 13/147,171, filed Nov. 10, 2011, First Named Inventor Ruth Moysey, mailed Jan. 3, 2013.
U.S. Office Action for U.S. Appl. No. 13/147,159, filed Nov. 15, 2011, First Named Inventor Brian McKeown, mailed May 28, 2013.
U.S. Office Action for U.S. Appl. No. 13/147,159, filed Nov. 15, 2011, First Named Inventor Brian McKeown, mailed Jan. 25, 2013.
U.S. Office Action for U.S. Appl. No. 13/260,178, filed Jan. 17, 2012, First Named Inventor David Stoddart, mailed May 9, 2013.
U.S. Office Action for U.S. Appl. No. 13/260,178, filed Jan. 17, 2012, First Named Inventor David Stoddart, mailed Feb. 20, 2013.
U.S. Office Action for U.S. Appl. No. 13/002,709, filed May 13, 2012, First Named Inventor Lakmal Jayasinghe, mailed Jun. 27, 2013.
U.S. Office Action for U.S. Appl. No. 13/002,709, filed May 13, 2012, First Named Inventor Lakmal Jayasinghe, mailed Dec. 21, 2012.
Akeson, Mark et al., "Microsecond Time-Scale Discrimination Among Polycytidylic Acid, Polyadenylic Acid, and Polyuridylic Acid as Homopolymers or as Segments Within Single RNA Molecules," Biophysical Journal, vol. 77:3227-3233 (1999).
Amblard, Franck et al., "The Cu(I)-catalyzed Huisgen azide-alkyne 1,3-dipolar cycloaddition reaction in nucleotide and oligonucleotide chemistry," Chem. Rev., vol. 109(9):4207-4220 (2009).

(56) References Cited

OTHER PUBLICATIONS

Ashkenasy, Nurit et al., "Recognizing a Single Base in an Individual DNA Strand: A Step Toward DNA Sequencing in Nanopores," Angew. Chem. Int. Ed., vol. 44:1401-1404 (2005).

Ashkenasy, Nurit et al., "Single Nucleobase Sensitivity of a-Hemolysin (a-HL) Transmembrane Protein Pore: Toward Single DNA Sequencing," ACS National Meeting, vol. 45(13), Abstract No. 74 (2005).

Astier, Yann et al., "Stochastic Detection of Motor Protein-RNA Complexes by Single-Channel Current Recording," ChemPhysChem, vol. 8:2189-2194 (2007).

Benner, Seico et al., "Sequence-specific detection of individual DNA polymerase complexes in real time using a nanopore," Nature Nanotechnology, vol. 2:718-724 (2007).

Branton, Daniel et al., "The potential and challenges of nanopore sequencing," Nat. Biotechnol., vol. 26 (10):1146-1153 (2008).

Braslavsky, Ido et al., "Sequence information can be obtained from single DNA molecules," PNAS, vol. 100 (7):3960-3964 (2003).

Budanova, Natalia et al., "Heptakis(6-amino-6-deoxy)-beta-cyclodextrin as a chiral selector for the separation of anionic analyte enantiomers by capillary electrophoresis," Electrophoresis, vol. 25:2795-2800 (2004).

Busam, Robert D., "Structure of *Escherichia coli* exonuclease I in complex with thymidine 5'-monophosphate," Acta Cryst., vol. D64:206-210 (2008).

Butler, Tom Z. et al., "Determination of RNA Orientation during Translocation through a Biological Nanopore," Biophysical Journal, vol. 90:190-199 (2006).

Butler, Tom Z. et al., "Single-molecule DNA detection with an engineered MspA protein nanopore," PNAS, vol. 105 (52):20647-20652 (2008).

Chan, Eugene Y., "Advances in sequencing technology," Mutation Research, vol. 573:13-40 (2005).

Cheley, Stephen et al., "Spontaneous oligomerization of a staphylococcal alpha-hemolysin conformationally constrained by removal of residues that form the transmembrane beta-barrel," Protein Engineering, vol. 10 (12):1433-1443 (1997).

Chen, Min et al., "Outer membrane protein G: Engineering a quiet pore for biosensing," PNAS, vol. 105 (17):6272-6277 (2008).

Chen, Peng et al., "Atomic Layer Deposition to Fine-Tune the Surface Properties and Diameters of Fabricated Nanopores," Nano Letters, vol. 4(7):1333-1337 (2004).

Clarke, James et al., "Continuous base identification for single-molecule nanopore DNA sequencing," Nature Nanotechnology, vol. 4:265-270 (2009).

Cockroft, Scott L. et al., "A Single-Molecule Nanopore Device Detects DNA Polymerase Activity with Single-Nucleotide Resolution," J.Am. Chem. Soc., vol. 130:818-820 (2008).

Comai, Massimiliano et al., "Protein engineering modulates the transport properties and ion selectivity of the pores formed by stapylcoccal y-haemolysins in lipid membranes," Molecular Mirobiology, vol. 44(5):1251-1267 (2002).

Cudic, Predrag et al., "Binding of Nucleotides in Water by Phenathridinium Bis(intercaland) Receptor Molecules," J. Chem. Soc., Chem. Commun., pp. 1073-1075 (1995).

Dapprich, Johannes, "Single-Molecule DNA Digestion by Lambda-Exonuclease," Cytometry, vol. 36:163-168 (1999).

Deamer, David W. et al., "Characterization of Nucleic Acids by Nanopore Analysis," Ac. Chem. Res., vol. 35:817-825 (2002).

Deamer, David W. et al., "Nanopores and nucleic acids: prospects for ultrarapid sequencing," TIBTECH, vol. 18:147-151 (2000).

Dorre, Klaus et al., "Techniques for single molecule sequencing," Bioimaging, vol. 5:139-152 (1997).

Eid, John et al., "Real-Time DNA Sequencing from Single Polymerase Molecules," Science, vol. 323:133-138 (2009).

Eliseev, Alexey V. et al., "Aminocyclodextrins as Selective Hosts with Several Binding Sites for Nucleotides," Angew. Chem. Int. Ed. Engl., vol. 32(9):1331-1333 (1993).

Eliseev, Alexey V. et al., "Molecular Recognition of Nucleotides, Nucleosides, and Sugars by Aminocyclodextrins," J. Am. Chem. Soc., vol. 116:6081-6088 (1994).

Erie, Dorothy et al., "A Dumbell-Shaped, Double-Hairpin Structure of DNA: A Thermodynamic Investigation," Biochemistry, vol. 26:7150-7159 (1987).

Flomembom, O. et al., Single stranded DNA translocation through a nanopore: A master equation approach, Physical Review E, vol. 68:041910, DOI: 10.1103/PhysRevE.68.041910, 7 pages, (2003).

Flusberg, Benjamin A. et al., "Direct detection of DNA methylation during single-molecule, real-time sequencing," Nature Methods, vol. 7(6):461-465 (2010).

Genschel, Jochen et al., "Interaction of *E. coli* Single-Stranded DNA Binding Protein (SSB) with Exonuclease I. The Carboxy-Terminus of SSB Is the Recognition Site fo the Nuclease," Biol. Chem., vol. 381:183-192 (2000).

Gershow, Marc et al., "Recapturing and trapping single molecules with a solid-state nanopore," Nature Nanotechnology, vol. 2:775-779 (2007).

Ghosal, Sandip, "Electrokinetic-flow-induced viscous drag on a tethered DNA inside a nanopore," Physical Review E, vol. 76:061916, DOI: 10.1103/PhysRevE.76.061916, 3 pages, (2007).

Gu, Li-Qun et al., "Prolonged Residence Time of a Noncovalent Molecular Adapter, beta-Cyclodextrin, within the Lumen of Mutant alpha-Hemolysin Pores," J. Gen. Physiol., vol. 118:481-493 (2001).

Guan, Xiyun et al., "Stochastic Sensing of TNT with a Genetically Engineered Pore," ChemBioChem, vol. 6:1875-1881 (2005).

Han, Eugene S. et al., "RecJ exonuclease: substrates, products and interaction with SSB," Nucleic Acids Research, vol. 34(4):1084-1091 (2006).

Han, Jongyoon et al., "Characterization and Optimization of an Entropic Trap for DNA Separation," Anal. Chem., vol. 74:394-401 (2002).

Hein, Christopher D. et al., "Click Chemistry, a Powerful Tool for Pharmaceutical Sciences," Pharm. Res., vol. 25 (10):2216-2230 (2008).

Henrickson, Sarah E. et al., "Driven DNA Transport into an Asymmetric Nanometer-Scale Pore," Physical Review Letters, vol. 85(14):3057-3060 (2000).

Holden, Matthew A. et al., "Direct Introduction of Single Protein Channels and Pores into Lipid Bilayers," J. Am. Chem. Soc., vol. 127:6502-6503 (2005).

Hornblower, Breton et al., "Single-molecule analysis of DNA-protein complexes using nanopores," Nature Methods, vol. 4(4):315-317 (2007).

Howarka, Stefan et al., "Probing Distance and Electrical Potential within a Protein Pore with Tethered DNA," Biophysical Journal, vol. 83:3202-3210 (2002).

Howorka, S. et al., "Improved Protocol for High-Throughput Cysteine Scanning Mutagenesis," Biotechniques, vol. 25(5):764-766 (1998).

Howorka, Stefan et al., "Kinetics of duplex formation for individual DNA strands within a single protein nanopore," PNAS, vol. 98(23):12996-13001 (2001).

Hu, Tao et al., "Theory of DNA translocation through narrow ion channels and nanopores with charged walls," Physical Review E, vol. 78:032901, DOI: 10.1103/PhysRevE.78.032901, 3 pages, (2008).

Jayasinghe, Lakmal et al., "The leukocidin pore: Evidence for an octamer with four LukF subunits and four LukS subunits alternating around a central axis," Protein Science, vol. 14:2550-2561 (2005).

Jung, Yuni et al., "The Internal Cavity of the Staphylococcal alpha-Hemolysin Pore Accommodates~ Exogenous Amino Acid Residues," Biochemistry, vol. 44(25):8919-8929 (2005).

Kalisch, Bernd W. et al., "Covalently linked sequencing primer linkers (splinkers) for sequence analysis of restriction fragments (Recombinant DNA; hairpin ligation; synthetic oligodeoxynucleotides; dideoxynucleotides)," Gene, vol. 44:263-270 (1986).

Kasianowicz, John J. et al., "Characterization of individual polynucleotide molecules using a membrane channel," Proc. Natl. Acad. Sci. USA, vol. 93:13770-13773 (1996).

(56) References Cited

OTHER PUBLICATIONS

Khulbe, Pramod K. et al., "DNA translocation through a-hemolysin nanopores with potential application to macromolecular data storage," Journal of Applied Physics, vol. 97(104317):1-7 (2005).
Kocalka, Petr et al., "Rapid and Efficient DNA Strand Cross-Linking by Click Chemistry," ChemBioChem, vol. 9:1280-1285 (2008).
Kolb, Hartmuth C. et al., "Click Chemistry: Diverse Chemical Function from a Few Good Reactions," Angew. Chem. Int. Ed., vol. 40:2004-2021 (2001).
Kovall, Rhett et al., "Toroidal Structure of Lambda-Exonuclease," Science, vol. 277:1824-1827 (1997).
Li, Jiali et al., "DNA molecules and configurations in a solid-state nanopore microscope," Nature, vol. 2:611-615 (2003).
Lovett, Susan T. et al., "Identification and purification of a single-stranded-DNA-specific exonuclease encoded by the recJ gene of *Escherichia coli*," Proc. Natl. Acad. Sci. USA, vol. 86:2627-2631 (1989).
Lovrinovic, Marina et al., "Rapid synthesis of DNA-cysteine conjugates for expressed protein ligation," Biochemical and Biophysical Research Communications, vol. 335:943-948 (2005).
Luo, Kaifu et al., "Influence of Polymer-Pore Interactions on Translocation," Physical Review Letters, vol. 99:148102, DOI: 10.1103/PhysRev Lett. 99:148102, 4 pages, (2007).
Lutz, Jean-Francois et al., "Efficient construction of therapeutics, bioconjugates, biomaterials and bioactive surfaces using azide-alkyne 'click' chemistry," Advanced Drug Delivery Reviews, vol. 60:958-970 (2008).
Maglia, Giovanni et al., "Enhanced translocation of single DNA molecules through alpha-hemolysin nanopores by manipulation of internal charge," PNAS, vol. 105(50):19720-19725 (2008).
Martin, Hugh et al., "Nanoscale Protein Pores Modified with PAMAM Dendrimers," J. Am. Chem. Soc., vol. 129:9640-9649 (2007).
Martínez, Javier et al., "The mRNA Cap Structure Stimulates Rate of Poly(A) Removal and Amplifies Processivity of Degradation," The Journal of Biological Chemistry, vol. 276(30):27923-27929 (2001).
Marziali, Andre et al., "New DNA Sequencing Methods," Annu. Rev. Biomed. Eng., vol. 3:195-223 (2001).
Mathé, Jérôme et al., "Orientation discrimination of a single-stranded DNA inside the a-hemolysin membrane channel," PNAS, vol. 102(35):12377-12382 (2005).
Matsuura, Shun-ichi et al., "Real-time observation of a single DNA digestion by I exonuclease under a fluorescence microscope field," Nucleic Acids Research, vol. 29(16):1-5 (2001).
Meller, Amit et al., "Rapid nanopore discrimination between single polynucleotide molecules," PNAS, vol. 97 (3):1079-1084 (2000).
Meller, Amit et al., "Single molecule measurements of DNA transport through a nanopore," Electrophoresis, vol. 23: 2583-2591 (2002).
Meller, Amit, "Dynamics of polynucleotide transport through nanometre-scale pores," Journal of Physics: Condensed Matter, vol. 15:R581-R607 (2003).
Merzlyak, Petr G. et al., "Conductance and Ion Selectivity of a Mesoscopic Protein Nanopore Probed with Cysteine Scanning Mutagenesis," Biophysical Journal, vol. 89:3059-3070 (2005).
Mitchell, Nick et al., "Chemical Tags Facilitate the Sensing of Individual DNA Strands with Nanopores," Angew. Chem. Int. Ed., vol. 47:5565-5568 (2008).
Mohammad, Mohammad M. et al., "Controlling a Single Protein in a Nanopore through Electrostatic Traps," J. Am. Chem. Soc., vol. 130:4081-4088 (2008).
Mol, Clifford D. et al., "Structure and function of the multifunctional DNA-repair enzyme exonuclease III," Nature, vol. 374:381-386 (1995).
Movileanu, Liviu et al., "Location of a Construction in the Lumen of a Transmembrane Pore by Targeted Covalent Attachment of Polymer Molecules," J. Gen. Physiol., vol. 117:239-251 (2001).
Muller, Joachim et al., "DNA-directed assembly of artificial multienzyme complexes," Biochemical and Biophysical Research Communications, vol. 377:62-67 (2008).

Nakane, Jonathan et al., "A Nanosensor for Transmembrane Capture and Identification of Single Nucleic Acid Molecules," Biophysical Journal, vol. 87:615-621 (2004).
Nakane, Jonathan J. et al., "Nanopore sensors for nucleic acid analysis," J. Phys.: Condens. Matter, vol. 15:R1365-R1393 (2003).
Niemeyer, Christof M. et al., "DNA-Directed Assembly of Bienzymic Complexes from In Vivo Biotinylated NAD(P)H: FMN Oxidoreductase and Luciferase," ChemBioChem., vol. 3:242-245 (2002).
Nwe, Kido et al., "Growing Applications of 'Click Chemistry' for Bioconjugation in Comtemporary Biomedical Research," Cancer Biotherapy and Radiopharmaceuticals, vol. 24(3):289-302 (2009).
Paner, Teodoro M. et al., "Studies of DNA Dumbells. III. Theoretical Analysis of Optical Melting Curves of Dumbells with a 16 Base-Pair Duplex Stem and Tn End Loops (n=2, 3, 4, 5, 6, 8, 10, 14)," Biopolymers, vol. 32(7):881-892 (1992).
Paner, Teodoro M. et al., "Studies of DNA Dumbells. VI. Analysis of Optical Melting Curves of Dumbells with a Sixteen-Base Pair Duplex Stem and End-Loops of Variable Size and Sequence," Biopolymers, vol. 39:779-793 (1996).
Phoenix, David A. et al., "OmpF-LPP Signal Sequence Mutants with Varying Charge Hydrophobicity Ratios Provide Evidence for a Phosphatidylglycerol-Signal Sequence Interaction during Protein Translocation across the *Escherichia coli* Inner Membrane," The Journal of Biological Chemistry, vol. 268(23):17069-17073 (1993).
Purnell, Robert F. et al., "Nucleotide Identificaiton and Orientation Discrimination of DNA Homopolymers Immobilized in a Protein Nanopore," Nano Letters, vol. 8(9):3029-3034 (2008).
Sanchez-Quesada, Jorge et al., "Single DNA Rotaxanes of a Transmembrane Pore Protein," Angew. Chem. Int. Ed., vol. 43:3063-3067 (2004).
Sanderson, Katherine, "Standard and Pores. Could the next generation of genetic sequencing machines be built froma collection of miniscule holes?" Nature News, vol. 456(7218):23-25 (2008).
Sauer-Budge, Alexis F. et al., "Unzipping Kinetics of Double-Stranded DNA in a Nanopore," Phys. Rev. Letters, vol. 90(23):238101-1-238101-4 (2003).
Seeman, Nadrian C., "Nucleic Acid Junctions and Lattices," J. theor. Biol., vol. 99:237-247 (1982).
Seo, Tae Seok et al., "Click Chemistry to Construct Fluorescent Oligonucleotides for DNA Sequencing," J. Org. Chem., vol. 68:609-612 (2003).
Seol, Yeonee, Stretching of Homopolymeric RNA Reveals Single-Stranded Helices and Base-Stacking, Physical Review Letters, vol. 98:158103, DOI: 10.1103/PhysRevLett.98.158103, 4 pages, (2007).
Shank, Lalida P. et al., "Redesigning Channel-Forming Peptides: Amino Acid Substitutions that Enhance Rates of Supramolecular Self-Assembly and Raise Ion Transport Activity," Biophysical Journal, vol. 90:2138-2150 (2006).
Smeets, Ralph M.M. et al., "Salt Dependence of Ion Transport and DNA Translocation through Solid-State Nanopores," Nano Letters, vol. 6(1):89-95 (2006).
Song, Langzhou et al., "Structure of Staphylococcal alpha-Hemolysin, a Heptameric Transmembrane Pore," Science, vol. 274:1859-1866 (1996).
Stoddart, David et al., "Multiple base-recognition sites in a biological nanopore—two heads are better than one," Angew. Chem. Int. Ed. Engl., vol. 49(3):556-559 (2010).
Stoddart, David et al., "Single-nucleotide discrimination in immobilized DNA oligonucleotides with a biological nanopore," PNAS, vol. 106(19):7702-7707 (2009).
Sutherland, Todd C. et al., "An analysis of mismatched duplex DNA unzipping through a bacterial nanopore," Biochem. Cell Biol., vol. 82:407-412 (2004).
Tadey, Tanya et al., "Capillary electrophoretic separation of nucleotide isomers via complexation with cyclodextrin and borate," Journal of Chromatography B, vol. 657:365-372 (1994).
Thomas, Kirk R. et al., "Processivity of DNA Exonucleases," The Journal of Biological Chemistry, vol. 253(2):424-429 (1978).
Tohda, Koji et al., "Channel Mimetic Sensing Membranes for Nucleotides Based on Multitopic Hydrogen Bonding," Israel Journal of Chemistry, vol. 37:267-275 (1997).

(56) References Cited

OTHER PUBLICATIONS

Travers, Kevin J. et al., "A flexible and efficient template format for circular consensus sequencing and SNP detection," Nucleic Acids Research, vol. 38(15):e159, doi:10.1093/nar/gkq543 (2010).

Tung, Ching-Hsuan, "Preparation and Applications of Peptide-Oligonucleotide Conjugates," Bioconjugate Chemistry, vol. 11(5):605-618 (2000).

Van De Goor, Tom A., "Nanopore Detection: Threading DNA Through a Tiny Hole," PharmaGenomics, vol. 4 (3):28-30 (2004).

Walker, Barbara et al., "Key Residues for Membrane Binding, Oligomerization and Pore Forming Activity of Staphylococcal alpha-Hemolysin Identified by Cysteine Scanning Mutagenesis and Targeted Chemical Modification," The Journal of Biological Chemistry, vol. 270 (39):23065-23071 (1995).

* cited by examiner

*cis*

*trans*

*cis*

*trans*

Figure 12

```
AATACTACAGTAAAAACAGGTGATTTAGTCACTTATGATAAAGAAAAATGGCATGCACAAAAAAAGTATTTTATAGTTTTATCGATGATAA
AAATCACAATAAAAAACTGCTAGTTATTAGAACAAAAGGTACCATTGCTGGTCAATATAGAGTTTATAGCGAAGAAGGTGCTAACAAAA
GTGGTTTAGCCTGGCCTTCAGCCTTTAAGGTACAGTTGCAACTACCTGATAATGAAGTAGCTCAAATATCGATTACTATCCCGGAAT
TCGATTGATACAAAGAGTATATGAGTACGTTAACGTTACGGTGTTACTGGTGATGATACAAAAATTGGAGGCCT
TATTGGTGCAAATGTTTTCGATTGGTCAATACACTTAAGTATGTTCAAACAATTCTCGAGAGCCCAACTGATAAAAAG
TAGGCTGGAAAGTGATATTTAACAATATGGTTCAAAATTGGGACCATACGATCGAGATTCTTGGAACCCGGTATATGGCAATCAA
CTTTTCATGAAAACTAGAAATGGTTCTATGTTATTACTATGGTTATTACAAAGCAGATAGAAAAGCATCCAAACAAATATAGATGTAATATACGAACGAGTTCGTG
TTCACCAGACTTCGCTACAGTTATTACTATGGAAAATTGGAAAGTTACCAATACTAAAGATAAATGGACAGATCGTTCTTCAGAAAGATATAAA
ATGAATTACCAATTGCATTGGACTTCAACAAATGACAAAT[T]GATGACGATGACGACGATGATTGA
```

MOLECULAR ADAPTORS

STATEMENT OF FEDERALLY SPONSORED RESEARCH

This invention was made with government support under Grant No. R01 GM051987 awarded by National Institutes of Health (NIH). The government has certain rights in this invention.

RELATED APPLICATIONS

This application is a 35 U.S.C. 371 national stage filing of International Application No. PCT/GB2008/003372 filed Oct. 6, 2008, which claims priority to GB Patent Application No. 0719531.6 filed on Oct. 5, 2007. The contents of the aforementioned applications are hereby incorporated by reference.

FIELD OF THE INVENTION

The invention relates to transmembrane protein pores that are useful for detecting analytes by stochastic sensing. A molecular adaptor is covalently attached to the pore in an orientation that allows detection of the analyte.

BACKGROUND OF THE INVENTION

Stochastic detection is an approach to sensing that relies on the observation of individual binding events between analyte molecules and a receptor. Stochastic sensors can be created by placing a single pore of nanometer dimensions in an insulating membrane and measuring voltage-driven ionic transport through the pore in the presence of analyte molecules. The frequency of occurrence of fluctuations in the current reveals the concentration of an analyte that binds within the pore. The identity of an analyte is revealed through its distinctive current signature, notably the duration and extent of current block (Braha, O., Walker, B., Cheley, S., Kasianowicz, J. J., Song, L., Gouaux, J. E., and Bayley, H. (1997) *Chem. Biol.* 4, 497-505; and Bayley, H., and Cremer, P. S. (2001) *Nature* 413, 226-230).

Engineered versions of the bacterial pore-forming toxin α-hemolysin (αHL) have been used for stochastic sensing of many classes of molecules (Bayley, H., and Cremer, P. S. (2001) *Nature* 413, 226-230; Shin, S.-H., Luchian, T., Cheley, S., Braha, O., and Bayley, H. (2002) *Angew. Chem. Int. Ed.* 41, 3707-3709; and Guan, X., Gu, L.-Q., Cheley, S., Braha, O., and Bayley, H. (2005) *ChemBioChem* 6, 1875-1881). In the course of these studies, it was found that attempts to engineer αHL to bind small organic analytes directly can prove taxing, with rare examples of success (Guan, X., Gu, L.-Q., Cheley, S., Braha, O., and Bayley, H. (2005) *ChemBioChem* 6, 1875-1881). Fortunately, a different strategy was discovered, which utilized non-covalently attached molecular adaptors, notably cyclodextrins (Gu, L.-Q., Braha, O., Conlan, S., Cheley, S., and Bayley, H. (1999) *Nature* 398, 686-690), but also cyclic peptides (Sanchez-Quesada, J., Ghadiri, M. R., Bayley, H., and Braha, O. (2000) *J. Am. Chem. Soc.* 122, 11758-11766) and cucurbiturils (Braha, O., Webb, J., Gu, L.-Q., Kim, K., and Bayley, H. (2005) *ChemPhysChem* 6, 889-892). Cyclodextrins become transiently lodged in the αHL pore and produce a substantial but incomplete channel block. Organic analytes, which bind within the hydrophobic interiors of cyclodextrins, augment this block allowing analyte detection (Gu, L.-Q., Braha, O., Conlan, S., Cheley, S., and Bayley, H. (1999) *Nature* 398, 686-690).

SUMMARY OF THE INVENTION

The inventors have surprisingly demonstrated that a molecular adaptor can be covalently attached to a transmembrane protein pore in a specific orientation. The inventors have also surprisingly demonstrated that a molecular adaptor can be covalently attached to a transmembrane pore in an orientation that allows an analyte to affect the current flowing through the pore in a manner specific for that analyte. A molecular adaptor can therefore be covalently attached to the pore in an orientation that allows the pore to be used to detect the analyte via stochastic sensing. The pore is preferably modified to facilitate the orientation of the molecular adaptor.

The fixed nature of the molecular adaptor means that a distinctive current flows through the pore whenever the analyte interacts with the pore. As a result, the transmembrane protein pores of the invention are useful tools for stochastic sensing, especially for detecting nucleotides or sequencing nucleic acids.

Accordingly, the invention provides a transmembrane protein pore for use in detecting an analyte in a sample, which comprises a molecular adaptor that facilitates an interaction between the pore and the analyte, wherein the adaptor is covalently attached to the pore in an orientation that allows the analyte to be detected using the pore.

The invention also provides:

a method of producing a transmembrane protein pore of the invention, comprising:
  (a) covalently attaching to a transmembrane protein pore a molecular adaptor that facilitates an interaction between the pore and an analyte; and
  (b) determining whether or not the adaptor is attached to the pore in an orientation that allows the analyte to be detected using the pore;

a method of determining presence or absence of an analyte, comprising:
  (a) contacting the analyte with a transmembrane protein pore of the invention so that the analyte interacts with the pore; and
  (b) measuring the current passing through the pore during the interaction and thereby determining the presence or absence of the analyte;

a method of identifying an individual nucleotide, comprising:
  (a) contacting the nucleotide with a transmembrane protein pore of the invention so that the nucleotide interacts with the pore; and
  (b) measuring the current passing through the pore during the interaction and thereby determining the identity of the nucleotide;

a method of sequencing a target nucleic acid sequence, comprising:
  (a) digesting an individual nucleotide from one end of the target sequence using a processive exonuclease;
  (b) contacting the nucleotide with a transmembrane protein pore of the invention so that the nucleotide interacts with the adaptor;
  (c) measuring the current passing through the pore during the interaction and thereby determining the identity of the nucleotide; and
  (d) repeating steps (a) to (c) at the same end of the nucleic acid sequence and thereby determining the sequence of the nucleic acid; and a kit for sequencing a nucleic acid, comprising a transmembrane protein pore according to the invention and a processive exonuclease.

τ$_{off}$=0.68±0.12 s. Level 1: (M113F-RL2)$_7$; level 2: (M113F-RL2)$_7$•βCD; level 3: spontaneous gating of the pore complex (M113F-RL2)$_7$•βCD.

Figure 10:
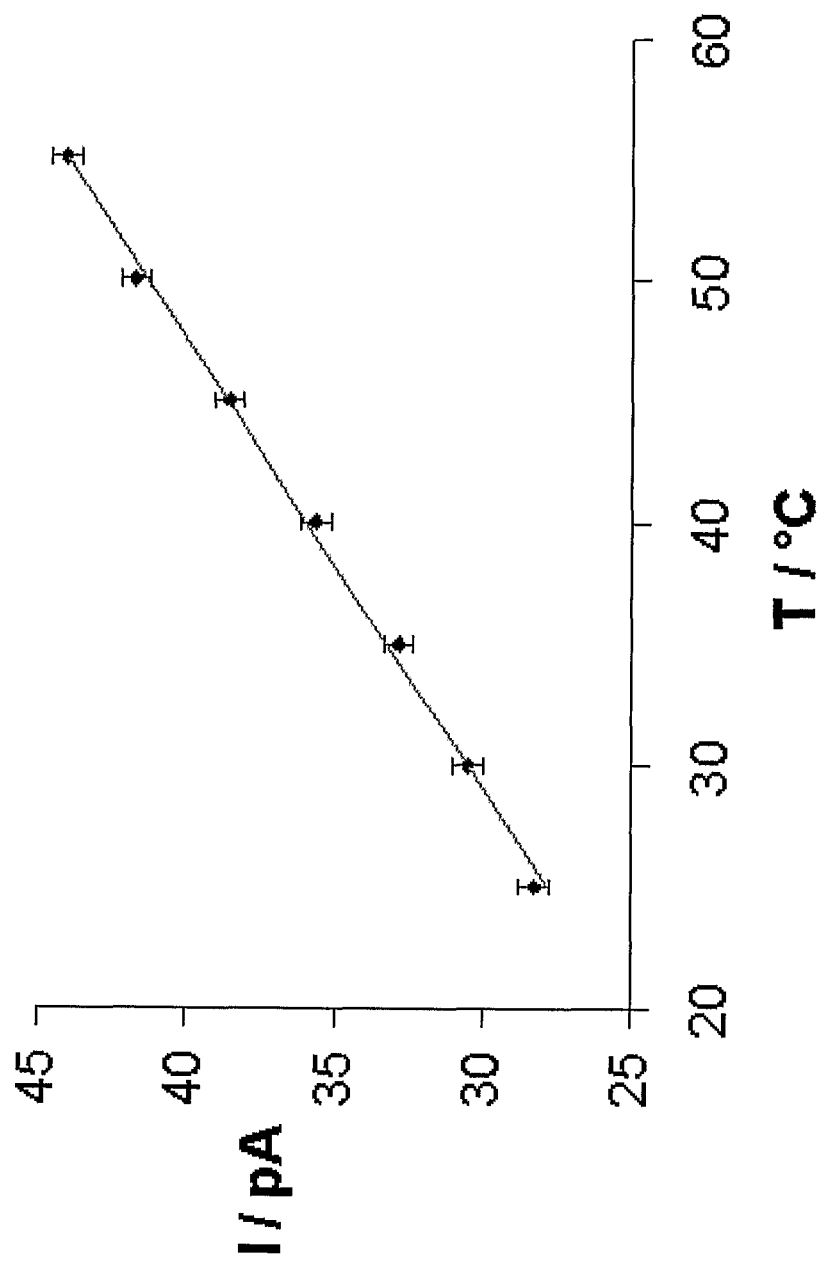

FIG. 10 shows the variation of the single-channel current with temperature for (M113F-RL2)$_6$(M113C-D8RL2)$_1$-βCD in 25 mM Tris.HCl, pH 8.0, 1 M KCl at +100 mV. The values shown in the plot are the average values for three different experiments. The single-channel currents depend linearly on the temperature. I (pA)=14.307+0.5402T(° C.).

Figure 11A:
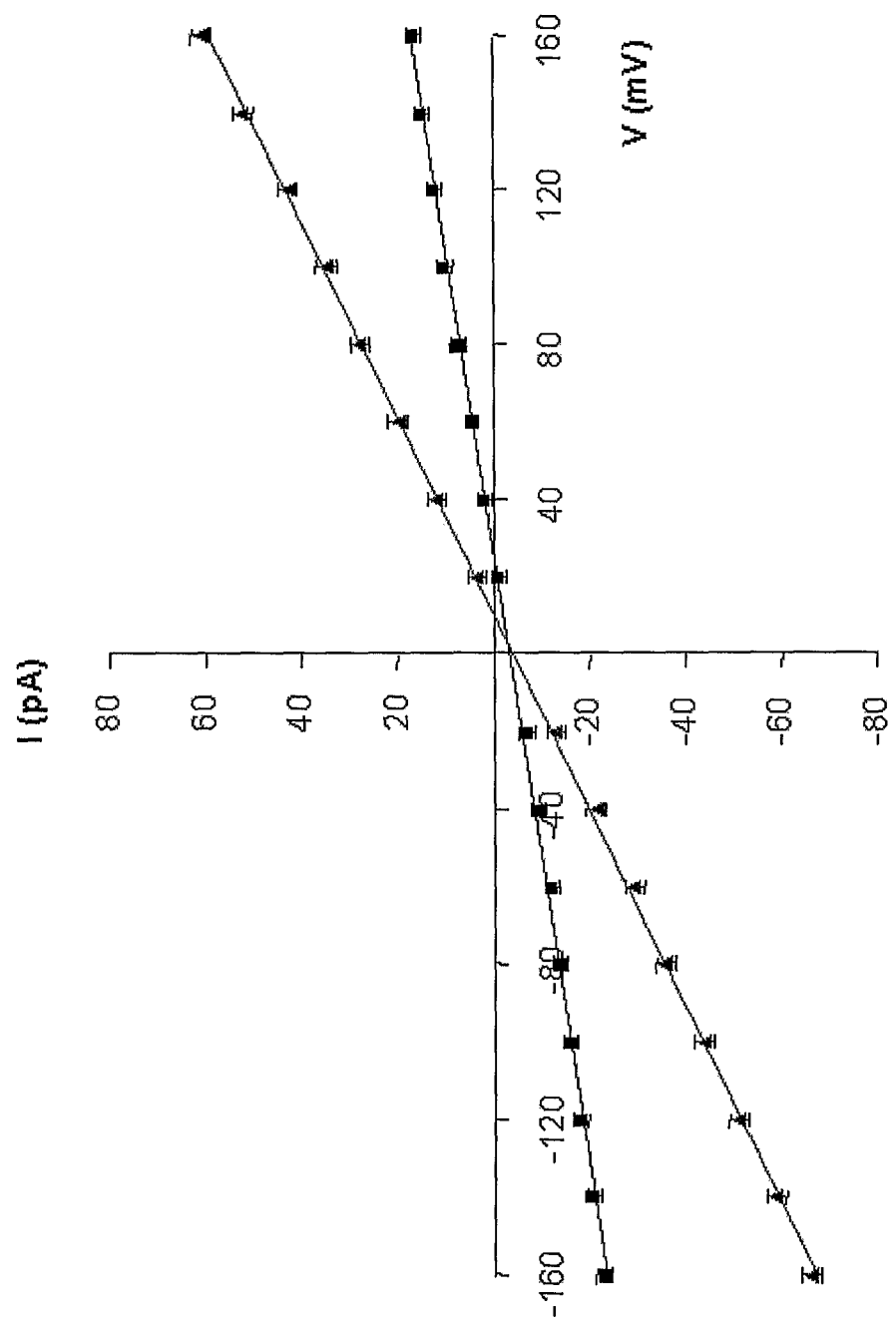
Figure 11B:
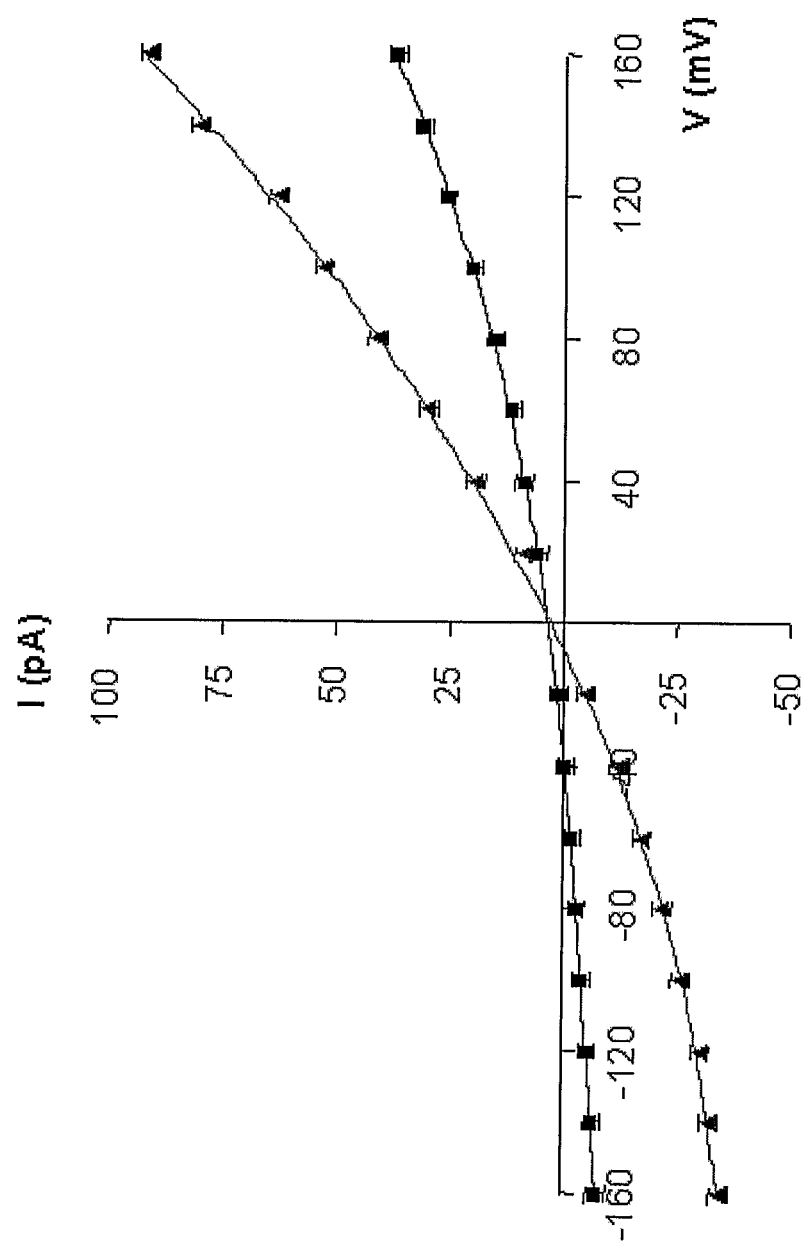

FIG. 11 shows the ion selectivity of (M113F-RL2)$_6$(M113C-D8RL2)$_1$-βCD and (M113N)$_6$(T117C-D8RL3)$_1$-βCD. a) I-V curves for (M113F-RL2)$_6$(M113C-D8RL2)$_1$ ( ) and (M113F-RL2)$_6$(M113C-D8RL2)$_1$-βCD (□) based on recordings made in 25 mM Tris.HCl, pH 8.0 with cis: 200 mM KCl; trans: 1000 mM KCl (n 3). Reversal potentials (Vr) are marked by arrows. b) I-V curves for (M113F-RL2)$_6$(M113C-D8RL2)$_1$ ( ) and (M113F-RL2)$_6$(M113C-D8RL2)-1-βCD (□) based on recordings made in 25 mM Tris.HCl, pH 8.0 with cis: 1000 mM KCl; trans: 200 mM KCl (n=3). Reversal potentials (Vr) are marked by arrows.

FIG. 12 shows the sequence encoding αHL-D8RL3 (including the octa-aspartate tail). This sequence is shown in SEQ ID NO: 18. The sequence encoding αHL-D8RL3 (SEQ ID NO: 18) is identical to nucleotides 13 to 918 of SEQ ID NO: 15, which encode T117C-D8RL3 used in the Example, except that SEQ ID NO: 15 has TGC (rather than ACG) at residues 361 to 363.

DESCRIPTION OF THE SEQUENCES

SEQ ID NO: 1 shows the polynucleotide sequence that encodes one subunit of wild-type α-hemolysin.

SEQ ID NO: 2 shows the amino acid sequence of one subunit of wild-type α-hemolysin.

SEQ ID NO: 3 shows the polynucleotide sequence that encodes one subunit of α-hemolysin M113H-RL2.

SEQ ID NO: 4 shows the amino acid sequence of one subunit of α-hemolysin M113H-RL2.

SEQ ID NO: 5 shows the polynucleotide sequence that encodes one subunit of α-hemolysin M113K-RL2.

SEQ ID NO: 6 shows the amino acid sequence of one subunit of α-hemolysin M113K-RL2.

SEQ ID NO: 7 shows the polynucleotide sequence that encodes one subunit of α-hemolysin M113R-RL2.

SEQ ID NO: 8 shows the amino acid sequence of one subunit of α-hemolysin M113R-RL2.

SEQ ID NO: 9 shows the polynucleotide sequence that encodes one subunit of α-hemolysin M113F-RL2 used in the Example.

SEQ ID NO: 10 shows the amino acid sequence of one subunit of α-hemolysin M113F-RL2 used in the Example.

SEQ ID NO: 11 shows the polynucleotide sequence that encodes one subunit of α-hemolysin M113N-RL2 used in the Example.

SEQ ID NO: 12 shows the amino acid sequence of one subunit of α-hemolysin M113N-RL2 used in the Example.

SEQ ID NO: 13 shows the polynucleotide sequence that encodes one subunit of α-hemolysin M113C-D8RL2 used in the Example.

SEQ ID NO: 14 shows the amino acid sequence of one subunit of α-hemolysin M113C-D8RL2 used in the Example.

SEQ ID NO: 15 shows the amino acid sequence of one subunit of α-hemolysin T117C-D8RL3 used in the Example.

SEQ ID NO: 16 shows the polynucleotide sequence that encodes one subunit of α-hemolysin T117C-D8RL3 used in the Example.

SEQ ID NO: 17 shows the amino acid sequence of lambda exonuclease. The sequence is one of three identical subunits that assemble into a trimer.

SEQ ID NO: 18 shows the sequence encoding αHL-D8RL3 (the sequence in FIG. 12).

DETAILED DESCRIPTION OF THE INVENTION

It is to be understood that different applications of the disclosed products and methods may be tailored to the specific needs in the art. It is also to be understood that the terminology used herein is for the purpose of describing particular embodiments of the invention only, and is not intended to be limiting.

In addition as used in this specification and the appended claims, the singular forms "a", "an", and "the" include plural referents unless the content clearly dictates otherwise. Thus, for example, reference to "an analyte" includes "analytes", reference to "a transmembrane protein pore" includes two or more such pores, reference to "a molecular adaptor" includes two or more such adaptors, and the like.

All publications, patents and patent applications cited herein, whether supra or infra, are hereby incorporated by reference in their entirety.

Transmembrane Protein Pores

The present invention relates to a transmembrane protein pore for use in detecting an analyte. The transmembrane protein pore comprises a molecular adaptor that facilitates an interaction with the analyte. The adaptor is covalently attached to the pore in a specific orientation. The adaptor is oriented such that, during the interaction between the analyte and the pore, the analyte affects the current flowing through the pore in a manner specific for that analyte. The adaptor is therefore covalently attached to the pore in an orientation that allows the pore to be used to detect the analyte via stochastic sensing.

The transmembrane protein pore of the invention is a useful tool for stochastic sensing. The fixed nature of the molecular adaptor means that the signal obtained from the pore is entirely dependent on the presence of the analyte in the barrel or channel of the pore and is not affected by dissociation of the adaptor from the pore. In other words, the fixed nature of the adaptor means that a distinctive current will flow through the pore whenever an analyte interacts with the pore. This results in a more sensitive system that allows: (1) the detection of rare interaction events, such as when the concentration of the analyte is low; (2) the detection of common interaction events, such as when the analyte concentration is high; (3) the detection of long-lived interaction events, such as when the affinity of the analyte for the adaptor is high; and (4) the measurement of the dwell time of the analyte, so that the affinity of the analyte for the adaptor can be measured. Most importantly, the lack of any interruption in the signal means that every analyte that enters the pore is detected. Such an efficient detection system facilitates the sequencing of nucleic acids. This is discussed further below.

The transmembrane protein pore of the invention has additional benefits. As described in the Example, the transmembrane protein pore of the invention is capable of functioning at elevated temperatures, such as up to 55° C. or up to 100° C. This means that the pore is suitable for detecting analytes under extreme conditions.

The fixed nature of the molecular adaptor means that it is not free to interact with the analyte independently of the pore. This reduces interference and means that a more accurate measurement of the concentration of the analyte can be obtained.

As described in the Example, the attachment of the molecular adaptor to the pore permanently alters its ion selectivity. This allows the production of a transmembrane protein pore having a particular ion selectivity.

Finally, the fixed nature of the molecular adaptor means that the pore and adaptor can be stored together, thereby allowing the production of a ready-to-use sensor.

Transmembrane Protein Pore

A transmembrane protein pore is a polypeptide that permits ions to flow from one side of the membrane to the other along an applied potential. The pore preferably permits the analyte to flow from one side of the membrane to the other along the applied potential.

The pore is typically an oligomer. The pore is preferably made up of several repeating subunits, such as 6, 7 or 8 subunits. The pore is more preferably heptameric. The pore typically comprises a barrel or channel through which the ions may flow. The subunits of the pore typically surround a central axis and contribute strands to a transmembrane β barrel or channel or a transmembrane α-helix bundle or channel.

The barrel or channel of the pore typically comprises amino acids that facilitate interaction with the analyte. These amino acids are preferably located near the constriction of the barrel or channel. A pore for use in detecting nucleotides or nucleic acids typically comprises one or more positively charged amino acids, such as arginine, lysine or histidine. These amino acids typically facilitate the interaction between the pore and a nucleotide by interacting with the phosphate groups in the nucleotide or by π-cation interaction with the base in the nucleotide. A pore for use in detecting nucleotides or nucleic acids preferably has a ring of positively charged amino acids, such as arginine, lysine or histidine, located near the constriction of the barrel or channel. Each positively charged amino acid is typically provided by each of the pore subunits.

Pores for use in accordance with the invention can be β-barrel pores or α-helix bundle pores. β-barrel pores comprise a barrel or channel that is formed from β-sheets. Suitable β-barrel pores include, but are not limited to, β-toxins, such as α-hemolysin and leukocidins, and outer membrane proteins/porins of bacteria, such as *Mycobacterium smegmatis* porin A (MspA), outer membrane porin F (OmpF), outer membrane porin G (OmpG), outer membrane phospholipase A and *Neisseria* autotransporter lipoprotein (NalP). α-helix bundle pores comprise a barrel or channel that is formed from α-helices. Suitable α-helix bundle pores include, but are not limited to, inner membrane proteins and a outer membrane proteins, such as WZA.

The most preferred pore for use in the invention is α-hemolysin or a variant thereof. The α-hemolysin pore is formed of seven identical subunits (i.e. it is heptameric). The sequence of one subunit of α-hemolysin is shown in SEQ ID NO: 2. A variant is a heptameric pore in which one or more of the seven subunits has an amino acid sequence which varies from that of SEQ ID NO: 2 and which retains pore activity. A variant may include modifications that facilitate covalent attachment of the adaptor or orientation of the adaptor as discussed below.

1, 2, 3, 4, 5, 6 or 7 of the subunits in a variant α-hemolysin may have an amino acid sequence that varies from that of SEQ ID NO: 2. All seven subunits within a variant pore are may be identical but are typically different, particularly if one or more of the subunits has been modified to facilitate covalent attachment of the adaptor or orientation of the adaptor as discussed below.

Preferred variants of α-hemolysin for use in detecting nucleotides or nucleic acids have one or more positively charged amino acids, such as arginine, lysine or histidine, located near the constriction of the barrel or channel. The pore preferably has a ring of 4, 5, 6 or preferably 7 positively charged amino acids, such as arginine, lysine or histidine, located near the constriction of the barrel or channel. Each amino acid in the ring is typically provided by each of the variant subunits. Suitable variants include a positively charged amino acid at position 113 of each subunit. The pore for use in detecting nucleotides or nucleic acids is preferably α-hemolysin (M113K-RL2)$_7$ which comprises seven subunits as shown in SEQ ID NO: 4 or preferably α-hemolysin (M113H-RL2)$_7$ which comprises seven subunits as shown in SEQ ID NO: 6 or most preferably α-hemolysin (M113R-RL2)$_7$ which comprises seven subunits as shown in SEQ ID NO: 8.

Other preferred variants of α-hemolysin have one or more uncharged amino acids, such as asparagine, or one or more aromatic amino acids, such as phenylalanine, located near the constriction of the barrel or channel. This has the purpose of binding and orienting β-CD-PDP for the covalent attachment reaction, and maintaining orientation of β-CD-PDP after covalent attachment. The pore preferably has a ring of 4, 5, 6 or preferably 7 uncharged or aromatic amino acids located near the constriction of the barrel or channel. Each amino acid in the ring is typically provided by each of the variant subunits. Suitable variants include an uncharged or aromatic amino acid at position 113 of each subunit. The pore for use in accordance with the invention is preferably α-hemolysin (M113F-RL2)$_6$(M113C-D8RL2)$_1$.

The variant may be a naturally-occurring variant which is expressed by an organism, for instance by a *Staphylococcus* bacterium. Variants also include non-naturally occurring variants produced by recombinant technology. Over the entire length of the amino acid sequence of SEQ ID NO: 2, a subunit of a variant will preferably be at least 50% homologous to that sequence based on amino acid identity. More preferably, the subunit polypeptide may be at least 55%, at least 60%, at least 65%, at least 70%, at least 75%, at least 80%, at least 85%, at least 90% and more preferably at least 95%, 97% or 99% homologous based on amino acid identity to the amino acid sequence of SEQ ID NO: 2 over the entire sequence. There may be at least 80%, for example at least 85%, 90% or 95%, amino acid identity over a stretch of 200 or more, for example 230, 250, 270 or 280 or more, contiguous amino acids ("hard homology").

Amino acid substitutions may be made to the amino acid sequence of SEQ ID NO: 2, for example up to 1, 2, 3, 4, 5, 10, 20 or 30 substitutions. Conservative substitutions may be made, for example, according to Table 1 below.

TABLE 1

Conservative substitutions

| NON-AROMATIC | Non-polar | G A P |
| --- | --- | --- |
|  |  | I L V |
|  | Polar - uncharged | C S T M |
|  |  | N Q |
|  | Polar - charged | D E |
|  |  | H K R |
| AROMATIC |  | H F W Y |

Amino acids in the same block in the second column and preferably in the same line in the third column may be substituted for each other.

One or more amino acid residues of the amino acid sequence of SEQ ID NO: 2 may alternatively or additionally be deleted. Up to 1, 2, 3, 4, 5, 10, 20 or 30 residues may be deleted, or more.

Variants may include subunits made of fragments of SEQ ID NO: 2. Such fragments retain pore forming activity. Fragments may be at least 50, 100, 200 or 250 amino acids in length. Such fragments may be used to produce chimeric pores. A fragment preferably comprises the pore forming domain of SEQ ID NO: 2.

Variants include chimeric protein pores comprising fragments or portions of SEQ ID NO: 2. Chimeric protein pores are formed from subunits each comprising fragments or portions of SEQ ID NO: 2. The pore or channel part of a chimeric protein pore is typically formed by the fragments or portions of SEQ ID NO: 2.

One or more amino acids may be alternatively or additionally added to the polypeptides described above. An extension may be provided at the N-terminus or C-terminus of the amino acid sequence of SEQ ID NO: 2 or polypeptide variant or fragment thereof. The extension may be quite short, for example from 1 to 10 amino acids in length. Alternatively, the extension may be longer, for example up to 50 or 100 amino acids. A carrier protein may be fused to an amino acid sequence according to the invention.

Standard methods in the art may be used to determine homology. For example the UWGCG Package provides the BESTFIT program which can be used to calculate homology, for example used on its default settings (Devereux et al (1984) *Nucleic Acids Research* 12, p387-395). The PILEUP and BLAST algorithms can be used to calculate homology or line up sequences (such as identifying equivalent residues or corresponding sequences (typically on their default settings)), for example as described in Altschul S. F. (1993) J Mol Evol 36:290-300; Altschul, S. F et al (1990) J Mol Biol 215:403-10.

Software for performing BLAST analyses is publicly available through the National Center for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSP's containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff (1992) *Proc. Natl. Acad. Sci.* USA 89: 10915-10919) alignments (B) of 50, expectation (E) of 10, M=5, N=4, and a comparison of both strands.

The BLAST algorithm performs a statistical analysis of the similarity between two sequences; see e.g., Karlin and Altschul (1993) *Proc. Natl. Acad. Sci*. USA 90: 5873-5787. One measure of similarity provided by the BLAST algorithm is the smallest sum probability (P(N)), which provides an indication of the probability by which a match between two amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

A transmembrane protein pore may be modified for example by the addition of histidine or aspartic acid residues to assist their identification or purification or by the addition of a signal sequence to promote their secretion from a cell where the polypeptide does not naturally contain such a sequence.

A pore may be labelled with a revealing label. The revealing label may be any suitable label which allows the pore to be detected. Suitable labels include, but are not limited to, fluorescent molecules, radioisotopes, e.g. $^{125}$I, $^{35}$S, enzymes, antibodies, antigens, polynucleotides and ligands such as biotin.

The pore may be isolated from a pore-producing organism, such as *Staphylococcus aureus*, or made synthetically or by recombinant means. For example, the pore may be synthesized by in vitro translation and transcription. The amino acid sequence of the pore may be modified to include non-naturally occurring amino acids or to increase the stability of the compound. When the pores are produced by synthetic means, such amino acids may be introduced during production. The pores may also be altered following either synthetic or recombinant production.

The pores may also be produced using D-amino acids. This is conventional in the art for producing such proteins or peptides.

As discussed in detail above and below, the pore can contain one or more specific modifications to facilitate attachment and orientation of the adaptor. The pore may also contain other non-specific modifications as long as they do not interfere with the attachment and orientation of the adaptor. A number of non-specific side chain modifications are known in the art and may be made to the side chains of the pores. Such modifications include, for example, reductive alkylation of amino acids by reaction with an aldehyde followed by reduction with $NaBH_4$, amidination with methylacetimidate or acylation with acetic anhydride.

A recombinant transmembrane pore can be produced using standard methods known in the art. Nucleic acid sequences encoding a pore or a pore subunit may be isolated and replicated using standard methods in the art. Nucleic acid sequences encoding a pore or a pore subunit may be expressed in a bacterial host cell using standard techniques in the art. The pore or a pore subunit may be produced in a cell by in situ expression of the polypeptide from a recombinant expression vector. The expression vector optionally carries an inducible promoter to control the expression of the polypeptide.

Nucleic acid sequences encoding a pore or a pore subunit may be isolated and replicated using standard methods in the art. Chromosomal DNA may be extracted from a pore-producing organism, such as *Staphylococcus aureus*. The gene encoding the pore or a pore subunit may be amplified using PCR involving specific primers. The amplified sequence may then be incorporated into a recombinant replicable vector such as a cloning vector. The vector may be used to replicate the nucleic acid in a compatible host cell. Thus nucleic acid sequences encoding a pore or a pore subunit may be made by introducing a polynucleotide encoding a pore or a pore subunit into a replicable vector, introducing the vector into a compatible host cell, and growing the host cell under conditions which bring about replication of the vector. The vector may be recovered from the host cell. Suitable host cells for cloning of polynucleotides encoding a pore or a pore subunit are known in the art and described in more detail below.

The nucleic acid sequence encoding a pore or a pore subunit may be cloned into suitable expression vector. In an expression vector, the nucleic acid sequence encoding a pore or a pore subunit is typically operably linked to a control sequence which is capable of providing for the expression of the coding sequence by the host cell. Such expression vectors can be used to express a pore or a pore subunit.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. Multiple copies of the same or different pore or pore subunit genes may be introduced into the vector.

The expression vector may then be introduced into a suitable host cell. Thus, in the case of a monomeric pore or a oligomeric pore comprising only one type of subunit, the method of the invention may be carried out on a cell produced by introducing a nucleic acid sequence encoding a pore or a pore subunit into an expression vector, introducing the vector into a compatible bacterial host cell, and growing the host cell under conditions which bring about expression of the nucleic acid sequence encoding the pore or the pore subunit. The recombinantly-expressed pore subunits will self-assemble into a pore in the host cell membrane. Alternatively, the recombinant pore produced in this manner may be isolated from the host cell and inserted into another membrane. In the case of an oligomeric pore comprising at least two different subunits, the different subunits may be expressed separately in different host cells as described above, removed from the host cells and assembled into a pore in a separate membrane, such as a rabbit cell membrane.

The vectors may be for example, plasmid, virus or phage vectors provided with an origin of replication, optionally a promoter for the expression of the said nucleic acid sequence and optionally a regulator of the promoter. The vectors may contain one or more selectable marker genes, for example a tetracycline resistance gene. Promoters and other expression regulation signals may be selected to be compatible with the host cell for which the expression vector is designed. A T7, trc, lac, ara or $\lambda_L$ promoter is typically used.

The host cell typically expresses the pore or the pore subunit at a high level. Host cells transformed with a nucleic acid sequence encoding a pore or a pore subunit will be chosen to be compatible with the expression vector used to transform the cell. The host cell is typically bacterial and preferably *Escherichia coli*. Any cell with a λ DE3 lysogen, for example C41 (DE3), BL21 (DE3), JM109 (DE3), B834 (DE3), TUNER, Origami and Origami B, can express a vector comprising the T7 promoter.

A pore or a pore subunit may be produced in large scale following purification by any protein liquid chromatography system from pore-producing organisms or after recombinant expression as described above. Typical protein liquid chromatography systems include FPLC, AKTA systems, the Bio-Cad system, the Bio-Rad BioLogic system and the Gilson HPLC system. The naturally-occurring or recombinantly-produced pore or or pore subunit may then be inserted into a naturally-occurring or artificial membrane for use in accordance with the invention.

Pores or pore subunits can be inserted into a membrane using any method known in the art. For instance, pores or pore subunits can be introduced into a membrane using the "pick and place" method described in International Application No. PCT/GB2006/001057 (published as WO 2006/100484).

Molecular Adaptor

The transmembrane pore comprises a molecular adaptor that facilitates the interaction between the pore and the analyte. The presence of the adaptor improves the host-guest chemistry of the pore and the analyte. The principles of host-guest chemistry are well-known in the art. The adaptor has an effect on the physical or chemical properties of the pore that improves its interaction with the analyte. The adaptor typically alters the charge of the barrel or channel of the pore or specifically interacts with or binds to the analyte thereby facilitating its interaction with the pore.

Preferably, at least part of the adaptor is inside the barrel or channel of the pore. More preferably, all of the adaptor is inside the barrel or channel of the pore.

The adaptor mediates the interaction between the analyte and the pore. The analyte preferably reversibly binds to the pore via or in conjunction with the adaptor.

The analyte most preferably reversibly binds to the pore via or in conjunction with the adaptor as it passes through the pore across the membrane. The analyte can also reversibly bind to the barrel or channel of the pore via or in conjunction with the adaptor as it passes through the pore across the membrane. The adaptor preferably constricts the barrel or channel so that it may interact with the analyte. The adaptor more preferably constricts the barrel or channel and restricts flow of ions through the pore. Flow of ions through the pore is restricted if the presence of the adaptor interferes with movement of ions through the pore and across the membrane. Flow of ions through the pore is required for analyte detection. As discussed above, the interaction between the analyte and the pore affects the current of ions flowing through the pore in a manner specific for that analyte. The adaptor is typically cyclic. The adaptor preferably has the same symmetry as the pore. An adaptor having seven-fold symmetry is typically used if the pore is heptameric (e.g. has seven subunits around a central axis that contribute 14 strands to a transmembrane β barrel). Likewise, an adaptor having six-fold symmetry is typically used if the pore is hexameric (e.g. has six subunits around a central axis that contribute 12 strands to a transmembrane β barrel, or is a 12-stranded β barrel).

The adaptor typically interacts with, such as binds to, the analyte. Interaction, such as binding, between the adaptor and the analyte increases the likelihood that the analyte interacts with the pore. The adaptor typically interacts with the analyte via host-guest chemistry. A portion of the adaptor is typically capable of interacting with the analyte. The portion comprises one or more chemical groups that are capable of interacting with the analyte. The one or more chemical groups preferably interact with the analyte by non-covalent interactions, such as hydrophobic interactions, hydrogen bonding, Van der Waal's forces, π-cation interactions and/or electrostatic forces. The one or more chemical groups that are capable of interacting with the analyte preferably comprise amino groups and/or hydroxyl groups. The amino groups or hydroxyl groups can be attached to primary, secondary or tertiary carbon atoms.

The portion of the adaptor that is capable of interacting with the analyte preferably comprises an aromatic ring that is capable of interacting with the analyte via π-cation interactions. The portion of the adaptor that is capable of interacting with the analyte more preferably comprises a ring of amino groups or hydroxyl groups, such as a ring of 6, 7 or 8 amino groups or hydroxyl groups. The portion most preferably comprises a ring of seven amino groups or hydroxyl groups. A ring of protonated amino groups may interact with negatively charged groups in an analyte, such as phosphate groups in a nucleotide. A ring of amino groups may interact with an analyte in combination with a ring of positively charged amino acids in the constriction of the barrel or channel of the pore. A ring of hydroxyl groups may interact with the analyte via hydrogen bonding. A ring of hydroxyl groups may interact with the analyte in combination with a ring of uncharged amino acids in the constriction of the barrel or channel of the pore.

The adaptor most preferably (1) constricts the barrel or channel and thereby restricts flow of ions through the pore and (2) interacts with or binds to the analyte.

As discussed in more detail below, the correct orientation of the adaptor within the barrel or channel of the pore can be facilitated by host-guest chemistry between the adaptor and the pore. The adaptor preferably comprises one or more chemical groups that are capable of interacting with one or more amino acids in the pore. The adaptor more preferably comprises one or more chemical groups that are capable of interacting with one or more amino acids in the pore via non-covalent interactions, such as hydrophobic interactions, hydrogen bonding, Van der Waal's forces, π-cation interactions and/or electrostatic forces. The chemical groups that are capable of interacting with one or more amino acids in the pore are typically hydroxyls. The hydroxyl groups can be attached to primary, secondary or tertiary carbon atoms. The hydroxyl groups may form hydrogen bonds with uncharged amino acids in the pore, preferably in the barrel or channel of the pore. As discussed in more detail below below, the interaction of one or more chemical groups in the adaptor with one or more amino acids in the pore can be used to hold the adaptor in the correct orientation. The one or more chemical groups in the adaptor that are capable of interacting with one or more amino acids in the pore to hold the adaptor in the correct orientation may be the same one or more chemical groups that are capable of interacting with the analyte or may be different from the one or more chemical groups that are capable of interacting with the analyte.

Any adaptor that that facilitates the interaction between the pore and the analyte can be used. Suitable adaptors include, but are not limited to, cyclodextrins, cyclic peptides and cucurbiturils. The adaptor is preferably heptakis-6-amino-β-cyclodextrin ($am_7$-β-CD) or 6-monodeoxy-6-monoamino-β-cyclodextrin ($am_1$β-CD). Table 2 below shows preferred combinations of pores and adaptors.

TABLE 2

Suitable combinations of pores and adaptors

| Pore | Number of strands in the transmembrane β-barrel | Adaptor |
|---|---|---|
| Leukocidin | 16 | γ-cyclodextrin (γ-CD) |
| OmpF | 16 | γ-cyclodextrin (γ-CD) |
| α-hemolysin (or a variant thereof discussed above) | 14 | β-cyclodextrin (β-CD) 6-monodeoxy-6-monoamino-β-cyclodextrin ($am_1$β-CD) heptakis-6-amino-β-cyclodextrin ($am_7$-β-CD) |
| OmpG | 14 | β-cyclodextrin (β-CD) 6-monodeoxy-6-monoamino-β-cyclodextrin ($am_1$β-CD) heptakis-6-amino-β-cyclodextrin ($am_7$-β-CD) |
| NalP | 12 | α-cyclodextrin (α-CD) |
| OMPLA | 12 | α-cyclodextrin (α-CD) |

Preferably, the adaptor is not a linear polymer of repeating subunits, such as a peptide, polypeptide, protein, nucleic acid or polynucleotide. More preferably, the adaptor is not a protein kinase inhibitor peptide.

Covalent Attachment

The adaptor is covalently attached to the pore. The adaptor can be covalently attached to the pore using any method known in the art. The adaptor may be attached directly to the pore. The adaptor is preferably attached to the pore using a bifunctional crosslinker. Suitable crosslinkers are well-known in the art. A preferred crosslinker is succinimidyl 3-(2-pyridyldithio)propionate (SPDP). Typically, the adaptor is covalently attached to the bifunctional crosslinker before the adaptor/crosslinker complex is covalently attached to the pore but it is also possible to covalently attach the bifunctional crosslinker to the pore before the bifunctional crosslinker/pore complex is attached to the adaptor.

The site of covalent attachment is selected such that the adaptor facilitates interaction of the analyte with the pore and thereby allows detection of the analyte. The site of covalent attachment is selected such that the analyte affects the current flowing through the pore in a manner specific for that analyte.

Preferably, the adaptor is covalently attached to the barrel or channel of the pore. The adaptor can be covalently attached at any site in the barrel or channel as long as the adaptor facilitates interaction of the analyte with the pore and thereby allows detection of the analyte. Preferably, the adaptor is covalently attached to an amino acid in the barrel or channel that is close to the site at which the interaction between the adaptor and the barrel or channel takes place. If the adaptor is covalently attached to an amino acid in the barrel or channel that is far from the site at which the interaction between the adaptor and the barrel or channel takes place, a bifunctional crosslinker of suitable length may be used so that the adaptor can reach the site in the barrel or channel at which the interaction between the adaptor and the barrel or channel takes place. The adaptor does not have to be attached to the site within the barrel or channel with which it reversibly interacts when contacted with the pore.

The pore is preferably modified to facilitate the covalent attachment of the molecular adaptor with the bifunctional crosslinker. The barrel or channel of the pore is more preferably modified to facilitate the covalent attachment of the molecular adaptor with the bifunctional crosslinker. The pore may be modified using any method known in the art. Any of the variants discussed above may be used to facilitate the covalent attachment of the molecular adaptor or the bifunctional crosslinker.

The modification typically involves the introduction of one or more, such as 1, 2, 3, 4, 5, 6 or 7, amino acids into the pore, preferably the barrel or channel of the pore, to facilitate covalent attachment of the adaptor with the bifunctional crosslinker. The one or more amino acids may be introduced into the same or different subunits of the pore. Any amino acid that is capable of forming a covalent bond, such as cysteine, can be introduced. The amino acid may be naturally-occurring or non-naturally occurring. The one or more amino acids are preferably introduced by substitutions. Table 3 below shows an example of the types of amino acids that can be introduced into the pore to facilitate the covalent attachment of the adaptor or the bifunctional crosslinkers via specific chemical groups.

TABLE 3

Modification of the pore to facilitate covalent attachment of the adaptor

| Chemical group(s) in the adaptor or bifunctional crosslinker | Example(s) of adaptors containing the chemical groups | Example(s) of crosslinker containing the chemical group(s) | Amino acid(s) that can be introduced into the pore |
|---|---|---|---|
| Pyridyl disulfide group | | succinimidyl 3-(2-pyridyl-dithio)propionate (SPDP) | Cysteine |

In a preferred embodiment, a cysteine residue is introduced into a heptameric pore using one of the subunits shown in SEQ ID NOs: 14 and 16.

Orientation of the Adaptor

The adaptor is covalently attached to the pore in an orientation that allows the analyte to be detected using the pore. The adaptor is oriented such the analyte affects the current flowing through the pore in a manner specific for that analyte. The adaptor is oriented so this it improves the host-guest chemistry of the pore and analyte. The adaptor is oriented so that it affects the physical or chemical properties of the pore and improves its interaction with the analyte. If the adaptor is capable of specifically interacting with or binding to the analyte, the adaptor is oriented so that it specifically interacts with or binds to the analyte. In the latter embodiment, the portion of the adaptor that interacts with the analyte is preferably oriented towards the end of the pore through which the analyte enters. More preferably, one or more chemical groups in the adaptor that are capable of interacting with the analyte are oriented towards the end of the pore through which the analyte enters. The groups are preferably amino groups or hydroxyl groups. The end of the pore through which the analyte enters may be the cis end or the trans end. The end is preferably the trans end.

The orientation of the adaptor is determined by the covalent attachment and/or the host-guest chemistry between the adaptor and the pore. The covalent attachment may be designed so that the adaptor is correctly oriented. For instance, the site (e.g. amino acid) at which the adaptor is covalently attached to the pore may be designed so that the adaptor is correctly oriented and/or a bifunctional crosslinker may be used so that the adaptor is correctly oriented.

Preferably, the pore is modified to facilitate orientation of the adaptor. Modification of the pore can improve the host-guest chemistry between the adaptor and the pore and thereby hold the adaptor in the correct orientation. More preferably, the barrel or channel of the pore is modified to facilitate orientation of the adaptor. The barrel or channel of the pore may be modified at any site that facilitates orientation of the adaptor. Preferably, the barrel or channel of the pore is modified at the site(s) at which host-guest chemistry occurs between the covalently-attached adaptor and the pore. Most preferably, one or more amino acids in the barrel or channel of the pore that are capable of interacting with the covalently-attached adaptor via non-covalent interactions are modified to facilitate orientation of the adaptor. The amino acids that are modified may be one or more of the amino acids discussed above that facilitate interaction of the pore with the analyte. The pore may be modified using any method known in the art. Any of the variants discussed above may be used to facilitate the orientation of the molecular adaptor.

The modification typically involves the introduction into the pore, or preferably the barrel or channel, of one or more, such as 1, 2, 3, 4, 5, 6 or 7, amino acids to facilitate the orientation of the adaptor. The one or more amino acids may be introduced into the same or different subunits. The one or amino acids are preferably amino acids that hold the adaptor in the correct orientation. The one or amino acids are more preferably amino acids that hold the adaptor in the correct orientation via non-covalent interactions, such as hydrophobic interactions, hydrogen bonding, Van der Waal's forces, π-cation interactions and/or electrostatic forces. The one or more amino acids may be naturally-occurring or non-naturally occurring. The one or more amino acids are preferably uncharged amino acids. The uncharged amino acids may be polar, such as asparagine, or nonpolar, such as phenylalanine. Uncharged amino acids in the pore can orientate the adaptor by interacting with hydroxyl groups in the adaptor via hydrogen bonding. The one or more amino acids are preferably introduced by substitutions. Table 4 below shows the types of amino acids that can be introduced into the pore to correctly orient adaptors containing different chemical groups.

TABLE 4

Modification of the pore to orient the adaptor

| Chemical group(s) in the adaptor | Example(s) of adaptors containing the chemical groups | Amino acid(s) that can be introduced into the pore to orient the adaptor | Interaction |
|---|---|---|---|
| Hydroxyl groups attached to primary carbon atoms | 6-monodeoxy-6-monoamino-β-cyclodextrin (am$_1$βCD) | Phenylalanine | Hydrophobic interactions |
| Hydroxyl groups attched to secondary carbon atoms | 6-monodeoxy-6-monoamino-β-cyclodextrin (am$_1$βCD) | Asparagine | Hydrogen bonding |

In a preferred embodiment, a heptameric pore comprises six phenylalanine residues that are capable of orienting an adaptor containing hydroxyl groups attached to primary carbon atoms, such as 6-monodeoxy-6-monoamino-β-cyclodextrin (am$_1$βCD), towards the cis side of the pore. The heptameric pore can comprise six of the subunits shown in SEQ ID NO: 10.

In another preferred embodiment, a heptameric pore comprises six asparagine residues that are capable of orienting an adaptor containing secondary hydroxyl groups, such as 6-monodeoxy-6-monoamino-β-cyclodextrin (am$_1$βCD), towards the trans side of the pore. The heptameric pore can comprise six of the subunits shown in SEQ ID NO: 12.

Most preferably, the pore is modified to facilitate the covalent attachment and to facilitate the orientation of the adaptor. In such an embodiment, the spatial relationship between the site of covalent attachment and site(s) at which the pore is modified to facilitate the orientation of the adaptor is designed to ensure that the adaptor is held in the correct orientation. The modification can be made anywhere within the pore, preferably in the barrel or channel, as long as the adaptor is held in the correct orientation. Preferably, the modification that facilitates the covalent attachment and the modification(s) that facilitate the orientation of the adaptor are spatially proximate within the pore. More preferably, the modification that facilitates the covalent attachment and the modification(s) that facilitate the orientation of the adaptor are made in the same ring of amino acids within the barrel or channel of the pore. One amino acid in the ring may be modified to facilitate covalent attachment of the adaptor, while one or more, such as 1, 2, 3, 4, 5 or 6, of the other amino acids in the ring can be modified to facilitate orientation of the adaptor. If the modification that facilitates the covalent attachment is distant from the modification(s) that facilitate the orientation of the adaptor, a bifunctional crosslinker of appropriate length may be used to ensure that the adaptor is positioned close to the modification(s) that facilitate the orientation of the adaptor and thereby correctly oriented. Any of the modifications discussed above can be used.

In the most preferred embodiment, a heptameric pore is produced using six of the subunits shown in SEQ ID NO: 10 and one of the subunits shown in SEQ ID NO: 14 or using six of the subunits shown in SEQ ID NO: 12 and one of the subunits shown in SEQ ID NO: 16.

Method of Producing the Transmembrane Protein Pores of the Invention

The invention also relates to a method of producing a transmembrane protein pore of the invention. The method comprises covalently attaching to a transmembrane protein pore a molecular adaptor that facilitates an interaction between the pore and an analyte. The adaptor can be covalently attached to the pore using any method known in the art.

Any of the pores, adaptors and bifunctional crosslinkers discussed above can be used in the method. The site of covalent attachment is selected as discussed above.

The pore is preferably modified to facilitate the covalent attachment of the adaptor and/or to facilitate the orientation of the adaptor. This is discussed in more detail above.

The method also comprises determining whether or not the adaptor is attached to the pore in an orientation that allows the analyte to be detected using the pore. This involves determining whether or not the transmembrane protein pore can be used to determine the presence or absence of the analyte. This can be done as described in more detail below. If the presence or absence of the analyte can be determined, the adaptor is in the correct orientation and a transmembrane protein pore of the invention has been produced. If the presence or absence of the analyte cannot be determined, the adaptor is likely to be in an incorrect orientation and a transmembrane protein pore of the invention has not been produced.

Method of Detecting Analytes

The present invention also relates to a method of determining the presence or absence of an analyte. The method comprises contacting the analyte with a transmembrane protein pore of the invention so that the analyte interacts with the pore and measuring the current passing through the pore during the interaction and thereby determining the presence or absence of the analyte. Any of the transmembrane protein pores of the invention can be used. The benefits associated with using a transmembrane protein pore of the invention to detect an analyte is discussed above.

The analyte is present if the current flows through the pore in a manner specific for the analyte (i.e. if a distinctive current associated with the analyte is detected flowing through the pore). The analyte is absent if the current does not flow through the pore in a manner specific for the analyte.

The invention therefore involves stochastic sensing of an analyte. The invention can be used to differentiate analytes of similar structure on the basis of the different effects they have on the current passing through a transmembrane protein pore. The invention can also be used to measure the concentration of a particular analyte in a sample.

The invention may also be used in a sensor that uses many or thousands of pores of the invention in bulk sensing applications.

The method may be carried out using any suitable membrane/pore system in which a transmembrane protein pore of the invention is inserted into a membrane. The method is typically carried out using (i) an artificial membrane comprising a transmembrane protein pore of the invention, (ii) an isolated, naturally-occurring membrane comprising a transmembrane protein pore of the invention, or (iii) a cell expressing a transmembrane protein pore that has been modified in accordance with the invention. The method is preferably carried out using an artificial membrane. The membrane may comprise other transmembrane and/or intramembrane proteins as well as other molecules in addition to the transmembrane protein pore of the invention.

The method of the invention is typically carried out in vitro.

Membrane

The membrane forms a barrier to the flow of ions and analytes. The membrane is preferably a lipid bilayer. Lipid bilayers suitable for use in accordance with the invention can be made using methods known in the art. For example, lipid bilayer membranes can be formed using the method of Montal and Mueller (1972). The method of the invention may be carried out using lipid bilayers formed from any membrane lipid including, but not limited to, phospholipids, glycolipids, cholesterol and mixtures thereof. The lipid bilayer is preferably formed from 1,2-diphytanoyl-sn-glycero-3-phosphocholine.

Methods are known in the art for inserting pores into membranes, such as lipid bilayers. For example, the pore may be suspended in a purified form in a solution containing a lipid bilayer such that it diffuses to the lipid bilayer and is inserted by binding to the lipid bilayer and assembling into a functional state. Alternatively, the pore may be directly inserted into the membrane using the method described in M. A. Holden, H. Bayley. J. Am. Chem. Soc. 2005, 127, 6502-6503.

Interaction Between the Pore and Analyte

The analyte may be contacted with the pore on either side of the membrane. The analyte may be introduced to the pore on either side of the membrane. The analyte may be contacted with the side of the membrane that allows the analyte to pass through the pore to the other side of the membrane. For example, the analyte is contacted with an end of the pore, which in its native environment allows the entry of ions or small molecules, such as analytes, into the barrel or channel of the pore such that the analyte may pass through the pore. In such cases, the analyte interacts with the pore and/or adaptor as it passes across the membrane through the barrel or channel of the pore. Alternatively, the analyte may be contacted with the side of the membrane that allows the analyte to interact with the pore via or in conjunction with the adaptor, dissociate from the pore and remain on the same side of the membrane. The present invention provides pores in which the orientation of the adaptor is fixed. As a result, the analyte is preferably contacted with the end of the pore towards which the adaptor is oriented. Most preferably, the analyte is contacted with the end of the pore towards which the portion of the adaptor that interacts with the analyte is orientated.

The analyte may interact with the pore in any manner and at any site. As discussed above, the analyte preferably reversibly binds to the pore via or in conjunction with the adaptor. The analyte most preferably reversibly binds to the pore via or in conjunction with the adaptor as it passes through the pore across the membrane. The analyte can also reversibly bind to the barrel or channel of the pore via or in conjunction with the adaptor as it passes through the pore across the membrane.

During the interaction between the analyte and the pore, the analyte affects the current flowing through the pore in a manner specific for that analyte. For example, a particular analyte will reduce the current flowing through the pore for a particular mean time period and to a particular extent. In other words, the current flowing through the pore is distinctive for a particular analyte. Control experiments may be carried out to determine the effect a particular analyte has on the current flowing through the pore. Results from carrying out the method of the invention on a test sample can then be compared with those derived from such a control experiment in order to identify a particular analyte in the sample or determine whether a particular analyte is present in the sample. The frequency at which the current flowing through the pore is affected in a manner indicative of a particular analyte can be used to determine the concentration of that analyte in the sample.

Apparatus

The method may be carried out using any apparatus that is suitable for investigating a membrane/pore system in which a transmembrane protein pore is inserted into a membrane. The method may be carried out using any apparatus that is suitable for stochastic sensing. For example, the apparatus comprises a chamber comprising an aqueous solution and a barrier that separates the chamber into two sections. The barrier has an aperture in which the membrane containing the pore is formed. The analyte may be contacted with the pore by introducing the analyte into the chamber. The analyte may be introduced into either of the two sections of the chamber.

The method of the invention involves measuring the current passing through the pore during interaction with the analyte. Therefore the apparatus also comprises an electrical circuit capable of applying a potential and measuring an electrical signal across the membrane and pore. The method may be carried out using a patch clamp or a voltage clamp. The method preferably involves the use of a voltage clamp. The Example discloses one way to carry out a voltage clamp method.

Analyte

The analyte can be any substance in a sample. Suitable analytes include, but are not limited to, metal ions, inorganic salts, polymers, such as a polymeric acids or bases, dyes, bleaches, pharmaceuticals, diagnostic agents, recreational drugs, explosives and environmental pollutants.

The analyte can be an analyte that is secreted from cells. Alternatively, the analyte can be an analyte that is present inside cells such that the analyte must be extracted from the cells before the invention can be carried out.

The analyte is preferably an amino acid, peptide, polypeptide or a protein. The amino acid, peptide, polypeptide or protein can be naturally-occurring or non-naturally-occurring. The polypeptide or protein can include within it synthetic or modified amino acids. A number of different types of modification to amino acids are known in the art. For the purposes of the invention, it is to be understood that the analyte can be modified by any method available in the art.

The protein can be an enzyme, antibody, hormone, growth factor or growth regulatory protein, such as a cytokine. The cytokine may be selected from an interleukin, preferably IFN-1, IL-2, IL-4, IL-5, IL-6, IL-10, IL-12 or IL-13, an interferon, preferably IL-γ or other cytokines such as TNF-α. The protein may be a bacterial protein, fungal protein, virus protein or parasite-derived protein. Before it is contacted with the pore, the protein may be unfolded to form a polypeptide chain and thereby allow it to enter the barrel or channel of the pore and interact with the pore via or in conjunction with the adaptor.

The detection of nucleotides and nucleic acids is discussed in more detail below.

The analyte is present in any suitable sample. The invention is typically carried out on a sample that is known to contain or suspected to contain the analyte. The invention may be carried out on a sample that contains one or more analytes whose identity is unknown. Alternatively, the invention may be carried out on a sample to confirm the identity of one or more analytes whose presence in the sample is known or expected.

The sample may be a biological sample. The invention may be carried out in vitro on a sample obtained from or extracted from any organism or microorganism. The organism or microorganism is typically prokaryotic or eukaryotic and typically belongs to one the five kingdoms: plantae, animalia, fungi, monera and protista. The invention may be carried out in vitro on a sample obtained from or extracted from any virus. The sample is preferably a fluid sample. The sample typically comprises a body fluid of the patient. The sample may be urine, lymph, saliva, mucus or amniotic fluid but is preferably blood, plasma or serum. Typically, the sample is human in origin, but alternatively it may be from another mammal animal such as from commercially farmed animals such as horses, cattle, sheep or pigs or may alternatively be pets such as cats or dogs.

The sample may be a non-biological sample. The non-biological sample is preferably a fluid sample. Examples of a non-biological sample include surgical fluids, water such as drinking water, sea water or river water, and reagents for laboratory tests.

The sample is typically processed prior to being assayed, for example by centrifugation or by passage through a membrane that filters out unwanted molecules or cells, such as red blood cells. The sample may be measured immediately upon being taken. The sample may also be typically stored prior to assay, preferably below −70° C.

Conditions

The method of the invention involves the measuring of a current passing through the pore during interaction with the analyte. Suitable conditions for measuring ionic currents through transmembrane protein pores are known in the art and disclosed in the Example. The method is carried out with a voltage applied across the membrane and pore. The voltage used is typically from −250 mV to +250 mV. The voltage used is preferably in a range having a lower limit selected from −200 mV, −150 mV, −100 mV, −50 mV, −20 mV and 0 mV and an upper limit independently selected from +10 mV, +20 mV, +50 mV, +100 mV, +150 mV and +200 mV.

The method is carried out in the presence of any alkali metal chloride salt. In the exemplary apparatus discussed above, the salt is present in the aqueous solution in the chamber. Potassium chloride (KCl), sodium chloride (NaCl) or caesium chloride (CsCl) is typically used. KCl is preferred. The salt concentration is typically from 0.1 to 2.5M, from 0.3 to 1.9M, from 0.5 to 1.8M, from 0.7 to 1.7M, from 0.9 to 1.6M or from 1M to 1.4M. The salt concentration is preferably about 1M.

The method is typically carried out in the presence of a buffer. In the exemplary apparatus discussed above, the buffer is present in the aqueous solution in the chamber. Any buffer may be used in the method of the invention. One suitable buffer is Tris-HCl buffer. The method is typically carried out at a pH of from 4.0 to 10.0, from 4.5 to 9.5, from 5.0 to 9.0, from 5.5 to 8.8, from 6.0 to 8.7 or from 7.0 to 8.8 or 7.5 to 8.5. The pH used is preferably about 8.0.

The method is typically carried out at from 0° C. to 100° C., from 15° C. to 95° C., from 16° C. to 90° C., from 17° C. to 85° C., from 18° C. to 80° C., 19° C. to 70° C., or from 20° C. to 60° C. The method is preferably carried out at room temperature.

Method of Identifying an Individual Nucleotide

The present invention also relates to a method of identifying an individual nucleotide. The method comprises contacting the nucleotide with a transmembrane protein pore of the invention so that the nucleotide interacts with the pore and measuring the current passing through the pore during the interaction and thereby determining the identity of the nucleotide. The invention therefore involves stochastic sensing of an individual nucleotide. The invention can be used to differentiate nucleotides of similar structure on the basis of the different effects they have on the current passing through a transmembrane protein pore. Individual nucleotides can be identified at the single molecule level from their current amplitude when they interact with the pore. The invention can also be used to determine whether or not a particular nucleotide is present in a sample. The invention can also be used to measure the concentration of a particular nucleotide in a sample.

Individual Nucleotide

An individual nucleotide in accordance with the invention is a single nucleotide. An individual nucleotide is one which is not bound to another polynucleotide by a nucleotide bond. A nucleotide bond involves one of the phosphate groups of a nucleotide being bound to the sugar group of another nucleotide. An individual nucleotide is typically one which is not bound by a nucleotide bond to another polynucleotide sequence of at least 5, at least 10, at least 20, at least 50, at least 100, at least 200, at least 500, at least 1000 or at least 5000 nucleotides. For example, the individual nucleotide has been digested from a target polynucleotide sequence, such as a DNA or RNA strand.

The method of the invention may be used to identify any nucleotide. The nucleotide can be naturally-occurring or artificial. A nucleotide typically contains a nucleobase, a sugar and at least one phosphate group. The nucleobase is typically heterocyclic. Suitable nucleobases include purines and pyrimidines and more specifically adenine, guanine, thymine, uracil and cytosine. The sugar is typically a pentose sugar. Suitable sugars include, but are not limited to, ribose and deoxyribose. The nucleotide is typically a ribonucleotide or deoxyribonucleotide. The nucleotide typically contains a monophosphate, diphosphate or triphosphate.

Suitable nucleotides include, but are not limited to, adenosine monophosphate (AMP), adenosine diphosphate (ADP), adenosine triphosphate (ATP), guanosine monophosphate (GMP), guanosine diphosphate (GDP), guanosine triphosphate (GTP), thymidine monophosphate (TMP), thymidine diphosphate (TDP), thymidine triphosphate (TTP), uridine monophosphate (UMP), uridine diphosphate (UDP), uridine triphosphate (UTP), cytidine monophosphate (CMP), cytidine diphosphate (CDP), cytidine triphosphate (CTP), cyclic adenosine monophosphate (cAMP), cyclic guanosine monophosphate (cGMP), deoxyadenosine monophosphate (dAMP), deoxyadenosine diphosphate (dADP), deoxyadenosine triphosphate (dATP), deoxyguanosine monophosphate (dGMP), deoxyguanosine diphosphate (dGDP), deoxyguanosine triphosphate (dGTP), deoxythymidine monophosphate (dTMP), deoxythymidine diphosphate (dTDP), deoxythymidine triphosphate (dTTP), deoxyuridine monophosphate (dUMP), deoxyuridine diphosphate (dUDP), deoxyuridine triphosphate (dUTP), deoxycytidine monophosphate (dCMP), deoxycytidine diphosphate (dCDP) and deoxycytidine triphosphate (dCTP). The nucleotide is preferably AMP, TMP, GMP, UMP, dAMP, dTMP, dGMP or dCMP.

The nucleotide may be derived from the digestion of a nucleic acid sequence such as ribonucleic acid (RNA) or deoxyribonucleic acid. Individual nucleotides from a single nucleic acid sequence may be contacted with the pore in a sequential manner in order to sequence the whole or part of the nucleic acid. Sequencing nucleic acids in accordance with the second embodiment of the invention is discussed in more detail below.

The nucleotide is typically unmodified, such as when the nucleotide is derived from the digestion of a nucleic acid sequence. Alternatively, the nucleotide may be modified or damaged. The nucleotide is typically methylated. The nucleotide may be labelled with a revealing label. The revealing label may be any suitable label which allows the nucleotide to be detected. Suitable labels include fluorescent molecules, radioisotopes, e.g. $^{125}I$, $^{35}S$, and linkers such as biotin.

The nucleotide is typically present in any suitable biological sample. Suitable biological samples are discussed above.

Carrying Out the Method

All of the discussion above concerning detecting analytes, and in particular concerning the pores, membranes, apparatus and conditions that may be used, equally applies to this method.

In terms of conditions, the voltage used is preferably about +130 mV for deoxy-ribo nucleotides 5' monophosphate, such as dAMP, dTMP, dGMP and dCMP, and +110 mV for ribo nucleotides 5' monophosphate, such as AMP, TMP, GMP and UMP. The method is preferably carried out at +130 mV at pH 8.0, 1M KCl for deoxy-ribo nucleotides 5' monophosphate, such as dAMP, dTMP, dGMP and dCMP, and at +110 mV at pH 8.0, 1M KCl for ribo nucleotides 5' monophosphate, such as AMP, TMP, GMP and UMP.

Method of Sequencing Nucleic Acids

The present invention also relates to a method of sequencing a target nucleic acid sequence. The method comprises (a) digesting an individual nucleotide from one end of the target sequence using a processive exonuclease; (b) contacting the nucleotide with a transmembrane protein pore of the invention so that the nucleotide interacts with the pore; (c) measuring the current passing through the pore during the interaction and thereby determining the identity of the nucleotide; and (d) repeating steps (a) to (c) at the same end of the nucleic acid sequence and thereby determining the sequence of the nucleic acid. Hence, the method involves stochastic sensing of each single nucleotide of a nucleic acid sequence in a successive manner in order to sequence the nucleic acid.

A transmembrane protein pore of the invention is particularly suited to this method. In order to effectively sequence the nucleic acid, it is important to ensure that every nucleotide in the nucleic acid is identified in a successive manner. The fixed nature of the adaptor in a transmembrane protein pore of the invention means that a distinctive current will flow through the pore whenever each successive nucleotide interacts with the pore.

The whole or only part of the nucleic acid may be sequenced using this method. The nucleic acid can be any length. For example, the nucleic acid can be at least 10, at least 50, at least 100, at least 150, at least 200, at least 250, at least 300, at least 400 or at least 500 nucleotides in length. The nucleic acid can be naturally-occurring or artificial. For instance, the method may be used to verify the sequence of a manufactured oligonucleotide. The method is typically carried out in vitro.

Steps (b) and (c) of this method are generally identical to the steps carried out in the method of identifying nucleotides discussed above. All of the discussion above concerning detecting analytes, and in particular concerning the pores, membranes, apparatus and conditions that may be used, equally applies to this method. The nucleic acid is typically present in any biological sample as discussed above.

Processive Exonuclease

The method of sequencing a target nucleic acid involves contacting the nucleic acid with a processive exonuclease to release individual nucleotides from one end of the nucleic acid. Processive exonucleases are enzymes that typically latch onto one end of a nucleic acid and digest the sequence one nucleotide at a time from that end. The processive exonuclease can digest the nucleic acid in the 5' to 3' direction or 3' to 5' direction. The end of the nucleic acid to which the processive exonuclease binds is typically determined through the choice of enzyme used and/or using methods known in the art. Hydroxyl groups or cap structures at either end of the nucleic acid sequence may typically be used to prevent or facilitate the binding of the processive exonuclease to a particular end of the nucleic acid sequence.

Any processive exonuclease enzyme may be used in the method. The preferred enzyme for use in the method is lambda exonuclease. The sequence of one subunit of lambda exonuclease is shown in SEQ ID NO: 17. Three identical subunits interact to form a trimer exonuclease. Variants of lambda exonuclease are enzymes formed of polypeptide subunits which have an amino acid sequence which varies from that of SEQ ID NO: 17 and which retain processive exonuclease activity. The variants may vary from SEQ ID NO: 17 in the same manner and to the same extent as discussed for variants of SEQ ID NO: 2 above. A variant preferably comprises the domains responsible for binding to the nucleic acid and for digesting the nucleic acid (catalytic domain). A variant preferably has an increased or reduced rate of enzyme activity as required and/or higher salt tolerance compared to the wild-type enzyme. The processive exonuclease may be produced using any of the methods discussed above for the production of transmembrane protein pores.

The method of sequencing a target nucleic acid sequence involves contacting the nucleic acid sequence with the processive exonuclease so that the nucleotides are digested from the end of the nucleic acid at a rate that allows identification of each individual nucleotide as discussed above. Methods for doing this are well known in the art. For example, Edman degradation is used to successively digest single amino acids from the end of polypeptide such that they may be identified using High Performance Liquid Chromatography (HPLC). A homologous method may be used in the present invention.

The processive exonuclease is preferably covalently attached to the transmembrane protein pore. Methods for covalently attaching the processive exonuclease to the pore are well known in the art.

The rate at which the processive exonuclease must function is typically slower than the optimal rate of a wild-type processive exonuclease. A suitable rate of activity of the processive exonuclease in the method of the second embodiment involves digestion of from 0.5 to 1000 nucleotides per second, from 0.6 to 500 nucleotides per second, 0.7 to 200 nucleotides per second, from 0.8 to 100 nucleotides per second, from 0.9 to 50 nucleotides per second or 1 to 20 or 10 nucleotides per second. The rate is preferably 1, 10, 100, 500 or 1000 nucleotides per second. A suitable rate of processive exonuclease activity can be achieved in various ways. For example, variant processive exonucleases with a reduced optimal rate of activity may be used in accordance with the invention.

The activity of processive exonucleases is typically pH dependent such that their activity falls as pH is reduced. Hence, the method of the second embodiment is typically carried out at a pH of from 7.5 to 8.0 or from 7.7 to 8.0. The pH used is preferably about 8.0.

The rate of activity of processive exonucleases typically falls as salt concentration rises. However, very high salt concentrations typically have a detrimental effect on the activity of the enzyme. Another way of limiting the rate of the enzyme is to carry out the method at a salt concentration that reduces the rate of the activity of the enzyme without adversely affecting its activity. For example, the method may be carried out at a salt concentration of from 0.5 to 1M. The salt concentration is preferably about 1M.

Kits

The present invention also relates to kits that may be used to carry out the method of sequencing a target nucleic acid sequence. The kits are therefore suitable for sequencing nucleic acids. The kits comprise a transmembrane pore of the invention and a processive exonuclease.

The kit may additionally comprise one or more other reagents or instruments which enable any of the embodiments of the method mentioned above to be carried out. Such reagents or instruments include one or more of the following: suitable buffer(s) (aqueous solutions), means to obtain a sample from a subject (such as a vessel or an instrument comprising a needle), means to amplify nucleic acid sequences, a membrane as defined above or voltage or patch clamp apparatus. Reagents may be present in the kit in a dry state such that a fluid sample resuspends the reagents. The kit may also, optionally, comprise instructions to enable the kit to be used in the method of the invention or details regarding which patients the method may be used for. The kit may, optionally, comprise nucleotides.

The following Example illustrates the invention:

Example

In this Example, we covalently attach β-cyclodextrin (β-CD) to the αHL pore, using the mutations at position 113 to orient the adaptors for covalent bonding and stabilize them within the pore lumen after reaction. This approach has two important outcomes. First, the adaptor cannot dissociate from the nanopore. Second, the orientation of the cyclodextrin can be controlled with either the primary hydroxyls or the secondary hydroxyls facing the trans entrance of the pore.

1. MATERIALS AND METHODS 1.1 αHL pores

The α-hemolysin mutant pores $(M113F-RL2)_7$ (WT background; SEQ ID NO: 10), $(M113N-RL2)_7$ (WT background; SEQ ID NO: 12), $(M113F-RL2)_6(M113C-D8RL2)_1$ (SEQ ID NOs: 10 and 14), $(M113N)_6(T117C-D8RL3)_1$ (SEQ ID NOs: 12 and 16) were expressed, assembled and purified as previously described.

RL2 is the product of a semisynthetic gene that was devised to permit cassette mutagenesis of the sequence encoding the transmembrane β barrel (Cheley, S., Braha, O., Lu, X., Conlan, S., and Bayley, H. (1999) *Protein Sci.* 8, 1257-1267). It contains six silent restriction sites and five altered amino acids in the encoded polypeptide sequence (K8A, V124L, G130S, N139Q and I142L). D8RL2 is RL2 with an octa-aspartate tail.

RL3 is identical to the WT αHL polypeptide at the amino acid level, but the gene contains six silent mutations in the region encoding the loop that aid cassette mutagenesis (S. Cheley, unpublished). D8RL3 is RL3 with an octa-aspartate tail. FIG. 12 shows the complete polynucleotide sequence of pT7-RL3-D8.

1.2 Chemicals

Reagents were obtained as follows: 1,2-diphytanoyl-sn-glycero-3-phosphocholine (Avanti Polar Lipids), pentane (JT Baker), hexadecane (99+%, Sigma-Aldrich), 6-monodeoxy-6-monoamino-β-cyclodextrin hydrochloride (99%, Cyclolabs Budapest, Hungary), Trizma base (99.9%, Sigma-Aldrich), concentrated HCl (analytical reagent grade, Fisher Scientific), potassium chloride (99%, Sigma-Aldrich), 2-adamantanamine.HCl (99%, Aldrich), succinimidyl 3-(2-pyridyldithio)propionate (SPDP, 95%, Fluka), triethylamine (99.5%, Fluka).

1.3 Synthesis of 6-monodeoxy-6-[3-(2-pyridyldithio)propionyl]monoamino-β-cyclodextrin(βCD-PDP)

6-Monodeoxy-6-monoamino-β-cyclodextrin ($am_1\beta CD$) hydrochloride (11.7 mg, 0.01 mmol) and succinimidyl 3-(2-pyridyldithio)propionate (SPDP, 6.24 mg, 0.02 mmol) were dissolved in 5 mL MeOH/$H_2O$ (1:1). Triethylamine (100 μL) was added over 5 min and the mixture was stirred overnight. The desired product appeared as a white precipitate, which was filtered off and washed successively with cold water and acetone. An analytical sample was obtained by recrystallization from DMSO and water. $^1H$ NMR (DMSO-d6): δ 8.61 (m, 1H), 7.82 (m, 2H), 7.25 (ddd, J 7.2, 4.8, 1.2 Hz, 1H), 5.75 (m, 14H), 4.83 (m, 7H), 4.67 (m, 7H), 3.64 (m, 35H), 2.99 (t, J=7.2 Hz, 2H), 2.55 (t, J=7.2 Hz, 2H). ESI-MS $[M+Na]^+$ 1353.37; theoretical distribution 1353.37, 100%; 1354.38, 52.3%; 1355.38, 26.3%; 1356.38, 8.7%; 1357.38, 2.7%; 1358.38, 0.8%. Found 1353.37, 100%; 1354.38, 58.6%; 1355.37, 33.1%; 1356.38, 12.6%; 1357.38, 4.3%; 1358.38, 1.2%.

1.4 Single Channel Current Recording

A bilayer of 1,2-diphytanoyl-sn-glycero-3-phosphocholine (Avanti Polar Lipids) was formed across an aperture of 100-150 μm in diameter in a polycarbonate film (20-μm thickness from Goodfellow, Malvern, Pa.) that divided a planar bilayer chamber into two compartments, cis and trans. Both compartments contained 1 mL of buffer. Engineered protein pores were added to the cis compartment, which was connected to ground. βCD-PDP was added to the trans compartment, which was connected to the head-stage of the amplifier.

All experiments were carried out at ±100 mV in 25 mM Tris.HCl, 1 M KCl, pH 8.0, at 22.5±2° C., unless otherwise stated. Fresh frozen aliquots of protein and βCD-PDP were used each day. Currents were recorded with a patch clamp amplifier (Axopatch 200B; Axon instruments, Foster City, Calif.), low pass filtered with a built-in 4-pole Bessel filter at 10 kHz, and sampled at 20 kHz by a computer equipped with a Digidata 1200 A/D converter (Axon instruments).

1.5 Data Analysis

Current traces were analysed with pClamp 9.0 software (Axon Instruments). Events were detected using the Event Detection feature, and used to construct amplitude and dwell time histograms. Origin (Microcal, Northampton, Mass.) was used for curve fitting and graph presentation.

1.6 Molecular Models

The pdb files of the heptameric α-hemolysin pores $(M113F-RL2)_7$ and $(M113N-RL2)_7$ provided by Michelle Montoya and Eric Gouaux were displayed in PyMOL (DeLano Scientific, San Carlos, Calif.). The βCD-PDP structure was also constructed in PyMOL by using the building tools.

2. RESULTS

Figure 1:
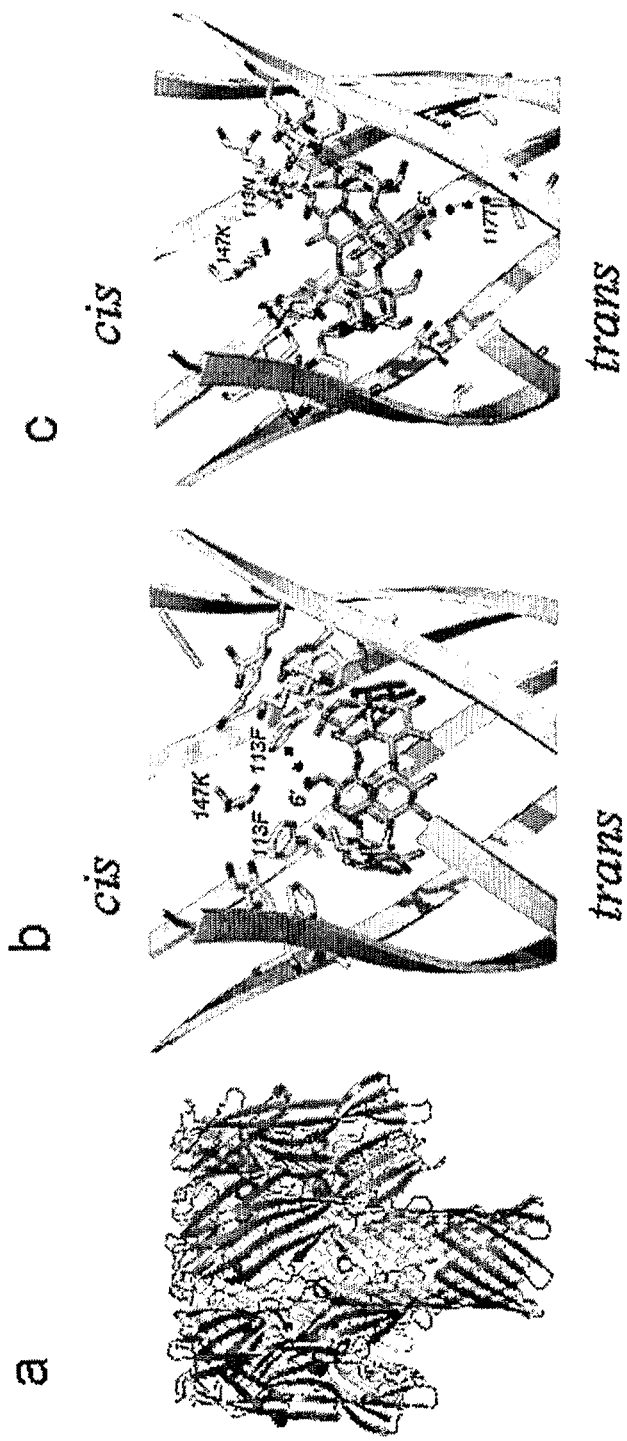
FIG. 1 shows X-ray structures of (M113F-RL2)$_7$•βCD and (M113N-RL2)$_7$•βCD generated from the pdb files (Montoya and Gouaux, unpublished). a) Side view of the βHL pore with amino acids 108 to 120 and 138 to 150 highlighted in yellow. b) (M113F)$_7$•βCD. Amino acids 108 to 120 of αHL are depicted in yellow and βCD is shown in blue sticks. The side chains of Phe-113 and Lys-147 are also shown in stick form. The distance between the O atom of a primary hydroxyl of βCD and the center of the nearest phenyl ring of Phe-113 is about 6.5 Å (dotted line). c) (M113N-RL2)$_7$•βCD. Amino acids 108 to 120 of αHL are depicted in yellow and βCD is shown in blue sticks. The side chains of Asn-113, Lys-147 and Thr-117 are also shown in stick form. The distance between the O atom of a primary hydroxyl of βCD and the nearest O atom of Thr-117 is about 6.0 Å (dotted line).

2.1 Design of the Linker and Derivatization of Engineered αHL Pores with βCD-PDP The X-ray structures of $(M113F-RL2)_7 \cdot \beta CD$ and $(M113N)_7 \cdot \beta CD$ (FIG. 1, Montoya and Gouaux, unpublished) reveal the positions of non-covalently bound βCD within the β barrel of the αHL pore. In $(M113F-RL2)_7 \cdot \beta CD$, the seven phenyl rings of Phe-113 take part in hydrophobic interactions with the seven primary 6-hydroxyl groups of βCD, resulting in a specific orientation of the βCD within the pore, in which the primary hydroxyls point towards the cis mouth (FIG. 1b). In contrast, in $(M113N-RL2)_7 \cdot \beta CD$, the seven amide groups of Asn-113 and the ε-amino groups of Lys-147 are, respectively, within hydrogen bonding distance of the seven 2- and the seven 3-secondary hydroxyl groups of βCD. In this orientation, the primary hydroxyl groups of βCD point towards the trans entrance of the pore (FIG. 1c).

Figure 2:
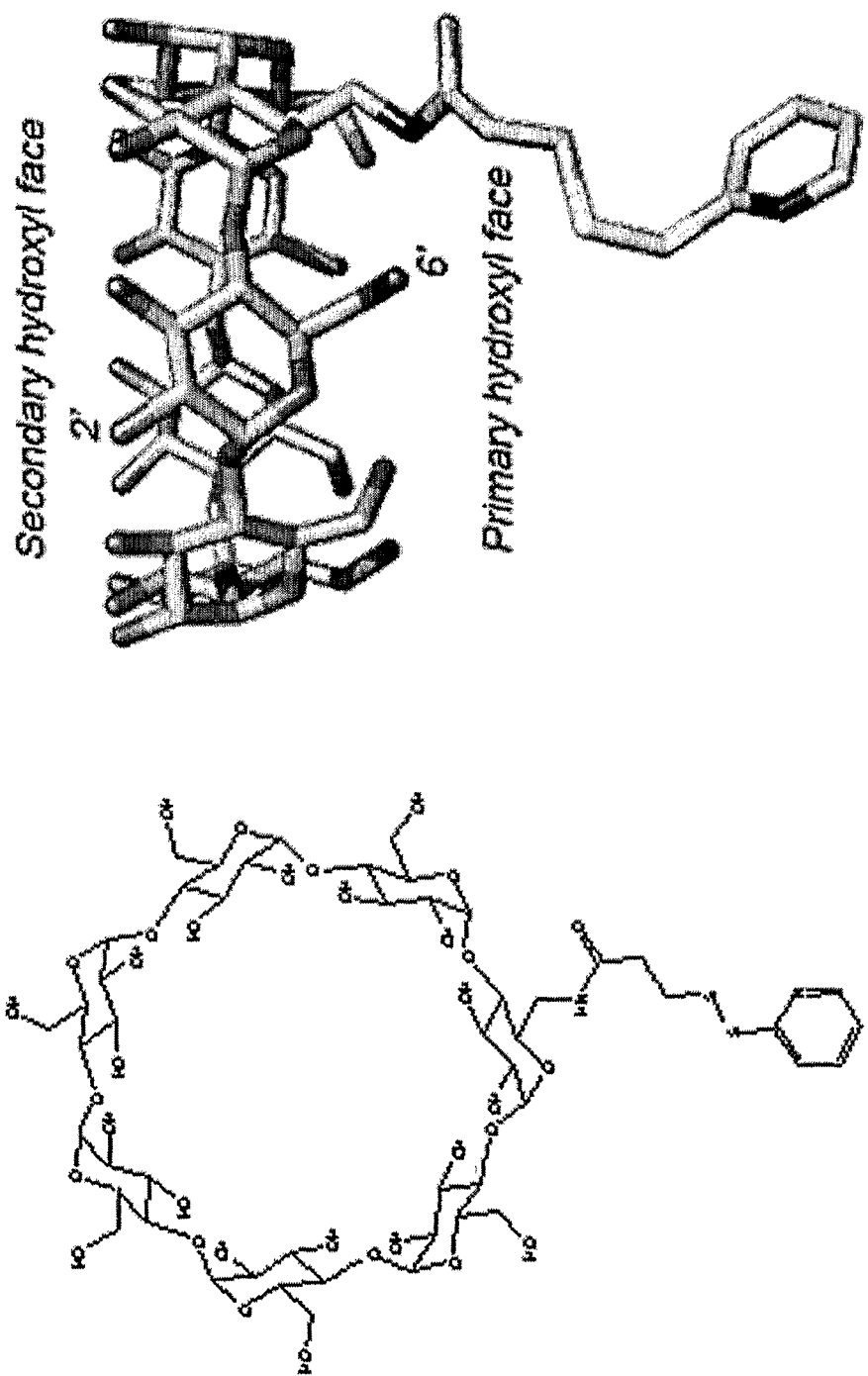
FIG. 2 shows the chemical structure and a stick representation of βCD-PDP. The molecule was drawn in ChemDraw 3D and then rendered in PyMol.

By molecular modeling, we identified suitable positions in the lumen of the αHL barrel at which to attach βCD. In $(M113F-RL2)_7 \cdot \beta CD$, the distance between the center of a phenyl ring of Phe-113 and the nearest O atom of a primary hydroxyl groups of βCD is 6.5±0.5 Å (average of the seven positions) (FIG. 1b). In $(M113N-RL2)_7 \cdot \beta CD$, the distance between the O atom of a primary hydroxyl groups of βCD and the closest O atom of Thr-117 is on average 6.0±0.5 Å (FIG. 1c). We chose a bifunctional crosslinker succinimidyl 3-(2-pyridyldithio)propionate (SPDP) to link 6-monodeoxy-6-monoamino-β-cyclodextrin ($am_1\beta CD$, in which a single primary hydroxyl group of βCD is substituted with an amino group) to a cysteine residue at position-113 or position-117. We first coupled $am_1\beta CD$ with SPDP to form βCD-PDP (FIG. 2). In βCD-PDP, the pyridyl disulfide at the end of the linker can be attacked by the free thiol of a cysteine residue in the αHL pore to form a disulfide bond. The length of the linker was measured by building PCD-PDP in PyMol; the distance between the N atom in the amide bond of $am_1\beta CD$ and the pyridyl S atom is approximately 7.0 Å in an extended conformation. Therefore, the linker is slightly longer than required for linking $am_1\beta CD$ to a cysteine at position-113 with the βCD in the orientation found in $(M113F-RL2)_7$ or to a cysteine at position-117 with the βCD in the orientation found in $(M113N-RL2)_7$.

On the basis of these modeling studies, a heteroheptameric αHL pore $(M113F-RL2)_6(M113C-D8RL2)_1$ was engineered with six phenylalanine residues at position-113 and a single cysteine at the seventh position. The cysteine residue in the M113C subunit was designed to be able to react with the pyridyl disulfide of βCD-PDP presented from the trans side of the bilayer in such a way that the primary hydroxyls of the cyclodextrin would remain in the proximity of the six Phe residues of the M113F subunits. After reaction, PCD would be anchored inside the αHL pore as a permanent molecular adaptor. In another construct, we placed a cysteine residue at position 117 in the engineered pore $(M113N-RL2)_6(T117C-D8RL3)_1$. This pore was designed to react with PCD-PDP while maintaining the stabilizing interactions of the secondary hydroxyls hydrogen bonded to residues Asn-113 and Lys-147 in the M113N subunits.

Figure 3:
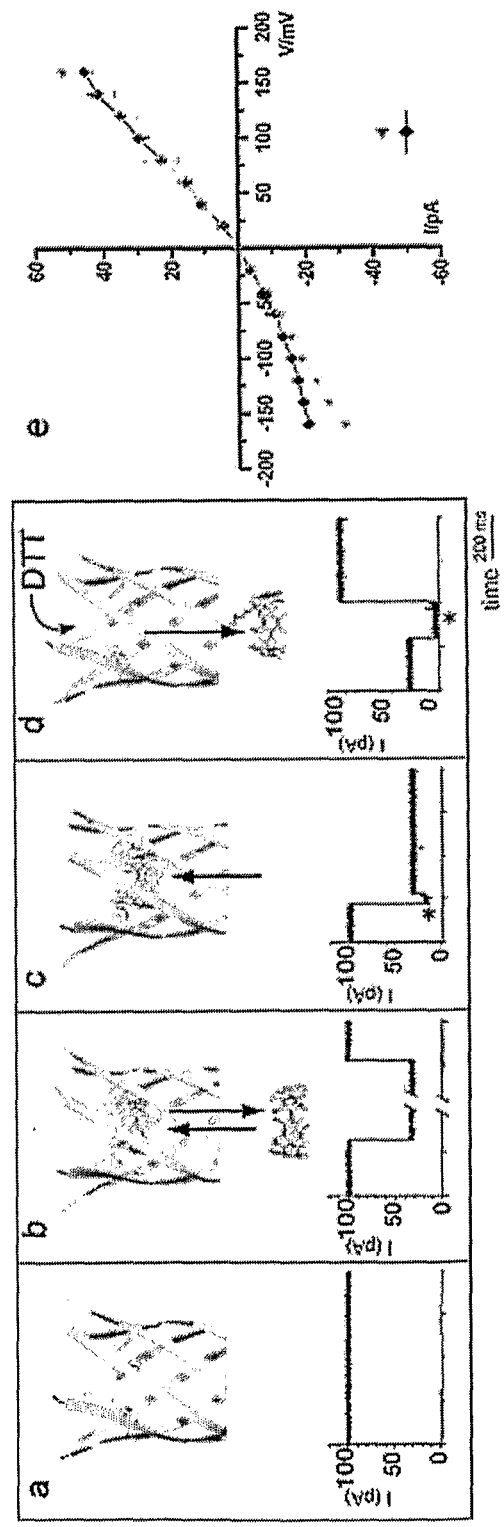
FIG. 3 shows a comparison of the properties of the non-covalent complex αHL (M113F-RL2)$_7$•βCD and the covalent adduct αHL (M113F-RL2)$_6$(M113C-D8RL2)$_1$-βCD. Each experiment was repeated at least 6 times. a) Cartoon representation of amino acids 108 to 120 of the mutant αHL pore (M113F-RL2)$_7$. Phe-113 residues are represented in stick form. Single-channel current trace from a (M113F-RL2)$_7$ pore in 25 mM Tris.HCl, pH 8.0, 1 M KCl, +100 mV. b) Cartoon representation of αHL (M113F-RL2)$_7$ with βCD bound as revealed by the X-ray structure of (M113F-RL2)$_7$•βCD. The arrows indicate that βCD is free to move in and out of the pore. The current trace shows an initially unoccupied pore followed by the binding of βCD and its subsequent dissociation (mean $\tau_{off}$=316±62 ms). c) Cartoon representation of amino acids 108 to 120 of αHL (M113F-RL2)$_6$(M113C-D8RL2)$_1$. Phe-113 residues are represented in stick form and Cys-113 is colored in brown and also represented in sticks. An enlarged view of (c) can be found in FIG. 4. The arrow indicates that when βCD-PDP enters the pore the primary hydroxyls interact with the side chains of Phe-113, and Cys-113 reacts with the pyridyl disulfide of βCD-PDP to form a disulfide bond. The current trace shows the current amplitude changes during the reaction. The transient state with 85% current block is marked (*). d) Cleavage of (M113F-RL2)$_6$(M113C-D8RL2)$_1$-βCD with dithiothreitol (DTT). The arrow indicates that the cyclodextrin derivative detaches from position 113 after cleavage of the disulfide bond with DTT. The current trace shows the current amplitude changes during cleavage. The transient state with 98% current block is marked (*). e) Single-channel I-V curves for (M113F-RL2)$_7$•βCD (τ) and αHL (M113F-RL2)$_6$(M113C-D8RL2)$_1$-βCD (□.). Conditions: 25 mM Tris.HCl, pH 8.0, 1 M KCl.
Figure 4:
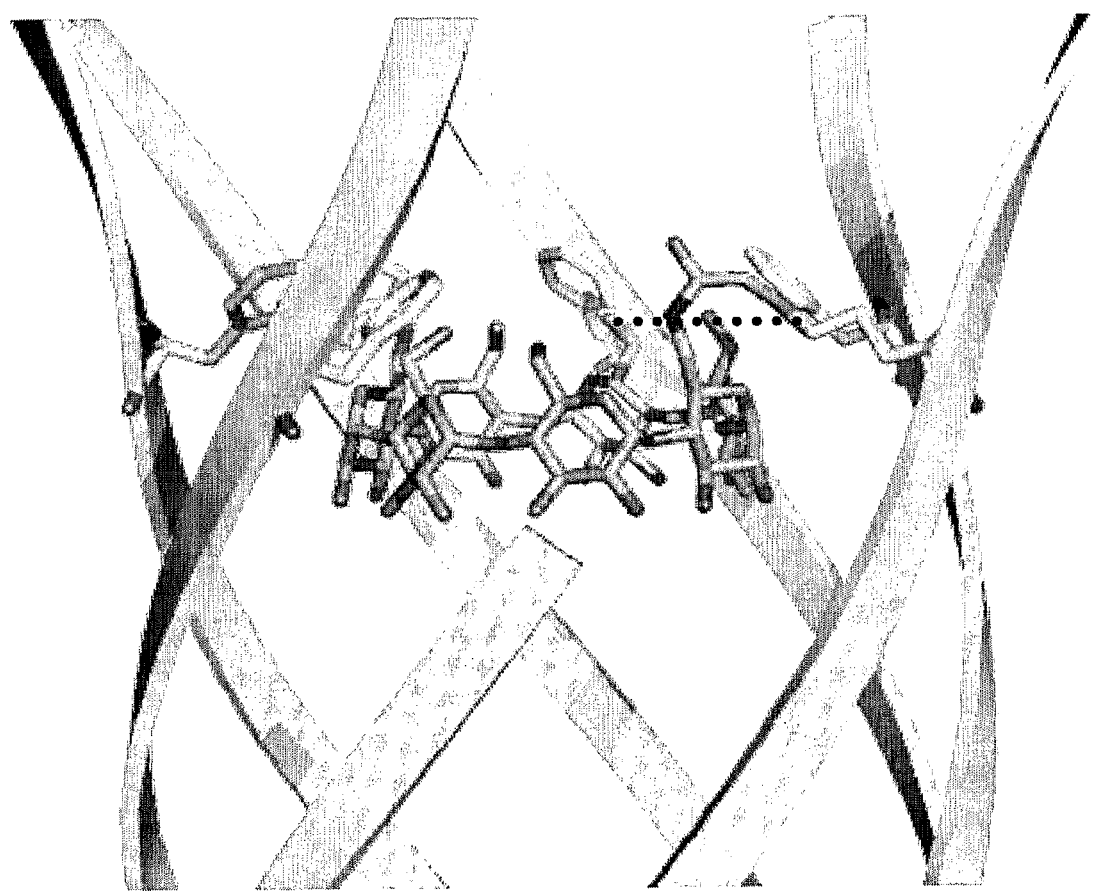
FIG. 4 shows an enlarged view of FIG. 3c. Cartoon representation of amino acids 108 to 120 of αHL (M113F-RL2)$_6$(M113C-D8RL2)$_1$. Phe-113 residues are represented in stick form and Cys-113 is colored in brown and also represented in sticks.
Figure 5:
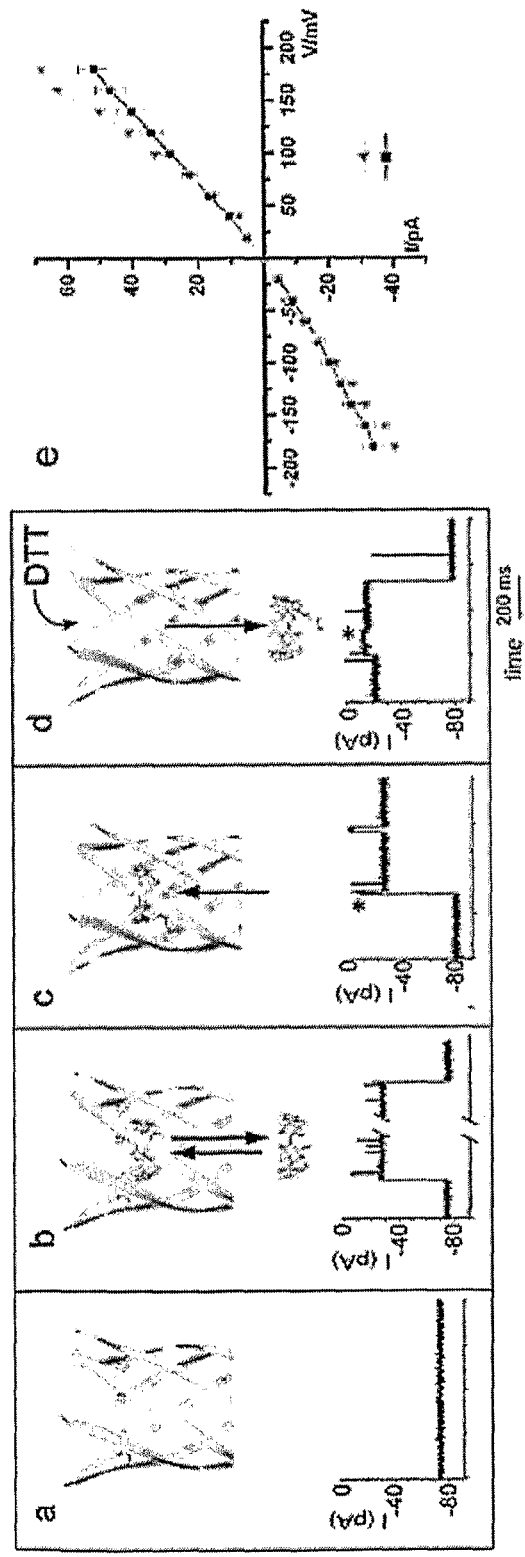
FIG. 5 shows a comparison of the properties of the non-covalent complex αHL (M113N-RL2)$_7$-βCD and the covalent adduct αHL (M113N-RL2)$_6$(T117C-D8RL3)$_1$-βCD. Each experiment was repeated at least 6 times. a) Cartoon representation of amino acids 108 to 120 of the mutant αHL pore (M113N-RL2)$_7$. Asn-113 residues are represented in stick form. Single-channel current trace from a (M113N-RL2)$_7$ pore in 25 mM Tris.HCl, pH 8.0, 1 M KCl, −100 mV. b) Cartoon representation of αHL (M113N-RL2)$_7$ with βCD bound as revealed by the X-ray structure of (M113N-RL2)$_7$•βCD. The arrows indicate that βCD is free to move in and out of the pore. The current trace shows an initially unoccupied pore followed by the binding of βCD and its subsequent dissociation (mean $\tau_{off}$=10.7±1.5 s). c) Cartoon representation of amino acids 108 to 120 of αHL (M113N-RL2)$_6$(T117C-D8RL3)$_1$. Asn-113 residues are represented in stick form and Cys-117 is colored in brown and also represented in sticks. An enlarged view of FIG. 5c can be found in FIG. 6. The arrow indicates that when βCD-PDP enters the pore the secondary hydroxyls interact with the side chains of Asn-113, and Cys-117 can react with the pyridyl disulfide of βCD-PDP to form a disulfide bond. The current trace shows the current amplitude change when the reaction takes place between Cys-117 and the pyridyl disulfide of βCD-PDP. The transient state with 80% current block is marked (*). d) Cleavage of (M113N-RL2)$_6$(T117C-D8RL3)$_1$-βCD with DTT. The arrow indicates that the cyclodextrin derivative detaches from position 117 after cleavage of the disulfide bond. The current trace shows the current amplitude changes during cleavage. The transient state with 90% current block is marked (*). e) Single-channel I-V curves for (M113N-RL2)$_7$•βCD (t) and αHL (M113N-RL2)$_6$(T117C-D8RL3)$_1$-βCD (□). Conditions: 25 mM Tris.HCl, pH 8.0, 1 M KCl.
Figure 6:
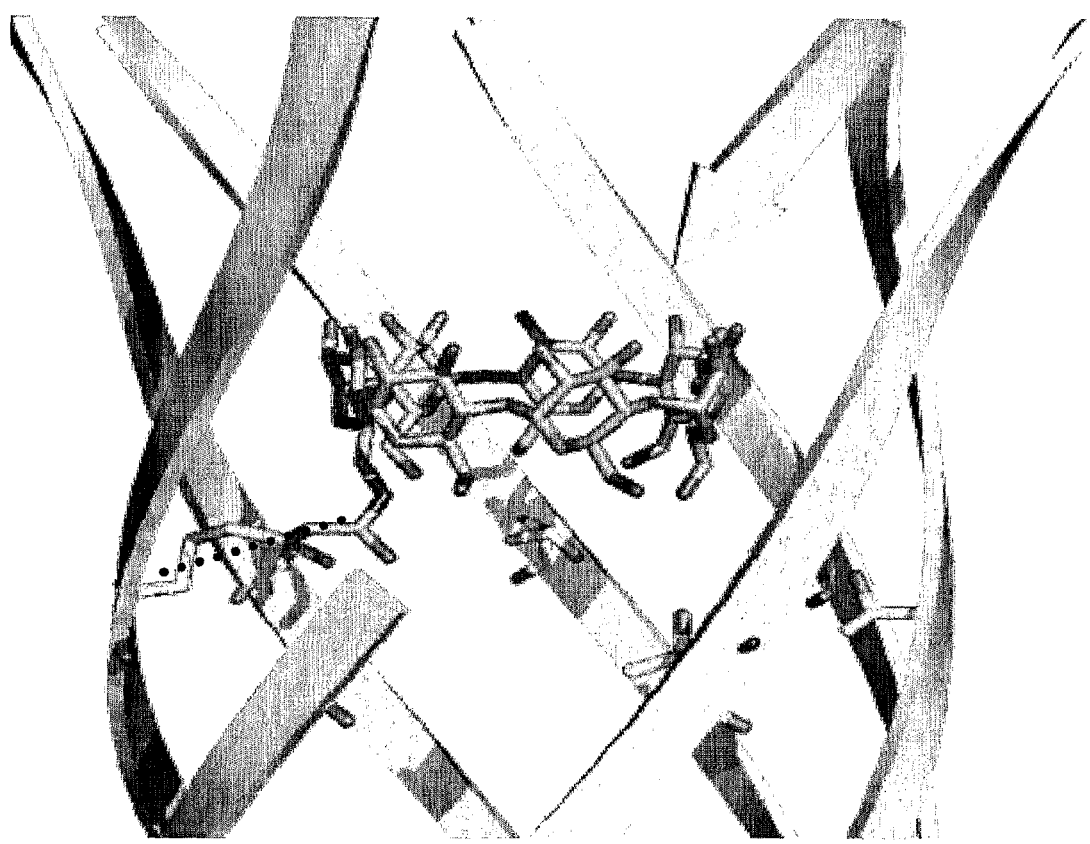
FIG. 6 shows an enlarged view of FIG. 5c. Cartoon representation of amino acids 108 to 120 of αHL (M113N-RL2)$_6$(T117C-D8RL3)$_1$. Asn-113 residues are represented in stick form and Cys-117 is colored in brown and also represented in sticks.

We portrayed the desired covalent complexes (M113F-RL2)$_6$(M113C-D8RL2)$_1$-βCD and (M113N-RL2)$_6$(T117C-D8RL3)$_1$-βCD in PyMOL. In (M113F-RL2)$_6$(M113C-D8RL2)$_1$-βCD, the distance between the amide N atom of am$_1$βCD and the S atom of the cysteine at position 113 is 5.6 Å (FIGS. 3c and 4). In (M113N-RL2)$_6$(T117C-D8RL3)$_1$-βCD, the distance between the amide N atom of am$_1$βCD and the S of cysteine at position 117 is 6.2 Å (FIGS. 5c and 6). These values are close to the corresponding measurements taken from the X-ray structures of the non-covalent complexes (see above) and confirm that the choice of the linker length is correct.

2.2 Electrical Characterization of (M113F-RL2)$_6$(M113C-D8RL2)$_1$-βCD

When a single (M113F-RL2)$_6$(M113C-D8RL2)$_1$ pore was introduced into the lipid bilayer from the cis chamber, we measured an ionic current of 98±5 pA (+100 mV, 25 mM Tris.HCl, pH 8.0, 1 M KCl, n=6). To observe the reaction with the pore, βCD-PDP was added to the trans chamber, and the potential was held at +100 mV. Two types of transient blocking events were observed, amounting to 70% and 95% of the total current. By contrast, when βCD interacts with (M113F-RL2)$_7$, only 70% current blockades are observed. Therefore, the 70% block is most likely generated when βCD-PDP binds within the pore with its primary hydroxyls interacting with the Phe-113 side chains and the linker protruding towards the cis side. The 95% block may occur when βCD-PDP enters the pore with the pyridyl ring lodged inside the cavity of the cyclodextrin, thereby reducing the current flow. Eventually, after a period ranging from 5 min to 1 h, the current level became permanently locked into a state of 70% block. This event was preceded by an 85% block that lasted for 48±7 ms (n=5) (FIGS. 3c and 4). No recovery of the current from the 70% blocked state to that of the unmodified pore was observed during a total recording period of 24 h (over 16 experiments). By comparison, the mean $\tau_{off}$ of βCD non-covalently bound to (M113F-RL2)$_7$ is 316±62 ms under the same conditions. The blocked state is presumed to represent the αHL pore with βCD covalently attached through a disulfide bond at position 113 (FIGS. 3c and 4). In keeping with this idea, the disulfide bond was cleaved after the addition of 2 mM DTT to the cis chamber. During cleavage a transient intermediate state with a lifetime of 150±12 ms (n=5) and 98% current block was observed (FIG. 3d). The 70% block in (M113F-RL2)$_6$(M113C-D8RL2)$_1$-βCD was also maintained after the applied potential was ramped up and down within the range of ±250 mV. It might be noted that the binding of neutral molecules such as βCD within the αHL pore is voltage-dependent, owing to the effects of electrosmosis (Gu, L.-Q., Cheley, S., and Bayley, H. (2003) *Proc. Natl. Acad. Sci. USA* 100, 15498-15503). Covalent binding therefore prevents βCD dissociation at potentials where the non-covalent complex is short-lived.

Current-voltage (I-V) curves were measured for (M113F-RL2)$_6$(M113C-D8RL2)$_1$-βCD and the non-covalent complex (M113F)$_7$•βCD. The I-V curves are not significantly different between +150 and −60 mV. However, when the applied potential is below −60 mV, the I-V curve for (M113F-RL2)$_6$(M113C-D8RL2)$_1$-βCD is more rectifying than that of (M113F-RL2)$_7$•βCD (FIG. 3e).

2.3 Electrical Characterization of (M113N-RL2)$_6$(T117C-D8RL3)$_1$

When a single (M113N-RL2)$_6$(T117C-D8RL3)$_1$ protein pore was introduced into the lipid bilayer from the cis chamber, we measured an ionic current of −80±5 pA (−100 mV, 25 mM Tris.HCl, pH 8.0, 1 M KCl, n=6). After βCD-PDP was added to the trans compartment, only one type of transient blocking event was observed with a 70% current block, which is close to the 65% block observed with (M113N-RL2)$_7$•βCD. After a period ranging from 1 to 20 min, an intermediate state with a lifetime of 5±2 ms (n=5) and 80% current block was observed, which was followed by a permanent 70% current block (FIGS. 4 and 5c). As in the case of (M113F-RL2)$_6$(M113C-D8RL2)$_1$-βCD, this 70% block was not reversed during a total of 24 h (over 16 experiments), while the mean $\tau_{off}$ for (M113N-RL2)$_7$•βCD is only 10.7±1.5 s under the same conditions. Again, the applied potential could be ramped up and down within the range of ±250 mV without unblocking the pore. Therefore, this state is presumed to represent the αHL pore with βCD covalently attached through a disulfide bond to position 117 (FIGS. 4 and 5c). Again, the disulfide bond was cleaved after the addition of 2 mM DTT to the cis chamber (FIG. 5d). During cleavage, a transient intermediate state with 80% current block and a lifetime of 300±20 ms (n=5) was observed (FIG. 5d).

Current-voltage (I-V) curves were measured for the adduct (M113N-RL2)$_6$(T117C-D8RL3)$_1$-βCD. The I-V curve of this complex is similar to that of (M113N-RL2)$_7$•βCD within the range of ±100 mV, diverging slightly at both high positive and negative potentials (FIG. 5e).

2.4 Attempts to Link βCD in Reverse Orientations

To further investigate and confirm the proposed orientation of the covalently-attached βCD, we prepared the heteroheptamers (M113N-RL2)$_6$(M113C-D8RL3)$_1$ and (M113F-RL2)$_6$(T117C-D8RL2)$_1$, where covalent bond formation between βCD-PDP and the protein would in each case produce an orientation of the cyclodextrin opposite to that which the 113 mutations would normally support, as evidenced in the X-ray structures (FIG. 1).

In the case of (M113N-RL2)$_6$(M113C-D8RL2)$_1$, covalent attachment of βCD-PDP to Cys-113 failed to occur after ten attempts of 30 min each. By contrast, the heteroheptamer (M113F-RL2)$_6$(T117C-D8RL3)$_1$ did react with βCD-PDP as indicated by a permanent 80% current block. Like the two cases described earlier, the attached βCD resisted potential ramps of ±250 mV and could be detached by the addition of 2 mM DTT to the cis chamber (not shown). The presumed covalent adduct, (M113F-RL2)$_6$(T117C-D8RL3)$_1$-βCD, was examined by electrical recording in 25 mM Tris.HCl, pH 8.0, 1 M KCl, at ±100 mV (n=3). The single-channel current (24.0 pA) was lower than that of (M113N-RL2)$_6$(T117C-D8RL3)$_1$-βCD (40.0 pA) and displayed frequent full blockades at both positive and negative potentials (data not shown). In addition, the current passed by (M113F-RL2)$_6$(T117C-D8RL3)$_1$-βCD was far noisier than that observed with (M113N-RL2)$_6$(T117C-D8RL3)$_1$-βCD, precluding its use for the stochastic sensing of organic analytes (see below).

Figure 7:
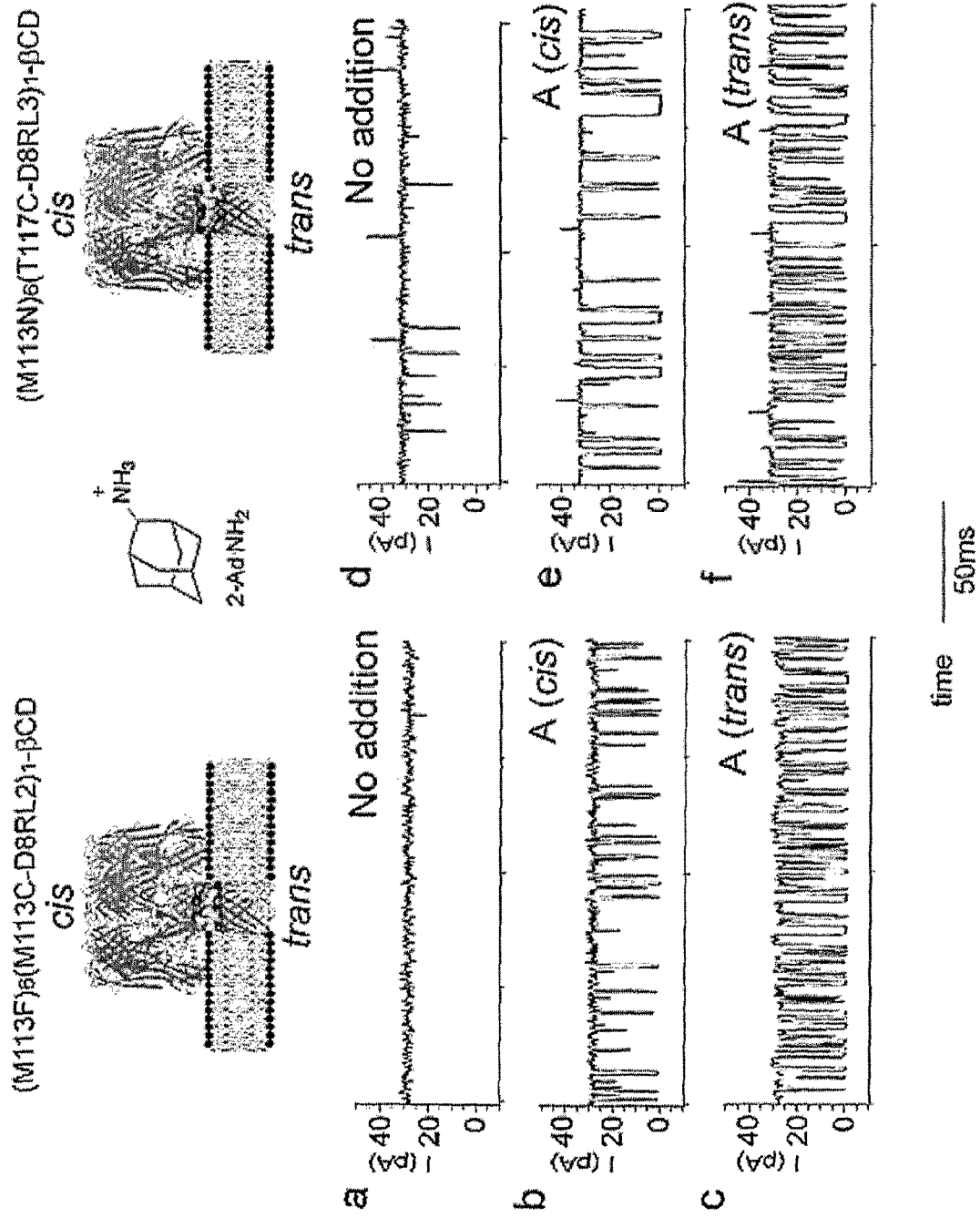
FIG. 7 shows the detection of 2-adamantanamine with αHL pores containing a covalently-attached βCD. a) Current trace from a single (M113F-RL2)$_6$(M113C-D8RL2)$_1$-βCD pore in 25 mM Tris.HCl, pH 8.0, 1 M KCl, at +100 mV. b) Current trace in the presence of 30 µM 2-adamantanamine in the cis chamber. c) Current trace with 30 µM 2-adamantanamine in the trans chamber. d) Current trace from a single (M113N-RL2)$_6$(T117C-D8RL3)-1-βCD pore in 25 mM Tris.HCl, pH 8.0, 1 M KCl, at +100 mV. e) Current trace with 30 µM 2-adamantanamine in the cis chamber. f) Current trace with 30 µM 2-adamantanamine in the trans chamber.

2.5 Analyte Detection Using Engineered αHL Pores with Covalently-Attached βCD Adaptors To evaluate the newly created constructs as biosensor detection elements, we carried out stochastic sensing of 2-adamantanamine (2-AdNH$_2$), a model analyte (12,15). The βCD adaptor was attached to (M113F-RL2)$_6$(M113C-D8RL2)$_1$ or (M113N-RL2)$_6$(T117C-D8RL3)$_1$ in situ as described above. 2-Adamantanamine.HCl was then added to either the cis or trans chamber and the transient current substrates were observed (FIG. 7). These events represent the formation and dissociation of individual 2-AdNH$_2$•βCD complexes within the engineered αHL pore. The mean dwell times (T$_{off}$) were similar to those observed when 2-AdNH$_2$ was added to the non-covalent complexes (M113F-RL2)$_7$•βCD and (M113N-RL2)$_7$•βCD (Table 5 below). The small differences in $\tau_{off}$ probably arise from interference by the linker.

TABLE 5

Stochastic sensing of 2-adamantanamine (2-AdNH$_2$) with covalent and non-covalent adducts of βCD and αHL

| Construct | $\tau_{off}$ ± SD (ms) | |
|---|---|---|
| | 2-AdNH$_2$ (cis) | 2-AdNH$_2$ (trans) |
| (M113F-RL2)$_6$(M113C-D8RL2)$_1$-βCD | 0.70 ± 0.11 (n = 7) | 0.99 ± 0.05 (n = 9) |
| (M113F-RL2)$_7$•βCD | 1.20 ± 0.08 (n = 6) | 1.25 ± 0.07 (n = 6) |
| (M113N-RL2)$_6$(T117C-D8RL3)$_1$-βCD | 1.15 ± 0.09 (n = 7) | 1.16 ± 0.07 (n = 9) |
| (M113N-RL2)$_7$•βCD | 1.12 ± 0.06 (n = 6) | 1.56 ± 0.08 (n = 8) |

Conditions: 25 mM Tris•HCl, pH 8.0, 1 M KCl, +100 mV, with 2-AdNH$_2$•HCl (cis or trans) at 30 μM. The number of individual experiments is in parentheses.

Figure 8:
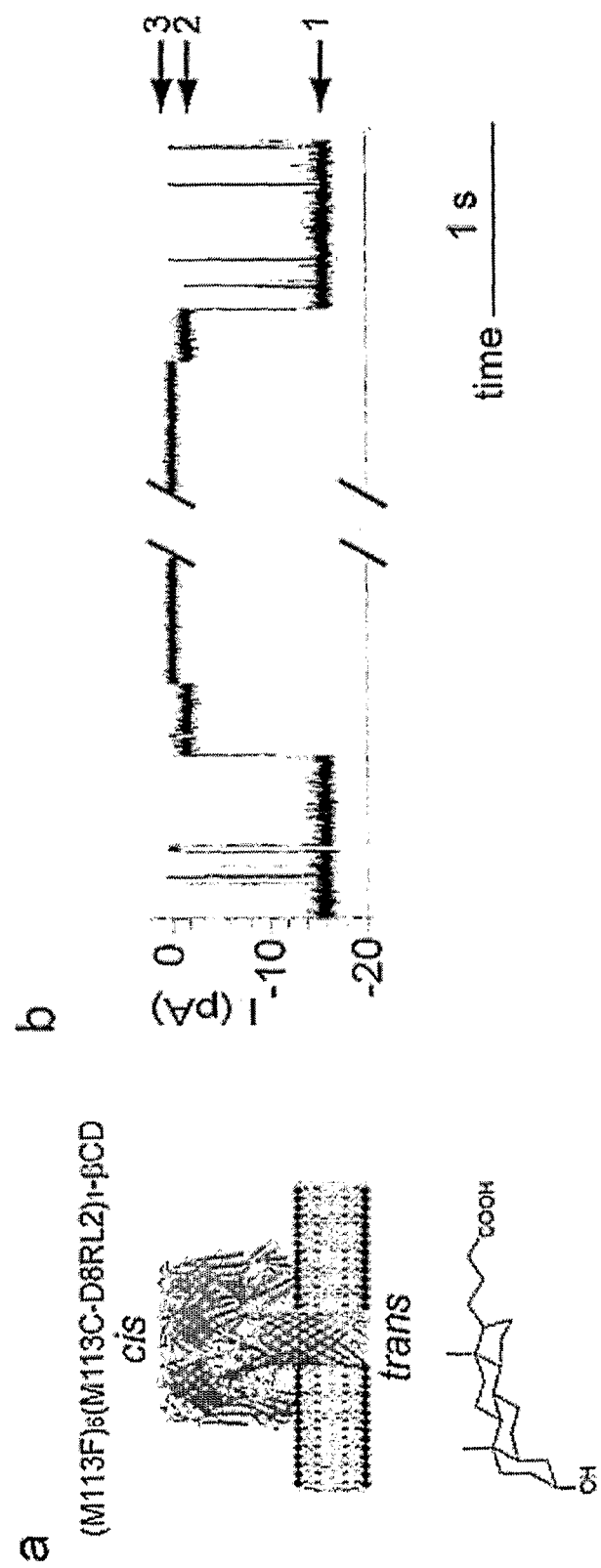
FIG. 8 shows long binding events of cis-lithocholic acid with (M113F-RL2)$_6$(M113C-D8RL2)$_1$-βCD. a) αHL with attached molecular adaptor (M113F-RL2)$_6$(M113C-D8RL2)$_1$-βCD and structure of cis-lithocholic acid. b) Characteristic binding event of cis-lithocholic acid (50 µM) with (M113F-RL2)$_6$(M113C-D8RL2)$_1$-βCD in 25 mM Tris.HCl, pH 8.0, 1 M KCl, at −100 mV. Mean $\tau_{off}$=8.6±7.8 s (number of events=60). Level 1: (M113F-RL2)$_6$(M113C-D8RL2)$_1$-βCD; level 2: (M113F-RL2)$_6$(M113C-D8RL2)$_1$-βCD•lithocholate, 92% block; level 3: (M113F-RL2)$_6$(M113C-D8RL2)-1-βCD•lithocholate, 98% block.
Figure 9:
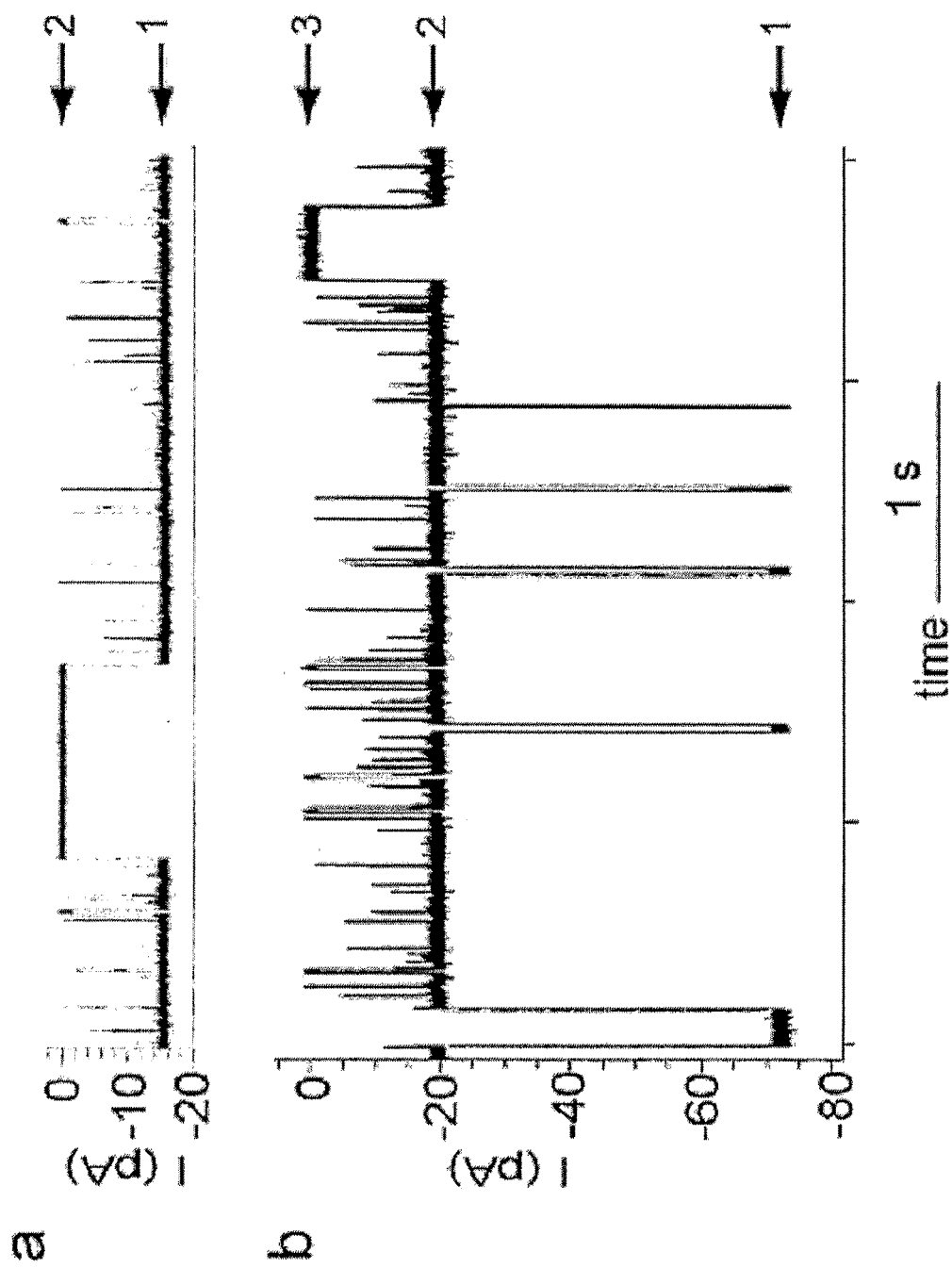
FIG. 9 shows that both (M113F-RL2)$_6$(M113C-D8RL2)$_1$-βCD and (M113F-RL2)$_7$ in the presence of 50 µM PCD show closures in the absence of cis-lithocholate that might be confused with cis-lithocholate binding, but the events are shorter. a) (M113F-RL2)$_6$(M113C-D8RL2)$_1$•βCD in the absence of cis-lithocholic acid under the same conditions as in FIG. 6. Level 1: (M113F-RL2)$_6$(M113C-D8RL2)$_1$-βCD; level 2: spontaneous gating of the pore. The events varied in duration from 30 to 300 ms. b) (M113F-RL2)$_7$ in the presence of 50 µM βCD in 25 mM Tris.HCl, 1 M KCl, at −100 mV.

2.6 Examination of Long Binding Events Using αHL Pores with Covalently-Attached Adaptors With covalently-attached adaptors it is possible to study the kinetics of two types of events that are more difficult to examine with non-covalently attached adaptors: long-lived and rare events. Cis-Lithocholic acid is the tightest binding molecule known for βCD (Yang, Z., and Breslow, R. (1997) *Tetrahedron Lett.* 38, 6171-6172). Therefore, we chose this molecule to test the newly constructed pores for studying binding events of long duration. (M113F-RL2)$_6$(M113C-D8RL2)$_1$•βCD was selected because of its quieter background signal in the absence of analyte (see FIG. 7, for example). When cis-lithocholic acid (50 μM, FIG. 8*a*) was introduced into the cis chamber in 25 mM Tris.HCl, pH 8.0, 1 M KCl, at +100 mV (n=3), surprisingly, no signal was observed. This is perhaps due to steric hindrance to binding to the cis side of (M113F-RL2)$_6$(M113C-D8RL2)$_1$•βCD by the linker that attaches the PCD to the barrel wall. When cis-lithocholic acid (50 μM) was introduced into the trans chamber at −100 mV (n=3), we observed many very long events. The events showed a 98% current block, with a 92% block for 200±100 ms at the beginning of each event and for 150±100 ms at the end of the event (FIG. 8*b*, FIG. 9). The mean $\tau_{off}$ of the events was 8.6±7.8 s (number of events=60; range 0.5 s to 80 s), which is considerably longer than the $\tau_{off}$ (0.68±0.12 s) for βCD in the (M113F-RL2)$_7$•βCD complex under the same conditions, i.e. βCD would most often dissociate from the non-covalent (M113F-RL2)$_7$•βCD during a lithocholic acid binding event. This shows the advantage of the covalently-attached adaptor over the non-covalent complexes for examining long-lived binding events.

2.7 αHL Pores with Covalently-Attached Adaptors at High Temperatures

We speculated that αHL pores with covalently attached CDs might work better than underivatized pores at high temperatures when the dwell time of CDs is reduced (Kang, X., Gu, L.-Q., Cheley, S., and Bayley, H. (2005) *Angew. Chem. Int. Ed. Engl.*, 1495-1499). Single-channel current traces of (M113F)$_6$(M113C-D8RL2)$_1$-βCD were obtained at up to 55° C. The single-channel currents depended linearly on the temperature (FIG. 10). I (pA)=14.3+0.54T(° C.) in 25 mM Tris.HCl, pH 8.0, 1 M KCl at +100 mV, which is a similar temperature dependence to that observed previously with an αHL pore with non-covalently bound βCD (Kang, X., Gu, L.-Q., Cheley, S., and Bayley, H. (2005) *Angew. Chem. Int. Ed. Engl.*, 1495-1499). No dissociation of βCD from the (M113F-RL2)$_6$(M113C-D8RL2)$_1$-βCD pore was observed during these experiments. For example, the current passed by (M113F-RL2)$_6$(M113C-D8RL2)$_1$-βCD remained constant at 55° C. during a 5 min measurement, while the $\tau_{off}$ for βCD bound to (M113F-RL2)$_6$(M113C-D8RL2)$_1$ was only 56±3.8 ms under the same conditions. These data show that αHL pores with covalently attached CDs permit stochastic sensing in aqueous solution under extreme conditions.

2.8 Permanent Alteration of Ion Selectivity in αHL Pores with Covalently-Attached Adaptors Non-covalent molecular adaptors lodged within the αHL pore can drastically alter the charge selectivity for ion transport (Gu, L.-Q., Dalla Serra, M., Vincent, J. B., Vigh, G., Cheley, S., Braha, O., and Bayley, H. (2000) *Proc. Natl. Acad. Sci. USA* 97, 3959-3964). For example, at pH 7.5, the charge selectivity ($P_{K^+}/P_{Cl^-}$, KCl: c is 200 mM, trans 1000 mM) of WT-αHL changes from 0.55±0.02 to 0.25±0.01 after βCD becomes lodged in the lumen, i.e. the pore becomes more anion selective (Gu, L.-Q., Dalla Serra, M., Vincent, J. B., Vigh, G., Cheley, S., Braha, O., and Bayley, H. (2000) *Proc. Natl. Acad. Sci. USA* 97, 3959-3964). Therefore, we expected that βCD, covalently attached inside the β barrel, would alter the ion selectivity of an αHL pore permanently. We took (M113F-RL2)$_6$(M113C-D8RL2)$_1$ and (M113F-RL2)$_6$(M113C-D8RL2)$_1$-βCD as a test case and constructed I-V curves for single-channel currents recorded under both cis/trans and trans/cis KCl gradients (FIG. 11). The measured conductance values (g) and reversal potentials (Vr), and the charge selectivity ($P_{K^+}/P_{Cl^-}$) calculated from the Goldman-Hodgkin-Katz equation (Hille, B. (2001) *Ion channels of excitable membranes, 3rd edition.*, Sinauer, Sunderland, Mass., USA), of both the underivatized and derivatized pores are shown in Table 6 (below).

TABLE 6

Reversal potentials (Vr), calculated charge selectivities ($P_{K^+}/P_{Cl^-}$) and conductance values (g) of (M113F-RL2)$_{6(M113C-D8RL2)_1}$ and (M113F-RL2)$_6$(M113C-D8RL2)$_1$-βCD

| Pore | Buffer* | Vr (mV) | $P_{K^+}/P_{Cl^-}$ | g (PS)[†] |
|---|---|---|---|---|
| (M113F-RL2)$_6$(M113C-D8RL2)$_1$ | cis 200/ trans 1000 | 11.4 ± 0.1 | 0.47 ± 0.01 | 973 ± 10 |
| | cis 1000/ trans 200 | −5.0 ± 0.1 | 0.73 ± 0.02 | |
| (M113F-RL2)$_6$(M113C-D8RL2)$_1$-βCD | cis 200/ trans 1000 | 28.3 ± 0.2 | 0.10 ± 0.01 | 295 ± 5 |
| | cis 1000/ trans 200 | −26.0 ± 0.2 | 0.14 ± 0.01 | |

For each entry, three separate experiments were performed. The reversal potentials (Vr) are mean values (n = 3) under the conditions stated. Charge selectivities ($P_{K^+}/P_{Cl^-}$, n = 3) and conductance values (n = 3) are quoted as the mean ± SD.
$P_{K^+}/P_{Cl^-}$ was calculated with the Goldman-Hodgkin-Katz equation by using activities and the experimental $V_{r\ value}$ (20).
*25 mM Tris•HCl, pH 8.0. The salt concentrations (KCl) are given in mM.
[†]+100 mV, 1 M KCl, 25 mM Tris•HCl, pH 8.0, in both chambers.

The covalently-attached molecular adaptor indeed altered the charge selectivity of the αHL pore and this effect was permanent. Again the pore becomes more anion selective and the observed changes in $P_{K^+}/P_{Cl^-}$ are similar to those seen with non-covalently bound βCD (Gu, L.-Q., Dalla Serra, M., Vincent, J. B., Vigh, G., Cheley, S., Braha, O., and Bayley, H. (2000) *Proc. Natl. Acad. Sci. USA* 97, 3959-3964). This feature should be useful in the de novo design of membrane channels both for basic studies of ion permeation and for applications in biotechnology, where a varied assemblage of pores with modified properties would be of great utility (Hwang, W. L., Holden, M. A., White, S., and Bayley, H. (2007) submitted for publication; and Holden, M. A., Needham, D., and Bayley, H. (2007) *J Am Chem Soc*, in press).

3. CONCLUSION

Engineering of the αHL pore to allow the binding of organic analytes for stochastic detection has been successful only rarely (Guan, X., Gu, L.-Q., Cheley, S., Braha, O., and Bayley, H. (2005) *ChemBioChem* 6, 1875-1881), but non-covalent molecular adaptors have proved useful in this regard, despite certain limitations imposed by their continual association with and dissociation from the pore. To remedy the latter problem, we have now covalently attached the βCD adaptor inside the αHL pore. Further, the attachment has been performed with control over the orientation of the βCD, i.e. with the primary hydroxyls of the βCD facing either the trans or the cis entrance of the pore. Covalent attachment means that there are no gaps in detection, and control over the βCD orientation is important because it is likely that certain analytes bind through only one of the two entrances to the βCD cavity or that they bind in different ways depending upon the side of entry (Kang, X. F., Cheley, S., Guan, X., and Bayley, H. (2006) *J Am Chem Soc* 128(33), 10684-10685). To exemplify the utility of αHL pores with covalently-attached βCD in stochastic sensing, we show here that the pores can be used to detect analytes with long dwell times within βCD. In this case, the βCD would normally dissociate from the pore before the analyte dissociates from the βCD, degrading the information content of the signal (Braha, O., Webb, J., Gu, L.-Q., Kim, K., and Bayley, H. (2005) *ChemPhysChem* 6, 889-892). The effects of continual CD association and dissociation are exacerbated at high temperatures (Kang, X., Gu, L.-Q., Cheley, S., and Bayley, H. (2005) *Angew. Chem. Int. Ed. Engl.*, 1495-1499), and as demonstrated here covalent attachment also remedies this problem. We also show that αHL pores with covalently-attached βCD can have permanently altered ion selectivity, which might be useful, for example, for building nanobatteries (Hwang, W. L., Holden, M. A., White, S., and Bayley, H. (2007) submitted for publication; and Holden, M. A., Needham, D., and Bayley, H. (2007) *J Am Chem Soc*, in press).

Single molecule DNA sequencing (Bayley, H. (2006) *Curr Opin Chem Biol* 10, 628-637) will also benefit from the use of protein nanopores containing covalently attached βCDs. In one approach, deoxyribonucleoside 5'-monophosphates are released from an individual DNA strand by a processive exonuclease (Jett, J. H., Keller, R. A., Martin, J. C., Marrone, B. L., Moyzis, R. K., Ratliff, R. L., Seitzinger, N. K., Shera, E. B., and Stewart, C. C. (1989) *J. Biomol. Struct. Dynam.* 7, 301-309). In the original manifestation, fluorescent base analogs would be released from a fully-substituted transcribed DNA strand, which has proved very difficult to implement. However, we have recently shown that the four deoxyribonucleoside 5'-monophosphates can be distinguished by using the non-covalent αHL (M113R-RL2)$_7$•am$_7$βCD complex, where am$_7$βCD is heptakis-(6-deoxy-6-amino)-β-cyclodextrin (Astier, Y., Braha, O., and Bayley, H. (2006) *J Am Chem Soc* 128(5), 1705-1710). While this is a step forward, for successful sequencing, every base released by an exonuclease must be captured by the detection element and identified. Therefore if the αHL pore with a molecular adaptor is to be used, the adaptor being covalently attached will help to avoid gaps in sequencing.

Tables 7 to 16 below set out the sequence information

TABLE 7

SEQ ID NOs: 1 and 2 - Wild-type α-hemolysin from *Staphylococcus aureus*
SEQ ID NO: 2 is encoded by residues 1 to 879 of SEQ ID NO: 1

| | | | | | |
|---|---|---|---|---|---|
| gcagattctg | atattaatat | taaaaccggt | actacagata | ttggaagcaa | tactacagta | 60 |
| aaaacaggtg | atttagtcac | ttatgataaa | gaaaatggca | tgcacaaaaa | agtattttat | 120 |
| agttttatcg | atgataaaaa | tcacaataaa | aaactgctag | ttattagaac | gaaaggtacc | 180 |
| attgctggtc | aatatagagt | ttatagcgaa | gaaggtgcta | acaaaagtgg | tttagcctgg | 240 |
| ccttcagcct | taaggtac | agttgcaacta | cctgataatg | aagtagctca | aatatctgat | 300 |
| tactatccaa | gaaattcgat | tgatacaaaa | gagtatatga | gtactttaac | ttatggattc | 360 |
| aacggtaatg | ttactggtga | tgatacagga | aaaattggcg | gccttattgg | tgcaaatgtt | 420 |
| tcgattggtc | atacactgaa | atatgttcaa | cctgatttca | aaacaatttt | agagagccca | 480 |
| actgataaaa | aagtaggctg | gaaagtgata | tttaacaata | tggtgaatca | aaattgggga | 540 |
| ccatatgata | gagattcttg | gaacccggta | tatggcaatc | aacttttcat | gaaaactaga | 600 |
| aatggttcta | tgaaagcagc | agataacttc | cttgatcctaa | caaagcaag | ttctctatta | 660 |
| tcttcagggt | tttcaccaga | cttcgctaca | gttattacta | tggatagaaa | agcatccaaa | 720 |
| caacaaacaa | atatagatgt | aatatacgaa | cgagttcgtg | atgattacca | attgcattgg | 780 |
| acttcaacaa | attggaaagg | taccaatact | aaagataaat | ggacagatcg | ttcttcagaa | 840 |
| agatataaaa | tcgattggga | aaaagaagaa | atgacaaatt | aa | | 882 |
| ADSDINIKTG | TTDIGSNTTV | KTGDLVTYDK | ENGMHKKVFY | SFIDDKNHNK | KLLVIRTKGT | 60 |
| IAGQYRVYSE | EGANKSGLAW | PSAFKVQLQL | PDNEVAQISD | YYPRNSIDTK | EYMSTLTYGF | 120 |
| NGNVTGDDTG | KIGGLIGANV | SIGHTLKYVQ | PDFKTILESP | TDKKVGWKVI | FNNMVNQNWG | 180 |
| PYDRDSWNPV | YGNQLFMKTR | NGSMKAADNF | LDPNKASSLL | SSGFSPDFAT | VITMDRKASK | 240 |
| QQTNIDVIYE | RVRDDYQLHW | TSTNWKGTNT | KDKWTDRSSE | RYKIDWEKEE | MTN | 293 |

TABLE 8

SEQ ID NOs: 3 and 4 - α-hemolysin M113H-RL2
SEQ ID NO: 4 is encoded by residues 39 to 920 of SEQ ID NO: 3
n = a, c, g or t
X at location 5 stands for Leu or Phe
X at location 7 stands for Tyr, Trp, Cys, Ser, Leu or Phe

| | |
|---|---:|
| gttctgttta actttaagaa gggagatata catatgagca gattctgata ttnacntnng | 60 |
| cgaccggtac tacagatatt ggaagcaata ctacagtaaa acaggtgat ttagtcactt | 120 |
| atgataaaga aaatggcatg cacaaaaaag tattttatag ttttatcgat gataaaaatc | 180 |
| acaataaaaa actgctagtt attagaacaa aaggtaccat tgctggtcaa tatagagttt | 240 |
| atagcgaaga aggtgctaac aaaagtggtt tagcctggcc ttcagccttt aaggtacagt | 300 |
| tgcaactacc tgataatgaa gtagctcaaa tatctgatta ctatccgcgg aattcgattg | 360 |
| atacaaaaga gtatcacagt acgttaacgt acggattcaa cggtaaccct actggtgatg | 420 |
| atactagtaa aattggaggc cttattgggg cccaggtttc cctaggtcat acacttaagt | 480 |
| atgttcaacc tgatttcaaa acaattctcg agagcccaac tgataaaaaa gtaggctgga | 540 |
| aagtgatatt taacaatatg gtgaatcaaa attggggacc atacgatcga gattcttgga | 600 |
| acccggtata tggcaatcaa cttttcatga agactagaaa tggttctatg aaagcagcag | 660 |
| ataacttcct tgatcctaac aaagcaagtt ccctattatc ttcagggttt tcaccagact | 720 |
| tcgctacagt tattactatg gatagaaaag catccaaaca acaaacaaat atagatgtaa | 780 |
| tatacgaacg agttcgtgat gattaccaat tgcattggac ttcaccaaat tggaaaggta | 840 |
| ccaatactaa agataaatgg acagatcgtt cttcagaaag atataaaatc gattgggaaa | 900 |
| aagaagaaat gacaaattaa tgtaanttat ttgtacatgt acaataaat ataatttata | 960 |
| actttagccg aagctggatc cggctgctac naancccnaa ngnagctgan ttgnctgctg | 1020 |
| cccccctgac natactagca naccccttgg gnccctaacg ggtctgnggg gtttttgctg | 1080 |
| aangngnact tttccgnnan tcnncccggn cccccncggt gaaatccnaa ncccnaacn | 1140 |
| ggngntgnta ncaantttan tggnncntna ntttnnaaan cnnntaantt ngnaancccc | 1200 |
| nttttncnan ggcnaannnn nanccttttna naaaaaancc nnnggggggg tttcnntnnn | 1260 |
| annncnttn aangggcccc cnngggggnaa nnntnggggn | 1300 |
| QILIXTXATG TTDIGSNTTV KTGDLVTYDK ENGMHKKVFY SFIDDKNHNK KLLVIRTKGT | 60 |
| IAGQYRVYSE EGANKSGLAW PSAFKVQLQL PDNEVAQISD YYPRNSIDTK EYHSTLTYGF | 120 |
| NGNLTGDDTS KIGGLIGAQV SLGHTLKYVQ PDFKTILESP TDKKVGWKVI FNNMVNQNWG | 180 |
| PYDRDSWNPV YGNQLFMKTR NGSMKAADNF LDPNKASSLL SSGFSPDFAT VITMDRKASK | 240 |
| QQTNIDVIYE RVRDDYQLHW TSPNWKGTNT KDKWTDRSSE RYKIDWEKEE MTN | 293 |

TABLE 9

SEQ ID NOs: 5 and 6 - α-hemolysin M113K-RL2
SEQ ID NO: 6 is encoded by residues 39 to 920 of SEQ ID NO: 5
n = a, c, g or t
X at location 5 stands for Leu or Phe
X at location 7 stands for Tyr, Trp, Cys, Ser, Leu or Phe

| | |
|---|---:|
| gttctgttta actttaagaa gggagatata catatgagca gattctgata ttnacntnng | 60 |
| cgaccggtac tacagatatt ggaagcaata ctacagtaaa acaggtgat ttagtcactt | 120 |
| atgataaaga aaatggcatg cacaaaaaag tattttatag ttttatcgat gataaaaatc | 180 |
| acaataaaaa actgctagtt attagaacaa aaggtaccat tgctggtcaa tatagagttt | 240 |
| atagcgaaga aggtgctaac aaaagtggtt tagcctggcc ttcagccttt aaggtacagt | 300 |

TABLE 9-continued

SEQ ID NOs: 5 and 6 - α-hemolysin M113K-RL2
SEQ ID NO: 6 is encoded by residues 39 to 920 of SEQ ID NO: 5
n = a, c, g or t
X at location 5 stands for Leu or Phe
X at location 7 stands for Tyr, Trp, Cys, Ser, Leu or Phe

| | |
|---|---:|
| tgcaactacc tgataatgaa gtagctcaaa tatctgatta ctatccgcgg aattcgattg | 360 |
| atacaaaaga gtataaaagt acgttaacgt acggattcaa cggtaacctt actggtgatg | 420 |
| atactagtaa aattggaggc cttattgggg cccaggtttc cctaggtcat acacttaagt | 480 |
| atgttcaacc tgatttcaaa acaattctcg agagcccaac tgataaaaaa gtaggctgga | 540 |
| aagtgatatt taacaatatg gtgaatcaaa attggggacc atacgatcga gattcttgga | 600 |
| acccggtata tggcaatcaa cttttcatga agactagaaa tggttctatg aaagcagcag | 660 |
| ataacttcct tgatcctaac aaagcaagtt ccctattatc ttcagggttt tcaccagact | 720 |
| tcgctacagt tattactatg gatagaaaag catccaaaca acaaacaaat atagatgtaa | 780 |
| tatacgaacg agttcgtgat gattaccaat tgcattggac ttcaccaaat tggaaaggta | 840 |
| ccaatactaa agataaatgg acagatcgtt cttcagaaag atataaaatc gattgggaaa | 900 |
| aagaagaaat gacaaaattaa tgtaanttat ttgtacatgt acaaataaat ataatttata | 960 |
| actttagccg aagctggatc cggctgctac naancccnaa ngnagctgan ttgnctgctg | 1020 |
| cccccctgac natactagca naccccttgg gncctaacg ggtctgnggg gttttgctg | 1080 |
| aangngnact tttccgnnan tcnncccggn ccccccnggt gaaatccnaa nccccnaacn | 1140 |
| ggngntgnta ncaantttan tggnncntna ntttnnaaan cnnntaantt ngnaaccccc | 1200 |
| nttttncnan ggcnaannnn nanccttttna naaaaaancc nnnggggggg tttcnntnnn | 1260 |
| annncnttn aangggcccc cnnggggnaa nnntngggn | 1300 |
| QILIXTXATG TTDIGSNTTV KTGDLVTYDK ENGMHKKVFY SFIDDKNHNK KLLVIRTKGT | 60 |
| IAGQYRVYSE EGANKSGLAW PSAFKVQLQL PDNEVAQISD YYPRNSIDTK EYKSTLTYGF | 120 |
| NGNLTGDDTS KIGGLIGAQV SLGHTLKYVQ PDFKTILESP TDKKVGWKVI FNNMVNQNWG | 180 |
| PYDRDSWNPV YGNQLFMKTR NGSMKAADNF LDPNKASSLL SSGFSPDFAT VITMDRKASK | 240 |
| QQTNIDVIYE RVRDDYQLHW TSPNWKGTNT KDKWTDRSSE RYKIDWEKEE MTN | 293 |

TABLE 10

SEQ ID NOs: 7 and 8 - α-hemolysin M113R-RL2
SEQ ID NO: 8 is encoded by residues 39 to 920 of SEQ ID NO: 7
n = a, c, g or t
X at location 5 stands for Leu or Phe
X at location 7 stands for Tyr, Trp, Cys, Ser, Leu or Phe

| | |
|---|---:|
| gttctgttta actttaagaa gggagatata catatgagca gattctgata ttnacntnng | 60 |
| cgaccggtac tacagatatt ggaagcaata ctacagtaaa aacaggtgat ttagtcactt | 120 |
| atgataaaga aaatggcatg cacaaaaaag tattttatag ttttatcgat gataaaaatc | 180 |
| acaataaaaa actgctagtt attagaacaa aaggtaccat tgctggtcaa tatagagttt | 240 |
| atagcgaaga aggtgctaac aaaagtggtt tagcctggcc ttcagccttt aaggtacagt | 300 |
| tgcaactacc tgataatgaa gtagctcaaa tatctgatta ctatccgcgg aattcgattg | 360 |
| atacaaaaga gtatagaagt acgttaacgt acggattcaa cggtaacctt actggtgatg | 420 |
| atactagtaa aattggaggc cttattgggg cccaggtttc cctaggtcat acacttaagt | 480 |
| atgttcaacc tgatttcaaa acaattctcg agagcccaac tgataaaaaa gtaggctgga | 540 |

TABLE 10-continued

SEQ ID NOs: 7 and 8 - α-hemolysin M113R-RL2
SEQ ID NO: 8 is encoded by residues 39 to 920 of SEQ ID NO: 7
n = a, c, g or t
X at location 5 stands for Leu or Phe
X at location 7 stands for Tyr, Trp, Cys, Ser, Leu or Phe

| | |
|---|---|
| aagtgatatt taacaatatg gtgaatcaaa attggggacc atacgatcga gattcttgga | 600 |
| acccggtata tggcaatcaa cttttcatga agactagaaa tggttctatg aaagcagcag | 660 |
| ataacttcct tgatcctaac aaagcaagtt ccctattatc ttcagggttt tcaccagact | 720 |
| tcgctacagt tattactatg gatagaaaag catccaaaca acaaacaaat atagatgtaa | 780 |
| tatacgaacg agttcgtgat gattaccaat tgcattggac ttcaccaaat tggaaaggta | 840 |
| ccaatactaa agataaatgg acagatcgtt cttcagaaag atataaaatc gattgggaaa | 900 |
| aagaagaaat gacaaattaa tgtaatttat ttgtacatgt acaaataaat ataatttata | 960 |
| actttagccg aagctggatc cggctgctac naanccccnaa ngnagctgan ttgnctgctg | 1020 |
| cccccctgac natactagca naccccttgg gnccctaacg ggtctgnggg gtttttgctg | 1080 |
| aangngnact tttccgnnan tcnncccggn cccccccnggt gaaatccnaa ncccnaacn | 1140 |
| ggngntgnta ncaantttan tggnncntna ntttnnaaan cnnntaantt ngnaancccc | 1200 |
| nttttncnan ggcnaannnn nancctttna naaaaaancc nnnggggggg tttcnntnnn | 1260 |
| annnccnttn aangggcccc cnnggggnaa nnntngggn | 1300 |
| QILIXTXATG TTDIGSNTTV KTGDLVTYDK ENGMHKKVFY SFIDDKNHNK KLLVIRTKGT | 60 |
| IAGQYRVYSE EGANKSGLAW PSAFKVQLQL PDNEVAQISD YYPRNSIDTK EYRSTLTYGF | 120 |
| NGNLTGDDTS KIGGLIGAQV SLGHTLKYVQ PDFKTILESP TDKKVGWKVI FNNMVNQNWG | 180 |
| PYDRDSWNPV YGNQLFMKTR NGSMKAADNF LDPNKASSLL SSGFSPDFAT VITMDRKASK | 240 |
| QQTNIDVIYE RVRDDYQLHW TSPNWKGTNT KDKWTDRSSE RYKIDWEKEE MTN | 293 |

TABLE 11

SEQ ID NOs: 9 and 10 - α-hemolysin M113F-RL2
SEQ ID NO: 10 is encoded by residues 39 to 920 of SEQ ID NO: 9
n = a, c, g or t
X at location 5 stands for Leu or Phe
X at location 7 stands for Tyr, Trp, Cys, Ser, Leu or Phe

| | |
|---|---|
| gttctgttta actttaagaa gggagatata catatgagca gattctgata ttnacntnng | 60 |
| cgaccggtac tacagatatt ggaagcaata ctacagtaaa aacaggtgat ttagtcactt | 120 |
| atgataaaga aaatggcatg cacaaaaaag tattttatag ttttatcgat gataaaaatc | 180 |
| acaataaaaa actgctagtt attagaacaa aaggtaccat tgctggtcaa tatagagttt | 240 |
| atagcgaaga aggtgctaac aaaagtggtt tagcctggcc ttcagccttt aaggtacagt | 300 |
| tgcaactacc tgataatgaa gtagctcaaa tatctgatta ctatccgcgg aattcgattg | 360 |
| atacaaaaga gtatttcagt acgttaacgt acggattcaa cggtaacctt actggtgatg | 420 |
| atactagtaa aattggaggc cttattgggg cccaggtttc cctaggtcat acacttaagt | 480 |
| atgttcaacc tgatttcaaa acaattctcg agagcccaac tgataaaaaa gtaggctgga | 540 |
| aagtgatatt taacaatatg gtgaatcaaa attggggacc atacgatcga gattcttgga | 600 |
| acccggtata tggcaatcaa cttttcatga agactagaaa tggttctatg aaagcagcag | 660 |
| ataacttcct tgatcctaac aaagcaagtt ccctattatc ttcagggttt tcaccagact | 720 |
| tcgctacagt tattactatg gatagaaaag catccaaaca acaaacaaat atagatgtaa | 780 |
| tatacgaacg agttcgtgat gattaccaat tgcattggac ttcaccaaat tggaaaggta | 840 |

TABLE 11-continued

SEQ ID NOs: 9 and 10 - α-hemolysin M113F-RL2
SEQ ID NO: 10 is encoded by residues 39 to 920 of SEQ ID NO: 9
n = a, c, g or t
X at location 5 stands for Leu or Phe
X at location 7 stands for Tyr, Trp, Cys, Ser, Leu or Phe

```
ccaatactaa agataaatgg acagatcgtt cttcagaaag atataaaatc gattgggaaa    900
aagaagaaat gacaaattaa tgtaanttat ttgtacatgt acaaataaat ataatttata    960
actttagccg aagctggatc cggctgctac naanccaa ngnagctgan ttgnctgctg     1020
cccccctgac natactagca naccccttgg gncctaacg ggtctgnggg gtttttgctg    1080
aangngnact tttccgnnan tcnncccggn cccccnggt gaaatccnaa ncccnaacn     1140
gggngntgnta ncaantttan tggnncntna ntttnnaaan cnnntaantt ngnaancccc  1200
nttttncnan ggcnaannnn nanccttna naaaaaance nnngggggggg tttcnntnnn   1260
annnccnttn aangggcccc cnngggggnaa nnntnggggn agatataaaa tcgattggga  1320
aaagaagaa atgacaaatt aa                                             1342

QILIXTXATG TTDIGSNTTV KTGDLVTYDK ENGMHKKVFY SFIDDKNHNK KLLVIRTKGT    60
IAGQYRVYSE EGANKSGLAW PSAFKVQLQL PDNEVAQISD YYPRNSIDTK EYFSTLTYGF   120
NGNLTGDDTS KIGGLIGAQV SLGHTLKYVQ PDFKTILESP TDKKVGWKVI FNNMVNQNWG   180
PYDRDSWNPV YGNQLFMKTR NGSMKAADNF LDPNKASSLL SSGFSPDFAT VITMDRKASK   240
QQTNIDVIYE RVRDDYQLHW TSPNWKGTNT KDKWTDRSSE RYKIDWEKEE MTN          293
```

TABLE 12

SEQ ID NOs: 11 and 12 - α-hemolysin M113N-RL2
SEQ ID NO: 12 is encoded by residues 39 to 920 of SEQ ID NO: 11
n = a, c, g or t
X at location 5 stands for Leu or Phe
X at location 7 stands for Tyr, Trp, Cys, Ser, Leu or Phe

```
gttctgttta actttaagaa gggagatata catatgagca gattctgata ttnacntnng    60
cgaccggtac tacagatatt ggaagcaata ctacagtaaa aacaggtgat ttagtcactt   120
atgataaaga aaatggcatg cacaaaaaag tattttatag ttttatcgat gataaaaatc   180
acaataaaaa actgctagtt attagaacaa aaggtaccat tgctggtcaa tatagagttt   240
atagcgaaga aggtgctaac aaaagtggtt tagcctggcc ttcagccttt aaggtacagt   300
tgcaactacc tgataatgaa gtagctcaaa tatctgatta ctatccgcgg aattcgattg   360
atacaaaaga gtataacagt acgttaacgt acggattcaa cggtaacctt actggtgatg   420
atactagtaa aattggaggc cttattgggg cccaggtttc cctaggtcat acacttaagt   480
atgttcaacc tgatttcaaa acaattctcg agagcccaac tgataaaaaa gtaggctgga   540
aagtgatatt taacaatatg gtgaatcaaa attggggacc atacgatcga gattcttgga   600
acccggtata tggcaatcaa cttttcatga agactagaaa tggttctatg aaagcagcag   660
ataacttcct tgatcctaac aaagcaagtt ccctattatc ttcagggttt tcaccagact   720
tcgctacagt tattactatg gatagaaaag catccaaaca caaacaaat atagatgtaa    780
tatacgaacg agttcgtgat gattaccaat gcattggac ttcaccaaat tggaaaggta    840
ccaatactaa agataaatgg acagatcgtt cttcagaaag atataaaatc gattgggaaa   900
aagaagaaat gacaaattaa tgtaanttat ttgtacatgt acaaataaat ataatttata   960
actttagccg aagctggatc cggctgctac naanccaa ngnagctgan ttgnctgctg    1020
```

TABLE 12-continued

SEQ ID NOs: 11 and 12 - α-hemolysin M113N-RL2
SEQ ID NO: 12 is encoded by residues 39 to 920 of SEQ ID NO: 11
n = a, c, g or t
X at location 5 stands for Leu or Phe
X at location 7 stands for Tyr, Trp, Cys, Ser, Leu or Phe

| | | | | |
|---|---|---|---|---|
| cccccctgac | natactagca | naccccttgg | gncctaacg | ggtctgnggg gttttttgctg | 1080 |
| aangngnact | tttccgnnan | tcnncccggn | ccccccnggt | gaaatccnaa ncccnaacn | 1140 |
| ggngntgnta | ncaantttan | tggnncntna | ntttnnaaan | cnnntaantt ngnaaccccc | 1200 |
| nttttncnan | ggcnaannnn | nanccttna | naaaaaancc | nnnggggggg tttcnntnnn | 1260 |
| annnccnttn | aangggcccc | cnngggnaa | nnntngggn | | 1300 |
| QILIXTXATG | TTDIGSNTTV | KTGDLVTYDK | ENGMHKKVFY | SFIDDKNHNK KLLVIRTKGT | 60 |
| IAGQYRVYSE | EGANKSGLAW | PSAFKVQLQL | PDNEVAQISD | YYPRNSIDTK EYNSTLTYGF | 120 |
| NGNLTGDDTS | KIGGLIGAQV | SLGHTLKYVQ | PDFKTILESP | TDKKVGWKVI FNNMVNQNWG | 180 |
| PYDRDSWNPV | YGNQLFMKTR | NGSMKAADNF | LDPNKASSLL | SSGFSPDFAT VITMDRKASK | 240 |
| QQTNIDVIYE | RVRDDYQLHW | TSPNWKGTNT | KDKWTDRSSE | RYKIDWEKEE MTN | 293 |

TABLE 13

SEQ ID NOs: 13 and 14 - α-hemolysin M113C-D8RL2
SEQ ID NO: 14 is encoded by residues 39 to 944 of SEQ ID NO: 13
n = a, c, g or t
X at location 5 stands for Leu or Phe
X at location 7 stands for Tyr, Trp, Cys, Ser, Leu or Phe

| | | | | |
|---|---|---|---|---|
| gttctgttta | actttaagaa | gggagatata | catatgagca | gattctgata ttnacntnng | 60 |
| cgaccggtac | tacagatatt | ggaagcaata | ctacagtaaa | aacaggtgat ttagtcactt | 120 |
| atgataaaga | aaatggcatg | cacaaaaaag | tattttatag | ttttatcgat gataaaaatc | 180 |
| acaataaaaa | actgctagtt | attagaacaa | aaggtaccat | tgctggtcaa tatagagttt | 240 |
| atagcgaaga | aggtgctaac | aaaagtggtt | tagcctggcc | ttcagccttt aaggtacagt | 300 |
| tgcaactacc | tgataatgaa | gtagctcaaa | tatctgatta | ctatccgcgg aattcgattg | 360 |
| atacaaaaga | gtattgcagt | acgttaacgt | acggattcaa | cggtaacctt actggtgatg | 420 |
| atactagtaa | aattggaggc | cttattgggg | cccaggtttc | cctaggtcat acacttaagt | 480 |
| atgttcaacc | tgatttcaaa | acaattctcg | agagcccaac | tgataaaaaa gtaggctgga | 540 |
| aagtgatatt | taacaatatg | gtgaatcaaa | attgggacc | atacgatcga gattcttgga | 600 |
| acccggtata | tggcaatcaa | cttttcatga | agactagaaa | tggttctatg aaagcagcag | 660 |
| ataacttcct | tgatcctaac | aaagcaagtt | ccctattatc | ttcagggttt tcaccagact | 720 |
| tcgctacagt | tattactatg | gatagaaaag | catccaaaca | acaaacaaat atagatgtaa | 780 |
| tatacgaacg | agttcgtgat | gattaccaat | tgcattggac | ttcaccaaat tggaaaggta | 840 |
| ccaatactaa | agataaatgg | acagatcgtt | cttcagaaag | atataaaatc gattgggaaa | 900 |
| aagaagaaat | gacaaatgat | gacgatgatg | acgacgatga | ttaatgtaan ttatttgtac | 960 |
| atgtacaaat | aaatataatt | tataacttta | gccgaagctg | gatccggctg ctacnaancc | 1020 |
| cnaangnagc | tganttgnct | gctgcccccc | tgacnatact | agcanacccc ttgggnccct | 1080 |
| aacgggtctg | ngggttttt | gctgaangng | nactttccg | nnantcnncc cggncccccc | 1140 |
| nggtgaaatc | cnaaccccn | aacnggngnt | gntancaant | ttantggnnc ntnantttnn | 1200 |
| aaancnnnta | anttngnaan | ccccnttttn | cnanggcnaa | nnnnnancct ttanaaaaaa | 1260 |
| anccnnnggg | ggggtttcnn | tnnn | | | 1284 |

TABLE 13-continued

SEQ ID NOs: 13 and 14 - α-hemolysin M113C-D8RL2
SEQ ID NO: 14 is encoded by residues 39 to 944 of SEQ ID NO: 13
n = a, c, g or t
X at location 5 stands for Leu or Phe
X at location 7 stands for Tyr, Trp, Cys, Ser, Leu or Phe

```
QILIXTXATG TTDIGSNTTV KTGDLVTYDK ENGMHKKVFY SFIDDKNHNK KLLVIRTKGT      60

IAGQYRVYSE EGANKSGLAW PSAFKVQLQL PDNEVAQISD YYPRNSIDTK EYCSTLTYGF     120

NGNLTGDDTS KIGGLIGAQV SLGHTLKYVQ PDFKTILESP TDKKVGWKVI FNNMVNQNWG     180

PYDRDSWNPV YGNQLFMKTR NGSMKAADNF LDPNKASSLL SSGFSPDFAT VITMDRKASK     240

QQTNIDVIYE RVRDDYQLHW TSPNWKGTNT KDKWTDRSSE RYKIDWEKEE MTNDDDDDDD     300

D                                                                    301
```

TABLE 14

SEQ ID NOs: 15 and 16 - α-hemolysin T117C-D8RL3
SEQ ID NO: 16 is encoded by residues 13 to 918 of SEQ ID NO: 15

```
gatatacata tggcagattc tgatattaat attaaaaccg gtactacaga tattggaagc      60
aatactacag taaaaacagg tgatttagtc acttatgata agaaaatgg catgcacaaa     120 aaagtatttt atagttttat cgatgataaa aatcacaata aaaaactgct agttattaga    180
acaaaaggta ccattgctgg tcaatataga gtttatagcg aagaaggtgc taacaaaagt    240
ggtttagcct ggccttcagc ctttaaggta cagttgcaac tacctgataa tgaagtagct    300
caaatatctg attactatcc gcggaattcg attgatacaa aagagtatat gagtacgtta    360
tgctacggat tcaacggtaa tgttactggt gatgatacag gaaaaattgg aggccttatt    420
ggtgcaaatg tttcgattgg tcatacactt aagtatgttc aacctgattt caaaacaatt    480
ctcgagagcc caactgataa aaagtaggc tggaaagtga tatttaacaa tatggtgaat    540
caaaattggg gaccatacga tcgagattct tggaacccgg tatatggcaa tcaacttttc    600
atgaaaacta gaaatggttc tatgaaagca gcagataact tccttgatcc taacaaagca    660
agttctctat tatcttcagg gttttcacca gacttcgcta cagttattac tatggataga    720
aaagcatcca acaacaaac aaatatagat gtaatatacg aacgagttcg tgatgattac    780
caattgcatt ggacttcaac aaattggaaa ggtaccaata ctaaagataa atggacagat    840
cgttcttcag aaagatataa aatcgattgg gaaaaagaag aaatgacaaa tgatgacgat    900
gatgacgacg atgattgata agcttggatc cggctgc                             937

ADSDINIKTG TTDIGSNTTV KTGDLVTYDK ENGMHKKVFY SFIDDKNHNK KLLVIRTKGT      60

IAGQYRVYSE EGANKSGLAW PSAFKVQLQL PDNEVAQISD YYPRNSIDTK EYMSTLCYGF     120

NGNVTGDDTG KIGGLIGANV SIGHTLKYVQ PDFKTILESP TDKKVGWKVI FNNMVNQNWG     180

PYDRDSWNPV YGNQLFMKTR NGSMKAADNF LDPNKASSLL SSGFSPDFAT VITMDRKASK     240

QQTNIDVIYE RVRDDYQLHW TSTNWKGTNT KDKWTDRSSE RYKIDWEKEE MTNDDDDDDD     300

D                                                                    301
```

TABLE 15

| SEQ ID NO: 17 - lambda exonuclease | |
|---|---|
| SHMTPDIILQ RTGIDVRAVE QGDDAWHKLR LGVITASEVH NVIAKPRSGK KWPDMKMSYF | 60 |
| HTLLAEVCTG VAPEVNAKAL AWGKQYENDA RTLFEFTSGV NVTESPIIYR DESMRTACSP | 120 |
| DGLCSDGNGL ELKCPFTSRD FMKFRLGGFE AIKSAYMAQV QYSMWVTRKN AWYFANYDPR | 180 |
| MKREGLHYVV IERDEKYMAS FDEIVPEFIE KMDEALAEIG FVFGEQWR | 228 |

TABLE 16

| SEQ ID NO: 18 - α-hemolysin-D8RL3 | |
|---|---|
| gcagattctg atattaatat taaaaccggt actacagata ttggaagcaa tactacagta | 60 |
| aaaacaggtg atttagtcac ttatgataaa gaaaatggca tgcacaaaaa agtattttat | 120 |
| agttttatcg atgataaaaa tcacaataaa aaactgctag ttattagaac aaaaggtacc | 180 |
| attgctggtc aatatagagt ttatagcgaa gaaggtgcta acaaaagtgg tttagcctgg | 240 |
| ccttcagcct ttaaggtaca gttgcaacta cctgataatg aagtagctca aatatctgat | 300 |
| tactatccgc ggaattcgat tgatacaaaa gagtatatga gtacgttaac gtacggattc | 360 |
| aacggtaatg ttactggtga tgatacagga aaaattggag gccttattgg tgcaaatgtt | 420 |
| tcgattggtc atacacttaa gtatgttcaa cctgatttca aaacaattct cgagagccca | 480 |
| actgataaaa aagtaggctg gaaagtgata tttaacaata tggtgaatca aaattgggga | 540 |
| ccatacgatc gagattcttg gaacccggta tatggcaatc aacttttcat gaaaactaga | 600 |
| aatggttcta tgaaagcagc agataacttc cttgatccta acaaagcaag ttctctatta | 660 |
| tcttcagggt tttcaccaga cttcgctaca gttattacta tggatagaaa agcatccaaa | 720 |
| caacaaacaa atatagatgt aatatacgaa cgagttcgtg atgattacca attgcattgg | 780 |
| acttcaacaa attggaaagg taccaatact aaagataaat ggacagatcg ttcttcagaa | 840 |
| agatataaaa tcgattggga aaaagaagaa atgacaaatg atgacgatga tgacgacgat | 900 |
| gattgataag cttggatccg gctgc | 925 |

The invention claimed is:

1. A plurality of transmembrane protein pores, each covalently attached to a cyclodextrin molecular adaptor that facilitates an interaction between the pore and a nucleic acid analyte, wherein:
   (i) the pores are variants of α-hemolysin in which one or more of the subunits has at least 50% homology to SEQ ID NO: 2 based on amino acid identity over the entire sequence and which retain pore activity;
   (ii) the adaptors in the plurality of pores are collectively orientated so that either (a) the primary hydroxyls or amino groups of the adaptors face the trans entrance of the pore or (b) the secondary hydroxyls or amino groups of the adaptors face the trans end of the pores;
   (iii) the pores are modified at position 113 in one or more subunits to facilitate the orientation of the adaptors, and
   (iv) the pores are modified at position 113 or 117 in one or more subunits to facilitate the covalent attachment of the adaptors.

2. A method of producing a plurality of transmembrane protein pores according to claim 1, comprising:
   (a) providing a plurality of transmembrane protein pores which are variants of α-hemolysin in which one or more of the subunits has at least 50% homology to SEQ ID NO: 2 based on amino acid identity over the entire sequence, which retain pore activity, which are modified at position 113 or 117 in one or more of the subunits to facilitate the covalent attachment of cyclodextrin molecular adaptors, wherein the adaptors facilitate an interaction between the pores and a nucleic acid analyte, and which are modified at position 113 in one or more of the subunits to facilitate the orientation of the adaptors;
   (b) covalently attaching the adaptor to each of the pores; and
   (c) determining whether or not the adaptors in the plurality of pores are collectively orientated so that either the primary hydroxyls or amino groups of the adaptors face the trans entrance of the pores, or the secondary hydroxyls or amino groups of the adaptors face the trans end of the pores.

3. A method of determining presence or absence of an analyte, comprising:
   (a) contacting the analyte with a plurality of transmembrane protein pores according to claim 1 so that the analyte interacts with the pores; and
   (b) measuring the current passing through the pores during the interaction and thereby determining the presence or absence of the analyte.

4. A method of identifying an individual nucleotide, comprising:
   (a) contacting the nucleotide with a plurality of transmembrane protein pores according to claim 1 so that the nucleotide interacts with the pores; and
   (b) measuring the current passing through the pores during the interaction and thereby determining the identity of the nucleotide.

5. A method of sequencing a target nucleic acid sequence, comprising:
   (a) digesting an individual nucleotide from one end of the target sequence using a processive exonuclease;
   (b) contacting the nucleotide with a plurality of transmembrane protein pores according to claim 1 so that the nucleotide interacts with the adaptor;
   (c) measuring the current passing through the pores during the interaction and thereby determining the identity of the nucleotide; and
   (d) repeating steps (a) to (c) at the same end of the nucleic acid sequence and thereby determining the sequence of the nucleic acid.

6. A kit for sequencing a nucleic acid, comprising a plurality of transmembrane protein pores according to claim 1 and a processive exonuclease.

7. A plurality of transmembrane protein pores according to claim 1, wherein the cyclodextrin is heptakis-6-amino-β-cyclodextrin (am7-β-CD) or 6-monodeoxy-6-monoamino-β-cyclodextrin (am1β-CD).

8. A plurality of transmembrane protein pores according to claim 1, wherein the pores are modified at position 113 in six subunits to facilitate the orientation of the adaptors.

* * * * *

SEQUENCE LISTING

<160> NUMBER OF SEQ ID NOS: 18

<210> SEQ ID NO 1
<211> LENGTH: 882
<212> TYPE: DNA
<213> ORGANISM: Staphylococcus aureus
<220> FEATURE:
<221> NAME/KEY: CDS
<222> LOCATION: (1)..(879)

<400> SEQUENCE: 1

```
gca gat tct gat att aat att aaa acc ggt act aca gat att gga agc      48
Ala Asp Ser Asp Ile Asn Ile Lys Thr Gly Thr Thr Asp Ile Gly Ser
1               5                   10                  15 aat act aca gta aaa aca ggt gat tta gtc act tat gat aaa gaa aat      96
Asn Thr Thr Val Lys Thr Gly Asp Leu Val Thr Tyr Asp Lys Glu Asn
            20                  25                  30 ggc atg cac aaa aaa gta ttt tat agt ttt atc gat gat aaa aat cac     144
```

```
                                                        -continued

Gly Met His Lys Lys Val Phe Tyr Ser Phe Ile Asp Lys Asn His
         35                  40                  45 aat aaa aaa ctg cta gtt att aga acg aaa ggt acc att gct ggt caa      192
Asn Lys Lys Leu Leu Val Ile Arg Thr Lys Gly Thr Ile Ala Gly Gln
     50                  55                  60 tat aga gtt tat agc gaa gaa ggt gct aac aaa agt ggt tta gcc tgg      240
Tyr Arg Val Tyr Ser Glu Glu Gly Ala Asn Lys Ser Gly Leu Ala Trp
 65                  70                  75                  80 cct tca gcc ttt aag gta cag ttg caa cta cct gat aat gaa gta gct      288
Pro Ser Ala Phe Lys Val Gln Leu Gln Leu Pro Asp Asn Glu Val Ala
                 85                  90                  95 caa ata tct gat tac tat cca aga aat tcg att gat aca aaa gag tat      336
Gln Ile Ser Asp Tyr Tyr Pro Arg Asn Ser Ile Asp Thr Lys Glu Tyr
             100                 105                 110 atg agt act tta act tat gga ttc aac ggt aat gtt act ggt gat gat      384
Met Ser Thr Leu Thr Tyr Gly Phe Asn Gly Asn Val Thr Gly Asp Asp
         115                 120                 125 aca gga aaa att ggc ggc ctt att ggt gca aat gtt tcg att ggt cat      432
Thr Gly Lys Ile Gly Gly Leu Ile Gly Ala Asn Val Ser Ile Gly His
    130                 135                 140 aca ctg aaa tat gtt caa cct gat ttc aaa aca att tta gag agc cca      480
Thr Leu Lys Tyr Val Gln Pro Asp Phe Lys Thr Ile Leu Glu Ser Pro
145                 150                 155                 160 act gat aaa aaa gta ggc tgg aaa gtg ata ttt aac aat atg gtg aat      528
Thr Asp Lys Lys Val Gly Trp Lys Val Ile Phe Asn Asn Met Val Asn
                165                 170                 175 caa aat tgg gga cca tat gat aga gat tct tgg aac ccg gta tat ggc      576
Gln Asn Trp Gly Pro Tyr Asp Arg Asp Ser Trp Asn Pro Val Tyr Gly
            180                 185                 190 aat caa ctt ttc atg aaa act aga aat ggt tct atg aaa gca gca gat      624
Asn Gln Leu Phe Met Lys Thr Arg Asn Gly Ser Met Lys Ala Ala Asp
        195                 200                 205 aac ttc ctt gat cct aac aaa gca agt tct cta tta tct tca ggg ttt      672
Asn Phe Leu Asp Pro Asn Lys Ala Ser Ser Leu Leu Ser Ser Gly Phe
    210                 215                 220 tca cca gac ttc gct aca gtt att act atg gat aga aaa gca tcc aaa      720
Ser Pro Asp Phe Ala Thr Val Ile Thr Met Asp Arg Lys Ala Ser Lys
225                 230                 235                 240 caa caa aca aat ata gat gta ata tac gaa cga gtt cgt gat gat tac      768
Gln Gln Thr Asn Ile Asp Val Ile Tyr Glu Arg Val Arg Asp Asp Tyr
                245                 250                 255 caa ttg cat tgg act tca aca aat tgg aaa ggt acc aat act aaa gat      816
Gln Leu His Trp Thr Ser Thr Asn Trp Lys Gly Thr Asn Thr Lys Asp
            260                 265                 270 aaa tgg aca gat cgt tct tca gaa aga tat aaa atc gat tgg gaa aaa      864
Lys Trp Thr Asp Arg Ser Ser Glu Arg Tyr Lys Ile Asp Trp Glu Lys
        275                 280                 285 gaa gaa atg aca aat taa                                              882
Glu Glu Met Thr Asn
    290

<210> SEQ ID NO 2
<211> LENGTH: 293
<212> TYPE: PRT
<213> ORGANISM: Staphylococcus aureus

<400> SEQUENCE: 2

Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
```

-continued

```
                20                  25                  30
Gly Met His Lys Lys Val Phe Tyr Ser Phe Ile Asp Asp Lys Asn His
                35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
                100                 105                 110

Met Ser Thr Leu Thr Tyr Gly Phe Asn Gly Asn Val Thr Gly Asp Asp
                115                 120                 125

Thr Gly Lys Ile Gly Gly Leu Ile Gly Ala Asn Val Ser Ile Gly His
                130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
                195                 200                 205

Asn Phe Leu Asp Pro Asn Lys Ala Ser Ser Leu Leu Ser Ser Gly Phe
                210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
                260                 265                 270

Lys Trp Thr Asp Arg Ser Ser Glu Arg Tyr Lys Ile Asp Trp Glu Lys
    275                 280                 285

Glu Glu Met Thr Asn
        290

<210> SEQ ID NO 3
<211> LENGTH: 1300
<212> TYPE: DNA
<213> ORGANISM: Artificial sequence
<220> FEATURE:
<223> OTHER INFORMATION: M113H-RL2 alpha hemolysin mutant
<220> FEATURE:
<221> NAME/KEY: CDS
<222> LOCATION: (39)..(920)
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
```

```
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1067)..(1067)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1097)..(1098)
<223> OTHER INFORMATION: n is a, c, g, or t
<220> FEATURE:
<221> NAME/KEY: misc_feature
<222> LOCATION: (1100)..(1100)
<223> OTHER INFORMATION: n is a, c, g, or t
<220> FEATURE:
<221> NAME/KEY: misc_feature
<222> LOCATION: (1103)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
```

```
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1175)..(1176)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1182)..(1184)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1196)..(1196)
<223> OTHER INFORMATION: n is a, c, g, or t
```

-continued

```
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1210)..(1210)
<223> OTHER INFORMATION: n is a, c, g, or t
<220> FEATURE:
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1217)..(1221)
<223> OTHER INFORMATION: n is a, c, g, or t
<220> FEATURE:
<221> NAME/KEY: misc_feature
<222> LOCATION: (1223)..(1223)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1241)..(1243)
<223> OTHER INFORMATION: n is a, c, g, or t
<220> FEATURE:
<221> NAME/KEY: misc_feature
<222> LOCATION: (1255)..(1256)
<223> OTHER INFORMATION: n is a, c, g, or t
<220> FEATURE:
<221> NAME/KEY: misc_feature
<222> LOCATION: (1258)..(1260)
<223> OTHER INFORMATION: n is a, c, g, or t
<220> FEATURE:
<221> NAME/KEY: misc_feature
<222> LOCATION: (1262)..(1264)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
<222> LOCATION: (1270)..(1270)
<223> OTHER INFORMATION: n is a, c, g, or t
<220> FEATURE:
<221> NAME/KEY: misc_feature
<222> LOCATION: (1273)..(1273)
<223> OTHER INFORMATION: n is a, c, g, or t
<220> FEATURE:
<221> NAME/KEY: misc_feature
<222> LOCATION: (1282)..(1283)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1291)..(1293)
```

```
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t

<400> SEQUENCE: 3
gttctgttta actttaagaa gggagatata catatgag cag att ctg ata ttn acn        56
                                          Gln Ile Leu Ile Xaa Thr
                                            1               5 tnn gcg acc ggt act aca gat att gga agc aat act aca gta aaa aca        104
Xaa Ala Thr Gly Thr Thr Asp Ile Gly Ser Asn Thr Thr Val Lys Thr
         10                  15                  20 ggt gat tta gtc act tat gat aaa gaa aat ggc atg cac aaa aaa gta        152
Gly Asp Leu Val Thr Tyr Asp Lys Glu Asn Gly Met His Lys Lys Val
 25                  30                  35 ttt tat agt ttt atc gat gat aaa aat cac aat aaa aaa ctg cta gtt        200
Phe Tyr Ser Phe Ile Asp Asp Lys Asn His Asn Lys Lys Leu Leu Val
 40                  45                  50 att aga aca aaa ggt acc att gct ggt caa tat aga gtt tat agc gaa        248
Ile Arg Thr Lys Gly Thr Ile Ala Gly Gln Tyr Arg Val Tyr Ser Glu
 55                  60                  65                  70 gaa ggt gct aac aaa agt ggt tta gcc tgg cct tca gcc ttt aag gta        296
Glu Gly Ala Asn Lys Ser Gly Leu Ala Trp Pro Ser Ala Phe Lys Val
                 75                  80                  85 cag ttg caa cta cct gat aat gaa gta gct caa ata tct gat tac tat        344
Gln Leu Gln Leu Pro Asp Asn Glu Val Ala Gln Ile Ser Asp Tyr Tyr
             90                  95                 100 ccg cgg aat tcg att gat aca aaa gag tat cac agt acg tta acg tac        392
Pro Arg Asn Ser Ile Asp Thr Lys Glu Tyr His Ser Thr Leu Thr Tyr
         105                 110                 115 gga ttc aac ggt aac ctt act ggt gat gat act agt aaa att gga ggc        440
Gly Phe Asn Gly Asn Leu Thr Gly Asp Asp Thr Ser Lys Ile Gly Gly
     120                 125                 130 ctt att ggg gcc cag gtt tcc cta ggt cat aca ctt aag tat gtt caa        488
Leu Ile Gly Ala Gln Val Ser Leu Gly His Thr Leu Lys Tyr Val Gln
135                 140                 145                 150 cct gat ttc aaa aca att ctc gag agc cca act gat aaa aaa gta ggc        536
Pro Asp Phe Lys Thr Ile Leu Glu Ser Pro Thr Asp Lys Lys Val Gly
                155                 160                 165 tgg aaa gtg ata ttt aac aat atg gtg aat caa aat tgg gga cca tac        584
Trp Lys Val Ile Phe Asn Asn Met Val Asn Gln Asn Trp Gly Pro Tyr
            170                 175                 180 gat cga gat tct tgg aac ccg gta tat ggc aat caa ctt ttc atg aag        632
Asp Arg Asp Ser Trp Asn Pro Val Tyr Gly Asn Gln Leu Phe Met Lys
        185                 190                 195 act aga aat ggt tct atg aaa gca gca gat aac ttc ctt gat cct aac        680
Thr Arg Asn Gly Ser Met Lys Ala Ala Asp Asn Phe Leu Asp Pro Asn
    200                 205                 210 aaa gca agt tcc cta tta tct tca ggg ttt tca cca gac ttc gct aca        728
Lys Ala Ser Ser Leu Leu Ser Ser Gly Phe Ser Pro Asp Phe Ala Thr
215                 220                 225                 230 gtt att act atg gat aga aaa gca tcc aaa caa caa aca aat ata gat        776
Val Ile Thr Met Asp Arg Lys Ala Ser Lys Gln Gln Thr Asn Ile Asp
                235                 240                 245 gta ata tac gaa cga gtt cgt gat gat tac caa ttg cat tgg act tca        824
Val Ile Tyr Glu Arg Val Arg Asp Asp Tyr Gln Leu His Trp Thr Ser
            250                 255                 260
```

```
cca aat tgg aaa ggt acc aat act aaa gat aaa tgg aca gat cgt tct      872
Pro Asn Trp Lys Gly Thr Asn Thr Lys Asp Lys Trp Thr Asp Arg Ser
        265                 270                 275 tca gaa aga tat aaa atc gat tgg gaa aaa gaa gaa atg aca aat taa      920
Ser Glu Arg Tyr Lys Ile Asp Trp Glu Lys Glu Glu Met Thr Asn
    280                 285                 290 tgtaanttat ttgtacatgt acaaataaat ataatttata actttagccg aagctggatc   980
cggctgctac naanccccnaa ngnagctgan ttgnctgctg cccccctgac natactagca  1040
naccccttgg gnccctaacg ggtctgnggg gttttttgctg aangngnact tttccgnnan  1100 tcnnccccggn ccccccngt gaaatccnaa nccccnaacn ggngntgnta ncaantttan   1160
tggnncntna ntttnnaaan cnnntaantt ngnaacccc ntttttcnan ggcnaannnn    1220 nanccttna naaaaaance nnngggggg tttcnntnnn annncentin aanggcccc      1280 cnngggnaa nnntngggn                                                 1300

<210> SEQ ID NO 4
<211> LENGTH: 293
<212> TYPE: PRT
<213> ORGANISM: Artificial sequence
<220> FEATURE:
<221> NAME/KEY: misc_feature
<222> LOCATION: (5)..(5)
<223> OTHER INFORMATION: The 'Xaa' at location 5 stands for Leu, or Phe.
<220> FEATURE:
<221> NAME/KEY: misc_feature
<222> LOCATION: (7)..(7)
<223> OTHER INFORMATION: The 'Xaa' at location 7 stands for Tyr, Trp,
      Cys, Ser, Leu, or Phe.
<220> FEATURE:
<223> OTHER INFORMATION: Synthetic Construct

<400> SEQUENCE: 4

Gln Ile Leu Ile Xaa Thr Xaa Ala Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

His Ser Thr Leu Thr Tyr Gly Phe Asn Gly Asn Leu Thr Gly Asp Asp
        115                 120                 125

Thr Ser Lys Ile Gly Gly Leu Ile Gly Ala Gln Val Ser Leu Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
```

```
                    195                 200                 205
Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Pro Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

<210> SEQ ID NO 5
<211> LENGTH: 1300
<212> TYPE: DNA
<213> ORGANISM: Artificial sequence
<220> FEATURE:
<223> OTHER INFORMATION: M113K-RL2 alpha hemolysin mutant
<220> FEATURE:
<221> NAME/KEY: CDS
<222> LOCATION: (39)..(920)
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
```

```
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1067)..(1067)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1097)..(1098)
<223> OTHER INFORMATION: n is a, c, g, or t
<220> FEATURE:
<221> NAME/KEY: misc_feature
<222> LOCATION: (1100)..(1100)
<223> OTHER INFORMATION: n is a, c, g, or t
<220> FEATURE:
<221> NAME/KEY: misc_feature
<222> LOCATION: (1103)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
```

-continued

```
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1175)..(1176)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1182)..(1184)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1196)..(1196)
<223> OTHER INFORMATION: n is a, c, g, or t
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1210)..(1210)
<223> OTHER INFORMATION: n is a, c, g, or t
<220> FEATURE:
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1217)..(1221)
<223> OTHER INFORMATION: n is a, c, g, or t
<220> FEATURE:
<221> NAME/KEY: misc_feature
<222> LOCATION: (1223)..(1223)
<223> OTHER INFORMATION: n is a, c, g, or t
<220> FEATURE:
<221> NAME/KEY: misc_feature
<222> LOCATION: (1229)..(1229)
```

<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1241)..(1243)
<223> OTHER INFORMATION: n is a, c, g, or t
<220> FEATURE:
<221> NAME/KEY: misc_feature
<222> LOCATION: (1255)..(1256)
<223> OTHER INFORMATION: n is a, c, g, or t
<220> FEATURE:
<221> NAME/KEY: misc_feature
<222> LOCATION: (1258)..(1260)
<223> OTHER INFORMATION: n is a, c, g, or t
<220> FEATURE:
<221> NAME/KEY: misc_feature
<222> LOCATION: (1262)..(1264)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
<222> LOCATION: (1270)..(1270)
<223> OTHER INFORMATION: n is a, c, g, or t
<220> FEATURE:
<221> NAME/KEY: misc_feature
<222> LOCATION: (1273)..(1273)
<223> OTHER INFORMATION: n is a, c, g, or t
<220> FEATURE:
<221> NAME/KEY: misc_feature
<222> LOCATION: (1282)..(1283)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1291)..(1293)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t

<400> SEQUENCE: 5

```
gttctgttta actttaagaa gggagatata catatgag cag att ctg ata ttn acn        56
                                         Gln Ile Leu Ile Xaa Thr
                                          1               5 tnn gcg acc ggt act aca gat att gga agc aat act aca gta aaa aca        104
Xaa Ala Thr Gly Thr Thr Asp Ile Gly Ser Asn Thr Thr Val Lys Thr
         10                  15                  20 ggt gat tta gtc act tat gat aaa gaa aat ggc atg cac aaa aaa gta        152
Gly Asp Leu Val Thr Tyr Asp Lys Glu Asn Gly Met His Lys Lys Val
 25                  30                  35 ttt tat agt ttt atc gat gat aaa aat cac aat aaa aaa ctg cta gtt        200
Phe Tyr Ser Phe Ile Asp Asp Lys Asn His Asn Lys Lys Leu Leu Val
         40                  45                  50 att aga aca aaa ggt acc att gct ggt caa tat aga gtt tat agc gaa        248
Ile Arg Thr Lys Gly Thr Ile Ala Gly Gln Tyr Arg Val Tyr Ser Glu
 55                  60                  65                  70
```

```
gaa ggt gct aac aaa agt ggt tta gcc tgg cct tca gcc ttt aag gta    296
Glu Gly Ala Asn Lys Ser Gly Leu Ala Trp Pro Ser Ala Phe Lys Val
             75                  80                  85 cag ttg caa cta cct gat aat gaa gta gct caa ata tct gat tac tat    344
Gln Leu Gln Leu Pro Asp Asn Glu Val Ala Gln Ile Ser Asp Tyr Tyr
         90                  95                 100 ccg cgg aat tcg att gat aca aaa gag tat aaa agt acg tta acg tac    392
Pro Arg Asn Ser Ile Asp Thr Lys Glu Tyr Lys Ser Thr Leu Thr Tyr
     105                 110                 115 gga ttc aac ggt aac ctt act ggt gat gat act agt aaa att gga ggc    440
Gly Phe Asn Gly Asn Leu Thr Gly Asp Asp Thr Ser Lys Ile Gly Gly
 120                 125                 130 ctt att ggg gcc cag gtt tcc cta ggt cat aca ctt aag tat gtt caa    488
Leu Ile Gly Ala Gln Val Ser Leu Gly His Thr Leu Lys Tyr Val Gln
135                 140                 145                 150 cct gat ttc aaa aca att ctc gag agc cca act gat aaa aaa gta ggc    536
Pro Asp Phe Lys Thr Ile Leu Glu Ser Pro Thr Asp Lys Lys Val Gly
             155                 160                 165 tgg aaa gtg ata ttt aac aat atg gtg aat caa aat tgg gga cca tac    584
Trp Lys Val Ile Phe Asn Asn Met Val Asn Gln Asn Trp Gly Pro Tyr
         170                 175                 180 gat cga gat tct tgg aac ccg gta tat ggc aat caa ctt ttc atg aag    632
Asp Arg Asp Ser Trp Asn Pro Val Tyr Gly Asn Gln Leu Phe Met Lys
     185                 190                 195 act aga aat ggt tct atg aaa gca gca gat aac ttc ctt gat cct aac    680
Thr Arg Asn Gly Ser Met Lys Ala Ala Asp Asn Phe Leu Asp Pro Asn
 200                 205                 210 aaa gca agt tcc cta tta tct tca ggg ttt tca cca gac ttc gct aca    728
Lys Ala Ser Ser Leu Leu Ser Ser Gly Phe Ser Pro Asp Phe Ala Thr
215                 220                 225                 230 gtt att act atg gat aga aaa gca tcc aaa caa caa aca aat ata gat    776
Val Ile Thr Met Asp Arg Lys Ala Ser Lys Gln Gln Thr Asn Ile Asp
             235                 240                 245 gta ata tac gaa cga gtt cgt gat gat tac caa ttg cat tgg act tca    824
Val Ile Tyr Glu Arg Val Arg Asp Asp Tyr Gln Leu His Trp Thr Ser
         250                 255                 260 cca aat tgg aaa ggt acc aat act aaa gat aaa tgg aca gat cgt tct    872
Pro Asn Trp Lys Gly Thr Asn Thr Lys Asp Lys Trp Thr Asp Arg Ser
     265                 270                 275 tca gaa aga tat aaa atc gat tgg gaa aaa gaa gaa atg aca aat taa    920
Ser Glu Arg Tyr Lys Ile Asp Trp Glu Lys Glu Glu Met Thr Asn
 280                 285                 290 tgtaanttat ttgtacatgt acaaataaat ataatttata actttagccg aagctggatc    980
cggctgctac naancccnaa ngnagctgan ttgnctgctg cccccctgac natactagca   1040
naccccttgg gnccctaacg ggtctgnggg gtttttgctg aangngnact tttccgnnan   1100 tcnnccggn cccccnggt gaaatccnaa ncccnaacn ggngntgnta ncaantttan     1160
tggnncntna ntttnnaaan cnnntaantt ngnaancccc nttttncnan ggcnaannnn   1220 nanccttna naaaaaancc nnnggggggg tttcnntnnn annnccnttn aangggcccc   1280
cnnggggnaa nnntnggggn                                              1300

<210> SEQ ID NO 6
<211> LENGTH: 293
<212> TYPE: PRT
<213> ORGANISM: Artificial sequence
<220> FEATURE:
<221> NAME/KEY: misc_feature
<222> LOCATION: (5)..(5)
```

```
<223> OTHER INFORMATION: The 'Xaa' at location 5 stands for Leu, or Phe.
<220> FEATURE:
<221> NAME/KEY: misc_feature
<222> LOCATION: (7)..(7)
<223> OTHER INFORMATION: The 'Xaa' at location 7 stands for Tyr, Trp,
      Cys, Ser, Leu, or Phe.
<220> FEATURE:
<223> OTHER INFORMATION: Synthetic Construct

<400> SEQUENCE: 6
```

Gln Ile Leu Ile Xaa Thr Xaa Ala Thr Gly Thr Thr Asp Ile Gly Ser
1               5               10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Lys Ser Thr Leu Thr Tyr Gly Phe Asn Gly Asn Leu Thr Gly Asp Asp
        115                 120                 125

Thr Ser Lys Ile Gly Gly Leu Ile Gly Ala Gln Val Ser Leu Gly His
130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Pro Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
        290

```
<210> SEQ ID NO 7
<211> LENGTH: 1300
<212> TYPE: DNA
<213> ORGANISM: Artificial sequence
<220> FEATURE:
<223> OTHER INFORMATION: M113R-RL2 alpha hemolysin mutant
<220> FEATURE:
<221> NAME/KEY: CDS
<222> LOCATION: (39)..(920)
<220> FEATURE:
```

```
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1067)..(1067)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1097)..(1098)
<223> OTHER INFORMATION: n is a, c, g, or t
<220> FEATURE:
<221> NAME/KEY: misc_feature
<222> LOCATION: (1100)..(1100)
<223> OTHER INFORMATION: n is a, c, g, or t
```

-continued

```
<220> FEATURE:
<221> NAME/KEY: misc_feature
<222> LOCATION: (1103)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1175)..(1176)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1182)..(1184)
```

-continued

```
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1196)..(1196)
<223> OTHER INFORMATION: n is a, c, g, or t
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1210)..(1210)
<223> OTHER INFORMATION: n is a, c, g, or t
<220> FEATURE:
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1217)..(1221)
<223> OTHER INFORMATION: n is a, c, g, or t
<220> FEATURE:
<221> NAME/KEY: misc_feature
<222> LOCATION: (1223)..(1223)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1241)..(1243)
<223> OTHER INFORMATION: n is a, c, g, or t
<220> FEATURE:
<221> NAME/KEY: misc_feature
<222> LOCATION: (1255)..(1256)
<223> OTHER INFORMATION: n is a, c, g, or t
<220> FEATURE:
<221> NAME/KEY: misc_feature
<222> LOCATION: (1258)..(1260)
<223> OTHER INFORMATION: n is a, c, g, or t
<220> FEATURE:
<221> NAME/KEY: misc_feature
<222> LOCATION: (1262)..(1264)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
```

<222> LOCATION: (1270)..(1270)
<223> OTHER INFORMATION: n is a, c, g, or t
<220> FEATURE:
<221> NAME/KEY: misc_feature
<222> LOCATION: (1273)..(1273)
<223> OTHER INFORMATION: n is a, c, g, or t
<220> FEATURE:
<221> NAME/KEY: misc_feature
<222> LOCATION: (1282)..(1283)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1291)..(1293)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t

<400> SEQUENCE: 7

```
gttctgttta actttaagaa gggagatata catatgag cag att ctg ata ttn acn      56
                                         Gln Ile Leu Ile Xaa Thr
                                           1               5 tnn gcg acc ggt act aca gat att gga agc aat act aca gta aaa aca       104
Xaa Ala Thr Gly Thr Thr Asp Ile Gly Ser Asn Thr Thr Val Lys Thr
         10                  15                  20 ggt gat tta gtc act tat gat aaa gaa aat ggc atg cac aaa aaa gta       152
Gly Asp Leu Val Thr Tyr Asp Lys Glu Asn Gly Met His Lys Lys Val
 25                  30                  35 ttt tat agt ttt atc gat gat aaa aat cac aat aaa aaa ctg cta gtt       200
Phe Tyr Ser Phe Ile Asp Asp Lys Asn His Asn Lys Lys Leu Leu Val
         40                  45                  50 att aga aca aaa ggt acc att gct ggt caa tat aga gtt tat agc gaa       248
Ile Arg Thr Lys Gly Thr Ile Ala Gly Gln Tyr Arg Val Tyr Ser Glu
 55                  60                  65                  70 gaa ggt gct aac aaa agt ggt tta gcc tgg cct tca gcc ttt aag gta       296
Glu Gly Ala Asn Lys Ser Gly Leu Ala Trp Pro Ser Ala Phe Lys Val
                 75                  80                  85 cag ttg caa cta cct gat aat gaa gta gct caa ata tct gat tac tat       344
Gln Leu Gln Leu Pro Asp Asn Glu Val Ala Gln Ile Ser Asp Tyr Tyr
             90                  95                 100 ccg cgg aat tcg att gat aca aaa gag tat aga agt acg tta acg tac       392
Pro Arg Asn Ser Ile Asp Thr Lys Glu Tyr Arg Ser Thr Leu Thr Tyr
        105                 110                 115 gga ttc aac ggt aac ctt act ggt gat gat act agt aaa att gga ggc       440
Gly Phe Asn Gly Asn Leu Thr Gly Asp Asp Thr Ser Lys Ile Gly Gly
    120                 125                 130 ctt att ggg gcc cag gtt tcc cta ggt cat aca ctt aag tat gtt caa       488
Leu Ile Gly Ala Gln Val Ser Leu Gly His Thr Leu Lys Tyr Val Gln
135                 140                 145                 150 cct gat ttc aaa aca att ctc gag agc cca act gat aaa aaa gta ggc       536
Pro Asp Phe Lys Thr Ile Leu Glu Ser Pro Thr Asp Lys Lys Val Gly
                155                 160                 165 tgg aaa gtg ata ttt aac aat atg gtg aat caa aat tgg gga cca tac       584
Trp Lys Val Ile Phe Asn Asn Met Val Asn Gln Asn Trp Gly Pro Tyr
            170                 175                 180 gat cga gat tct tgg aac ccg gta tat ggc aat caa ctt ttc atg aag       632
Asp Arg Asp Ser Trp Asn Pro Val Tyr Gly Asn Gln Leu Phe Met Lys
```

-continued

```
                185                 190                 195
act aga aat ggt tct atg aaa gca gca gat aac ttc ctt gat cct aac      680
Thr Arg Asn Gly Ser Met Lys Ala Ala Asp Asn Phe Leu Asp Pro Asn
200                 205                 210 aaa gca agt tcc cta tta tct tca ggg ttt tca cca gac ttc gct aca      728
Lys Ala Ser Ser Leu Leu Ser Ser Gly Phe Ser Pro Asp Phe Ala Thr
215                 220                 225                 230 gtt att act atg gat aga aaa gca tcc aaa caa caa aca aat ata gat      776
Val Ile Thr Met Asp Arg Lys Ala Ser Lys Gln Gln Thr Asn Ile Asp
                235                 240                 245 gta ata tac gaa cga gtt cgt gat gat tac caa ttg cat tgg act tca      824
Val Ile Tyr Glu Arg Val Arg Asp Asp Tyr Gln Leu His Trp Thr Ser
        250                 255                 260 cca aat tgg aaa ggt acc aat act aaa gat aaa tgg aca gat cgt tct      872
Pro Asn Trp Lys Gly Thr Asn Thr Lys Asp Lys Trp Thr Asp Arg Ser
    265                 270                 275 tca gaa aga tat aaa atc gat tgg gaa aaa gaa gaa atg aca aat taa      920
Ser Glu Arg Tyr Lys Ile Asp Trp Glu Lys Glu Glu Met Thr Asn
280                 285                 290 tgtaanttat ttgtacatgt acaaataaat ataatttata actttagccg aagctggatc    980
cggctgctac naanccccaa ngnagctgan ttgnctgctg ccccccctgac natactagca  1040 naccccttgg gnccctaacg ggtctgnggg gttttttgctg aangngnact tttccgnnan   1100
tcnncccggn cccccccnggt gaaatccnaa ncccccnaacn gggngtgnta ncaantttan  1160
tggnncntna ntttnnaaaan cnnntaantt ngnaacccc nttttncnan ggcnaannnn    1220 nanccttna naaaaaancc nnnggggggg tttcnntnnn annnccnttn aangggcccc    1280 cnngggnaa nnntnggggn                                                  1300
```

<210> SEQ ID NO 8
<211> LENGTH: 293
<212> TYPE: PRT
<213> ORGANISM: Artificial sequence
<220> FEATURE:
<221> NAME/KEY: misc_feature
<222> LOCATION: (5)..(5)
<223> OTHER INFORMATION: The 'Xaa' at location 5 stands for Leu, or Phe.
<220> FEATURE:
<221> NAME/KEY: misc_feature
<222> LOCATION: (7)..(7)
<223> OTHER INFORMATION: The 'Xaa' at location 7 stands for Tyr, Trp,
      Cys, Ser, Leu, or Phe.
<220> FEATURE:
<223> OTHER INFORMATION: Synthetic Construct

<400> SEQUENCE: 8

```
Gln Ile Leu Ile Xaa Thr Xaa Ala Thr Gly Thr Thr Asp Ile Gly Ser
1               5                   10                  15

Asn Thr Thr Val Lys Thr Gly Asp Leu Val Thr Tyr Asp Lys Glu Asn
                20                  25                  30

Gly Met His Lys Lys Val Phe Tyr Ser Phe Ile Asp Asp Lys Asn His
            35                  40                  45

Asn Lys Lys Leu Leu Val Ile Arg Thr Lys Gly Thr Ile Ala Gly Gln
        50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110
```

```
Arg Ser Thr Leu Thr Tyr Gly Phe Asn Gly Asn Leu Thr Gly Asp Asp
    115                 120                 125

Thr Ser Lys Ile Gly Gly Leu Ile Gly Ala Gln Val Ser Leu Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
                180                 185                 190

Asn Gln Leu Phe Met Lys Thr Arg Asn Gly Ser Met Lys Ala Ala Asp
            195                 200                 205

Asn Phe Leu Asp Pro Asn Lys Ala Ser Ser Leu Leu Ser Ser Gly Phe
        210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Pro Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn
    290

<210> SEQ ID NO 9
<211> LENGTH: 1342
<212> TYPE: DNA
<213> ORGANISM: Artificial sequence
<220> FEATURE:
<223> OTHER INFORMATION: M113F-RL2 alpha hemolysin mutant
<220> FEATURE:
<221> NAME/KEY: CDS
<222> LOCATION: (39)..(920)
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
```

-continued

```
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1067)..(1067)
<223> OTHER INFORMATION: n is a, c, g, or t
<220> FEATURE:
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1097)..(1098)
<223> OTHER INFORMATION: n is a, c, g, or t
<220> FEATURE:
<221> NAME/KEY: misc_feature
<222> LOCATION: (1100)..(1100)
<223> OTHER INFORMATION: n is a, c, g, or t
<220> FEATURE:
<221> NAME/KEY: misc_feature
<222> LOCATION: (1103)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
```

```
<223> OTHER INFORMATION: n is a, c, g, or t
<220> FEATURE:
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1175)..(1176)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1182)..(1184)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1196)..(1196)
<223> OTHER INFORMATION: n is a, c, g, or t
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
```

```
<222> LOCATION: (1210)..(1210)
<223> OTHER INFORMATION: n is a, c, g, or t
<220> FEATURE:
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1217)..(1221)
<223> OTHER INFORMATION: n is a, c, g, or t
<220> FEATURE:
<221> NAME/KEY: misc_feature
<222> LOCATION: (1223)..(1223)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1241)..(1243)
<223> OTHER INFORMATION: n is a, c, g, or t
<220> FEATURE:
<221> NAME/KEY: misc_feature
<222> LOCATION: (1255)..(1256)
<223> OTHER INFORMATION: n is a, c, g, or t
<220> FEATURE:
<221> NAME/KEY: misc_feature
<222> LOCATION: (1258)..(1260)
<223> OTHER INFORMATION: n is a, c, g, or t
<220> FEATURE:
<221> NAME/KEY: misc_feature
<222> LOCATION: (1262)..(1264)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
<222> LOCATION: (1270)..(1270)
<223> OTHER INFORMATION: n is a, c, g, or t
<220> FEATURE:
<221> NAME/KEY: misc_feature
<222> LOCATION: (1273)..(1273)
<223> OTHER INFORMATION: n is a, c, g, or t
<220> FEATURE:
<221> NAME/KEY: misc_feature
<222> LOCATION: (1282)..(1283)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1291)..(1293)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t

<400> SEQUENCE: 9
gttctgttta actttaagaa gggagatata catatgag cag att ctg ata ttn acn    56
                                          Gln Ile Leu Ile Xaa Thr
```

|  |  |  |  |  |  |  |  |  |  |  |  |  |  |  |  |
|---|---|---|---|---|---|---|---|---|---|---|---|---|---|---|---|
|  |  |  |  |  |  |  | 1 |  |  |  | 5 |  |  |  |  |
| tnn | gcg | acc | ggt | act | aca | gat | att | gga | agc | aat | act | aca | gta | aaa | aca | 104 |
| Xaa | Ala | Thr | Gly | Thr | Thr | Asp | Ile | Gly | Ser | Asn | Thr | Thr | Val | Lys | Thr |  |
|  |  | 10 |  |  |  |  | 15 |  |  |  | 20 |  |  |  |  |  |
| ggt | gat | tta | gtc | act | tat | gat | aaa | gaa | aat | ggc | atg | cac | aaa | aaa | gta | 152 |
| Gly | Asp | Leu | Val | Thr | Tyr | Asp | Lys | Glu | Asn | Gly | Met | His | Lys | Lys | Val |  |
|  |  | 25 |  |  |  |  | 30 |  |  |  |  | 35 |  |  |  |  |
| ttt | tat | agt | ttt | atc | gat | gat | aaa | aat | cac | aat | aaa | aaa | ctg | cta | gtt | 200 |
| Phe | Tyr | Ser | Phe | Ile | Asp | Asp | Lys | Asn | His | Asn | Lys | Lys | Leu | Leu | Val |  |
|  | 40 |  |  |  |  | 45 |  |  |  |  | 50 |  |  |  |  |  |
| att | aga | aca | aaa | ggt | acc | att | gct | ggt | caa | tat | aga | gtt | tat | agc | gaa | 248 |
| Ile | Arg | Thr | Lys | Gly | Thr | Ile | Ala | Gly | Gln | Tyr | Arg | Val | Tyr | Ser | Glu |  |
| 55 |  |  |  |  | 60 |  |  |  |  | 65 |  |  |  |  | 70 |  |
| gaa | ggt | gct | aac | aaa | agt | ggt | tta | gcc | tgg | cct | tca | gcc | ttt | aag | gta | 296 |
| Glu | Gly | Ala | Asn | Lys | Ser | Gly | Leu | Ala | Trp | Pro | Ser | Ala | Phe | Lys | Val |  |
|  |  |  |  | 75 |  |  |  |  | 80 |  |  |  |  | 85 |  |  |
| cag | ttg | caa | cta | cct | gat | aat | gaa | gta | gct | caa | ata | tct | gat | tac | tat | 344 |
| Gln | Leu | Gln | Leu | Pro | Asp | Asn | Glu | Val | Ala | Gln | Ile | Ser | Asp | Tyr | Tyr |  |
|  |  |  | 90 |  |  |  |  | 95 |  |  |  |  | 100 |  |  |  |
| ccg | cgg | aat | tcg | att | gat | aca | aaa | gag | tat | ttc | agt | acg | tta | acg | tac | 392 |
| Pro | Arg | Asn | Ser | Ile | Asp | Thr | Lys | Glu | Tyr | Phe | Ser | Thr | Leu | Thr | Tyr |  |
|  |  | 105 |  |  |  |  | 110 |  |  |  |  | 115 |  |  |  |  |
| gga | ttc | aac | ggt | aac | ctt | act | ggt | gat | gat | act | agt | aaa | att | gga | ggc | 440 |
| Gly | Phe | Asn | Gly | Asn | Leu | Thr | Gly | Asp | Asp | Thr | Ser | Lys | Ile | Gly | Gly |  |
|  | 120 |  |  |  |  | 125 |  |  |  |  | 130 |  |  |  |  |  |
| ctt | att | ggg | gcc | cag | gtt | tcc | cta | ggt | cat | aca | ctt | aag | tat | gtt | caa | 488 |
| Leu | Ile | Gly | Ala | Gln | Val | Ser | Leu | Gly | His | Thr | Leu | Lys | Tyr | Val | Gln |  |
| 135 |  |  |  |  | 140 |  |  |  |  | 145 |  |  |  |  | 150 |  |
| cct | gat | ttc | aaa | aca | att | ctc | gag | agc | cca | act | gat | aaa | aaa | gta | ggc | 536 |
| Pro | Asp | Phe | Lys | Thr | Ile | Leu | Glu | Ser | Pro | Thr | Asp | Lys | Lys | Val | Gly |  |
|  |  |  |  | 155 |  |  |  |  | 160 |  |  |  |  | 165 |  |  |
| tgg | aaa | gtg | ata | ttt | aac | aat | atg | gtg | aat | caa | aat | tgg | gga | cca | tac | 584 |
| Trp | Lys | Val | Ile | Phe | Asn | Asn | Met | Val | Asn | Gln | Asn | Trp | Gly | Pro | Tyr |  |
|  |  |  | 170 |  |  |  |  | 175 |  |  |  |  | 180 |  |  |  |
| gat | cga | gat | tct | tgg | aac | ccg | gta | tat | ggc | aat | caa | ctt | ttc | atg | aag | 632 |
| Asp | Arg | Asp | Ser | Trp | Asn | Pro | Val | Tyr | Gly | Asn | Gln | Leu | Phe | Met | Lys |  |
|  |  | 185 |  |  |  |  | 190 |  |  |  |  | 195 |  |  |  |  |
| act | aga | aat | ggt | tct | atg | aaa | gca | gca | gat | aac | ttc | ctt | gat | cct | aac | 680 |
| Thr | Arg | Asn | Gly | Ser | Met | Lys | Ala | Ala | Asp | Asn | Phe | Leu | Asp | Pro | Asn |  |
|  | 200 |  |  |  |  | 205 |  |  |  |  | 210 |  |  |  |  |  |
| aaa | gca | agt | tcc | cta | tta | tct | tca | ggg | ttt | tca | cca | gac | ttc | gct | aca | 728 |
| Lys | Ala | Ser | Ser | Leu | Leu | Ser | Ser | Gly | Phe | Ser | Pro | Asp | Phe | Ala | Thr |  |
| 215 |  |  |  |  | 220 |  |  |  |  | 225 |  |  |  |  | 230 |  |
| gtt | att | act | atg | gat | aga | aaa | gca | tcc | aaa | caa | caa | aca | aat | ata | gat | 776 |
| Val | Ile | Thr | Met | Asp | Arg | Lys | Ala | Ser | Lys | Gln | Gln | Thr | Asn | Ile | Asp |  |
|  |  |  |  | 235 |  |  |  |  | 240 |  |  |  |  | 245 |  |  |
| gta | ata | tac | gaa | cga | gtt | cgt | gat | gat | tac | caa | ttg | cat | tgg | act | tca | 824 |
| Val | Ile | Tyr | Glu | Arg | Val | Arg | Asp | Asp | Tyr | Gln | Leu | His | Trp | Thr | Ser |  |
|  |  |  | 250 |  |  |  |  | 255 |  |  |  |  | 260 |  |  |  |
| cca | aat | tgg | aaa | ggt | acc | aat | act | aaa | gat | aaa | tgg | aca | gat | cgt | tct | 872 |
| Pro | Asn | Trp | Lys | Gly | Thr | Asn | Thr | Lys | Asp | Lys | Trp | Thr | Asp | Arg | Ser |  |
|  |  | 265 |  |  |  |  | 270 |  |  |  |  | 275 |  |  |  |  |
| tca | gaa | aga | tat | aaa | atc | gat | tgg | gaa | aaa | gaa | gaa | atg | aca | aat | taa | 920 |
| Ser | Glu | Arg | Tyr | Lys | Ile | Asp | Trp | Glu | Lys | Glu | Glu | Met | Thr | Asn |  |  |
|  | 280 |  |  |  |  | 285 |  |  |  |  | 290 |  |  |  |  |  |

| | |
|---|---|
| tgtaanttat ttgtacatgt acaaataaat ataatttata actttagccg aagctggatc | 980 |
| cggctgctac naancccnaa ngnagctgan ttgnctgctg cccccctgac natactagca | 1040 |
| naccccttgg gncccctaacg ggtctgnggg gttttttgctg aangngnact tttccgnnan | 1100 |

-continued

```
tcnncccggn cccccngggt gaaatccnaa ncccccnaacn ggngntgnta ncaantttan    1160
tggnncntna ntttnnaaan cnnntaantt ngnaanccccc nttttncnan ggcnaannnn    1220 nanccttttna naaaaaaancc nnngggggggg tttcnntnnn annnccnttn aangggcccc   1280
cnnggggnaa nnntnggggn agatataaaa tcgattggga aaaagaagaa atgacaaatt    1340
aa                                                                    1342
```

<210> SEQ ID NO 10
<211> LENGTH: 293
<212> TYPE: PRT
<213> ORGANISM: Artificial sequence
<220> FEATURE:
<221> NAME/KEY: misc_feature
<222> LOCATION: (5)..(5)
<223> OTHER INFORMATION: The 'Xaa' at location 5 stands for Leu, or Phe.
<220> FEATURE:
<221> NAME/KEY: misc_feature
<222> LOCATION: (7)..(7)
<223> OTHER INFORMATION: The 'Xaa' at location 7 stands for Tyr, Trp, Cys, Ser, Leu, or Phe.
<220> FEATURE:
<223> OTHER INFORMATION: Synthetic Construct

<400> SEQUENCE: 10

```
Gln Ile Leu Ile Xaa Thr Xaa Ala Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Phe Ser Thr Leu Thr Tyr Gly Phe Asn Gly Asn Leu Thr Gly Asp Asp
        115                 120                 125

Thr Ser Lys Ile Gly Gly Leu Ile Gly Ala Gln Val Ser Leu Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Pro Asn Trp Lys Gly Thr Asn Thr Lys Asp
```

-continued

```
                260                 265                 270
Lys Trp Thr Asp Arg Ser Ser Glu Arg Tyr Lys Ile Asp Trp Glu Lys
        275                 280                 285

Glu Glu Met Thr Asn
    290

<210> SEQ ID NO 11
<211> LENGTH: 1300
<212> TYPE: DNA
<213> ORGANISM: Artificial sequence
<220> FEATURE:
<223> OTHER INFORMATION: M113N-RL2 alpha hemolysin mutant
<220> FEATURE:
<221> NAME/KEY: CDS
<222> LOCATION: (39)..(920)
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (926)..(926)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (994)..(994)
<223> OTHER INFORMATION: n is a, c, g, or t
<220> FEATURE:
<221> NAME/KEY: misc_feature
<222> LOCATION: (998)..(998)
<223> OTHER INFORMATION: n is a, c, g, or t
<220> FEATURE:
<221> NAME/KEY: misc_feature
<222> LOCATION: (1001)..(1001)
<223> OTHER INFORMATION: n is a, c, g, or t
<220> FEATURE:
<221> NAME/KEY: misc_feature
<222> LOCATION: (1003)..(1003)
<223> OTHER INFORMATION: n is a, c, g, or t
<220> FEATURE:
<221> NAME/KEY: misc_feature
<222> LOCATION: (1010)..(1010)
<223> OTHER INFORMATION: n is a, c, g, or t
<220> FEATURE:
<221> NAME/KEY: misc_feature
<222> LOCATION: (1014)..(1014)
<223> OTHER INFORMATION: n is a, c, g, or t
<220> FEATURE:
<221> NAME/KEY: misc_feature
<222> LOCATION: (1031)..(1031)
<223> OTHER INFORMATION: n is a, c, g, or t
<220> FEATURE:
<221> NAME/KEY: misc_feature
<222> LOCATION: (1041)..(1041)
<223> OTHER INFORMATION: n is a, c, g, or t
<220> FEATURE:
<221> NAME/KEY: misc_feature
<222> LOCATION: (1052)..(1052)
<223> OTHER INFORMATION: n is a, c, g, or t
<220> FEATURE:
<221> NAME/KEY: misc_feature
<222> LOCATION: (1067)..(1067)
<223> OTHER INFORMATION: n is a, c, g, or t
<220> FEATURE:
```

```
<221> NAME/KEY: misc_feature
<222> LOCATION: (1083)..(1083)
<223> OTHER INFORMATION: n is a, c, g, or t
<220> FEATURE:
<221> NAME/KEY: misc_feature
<222> LOCATION: (1085)..(1085)
<223> OTHER INFORMATION: n is a, c, g, or t
<220> FEATURE:
<221> NAME/KEY: misc_feature
<222> LOCATION: (1087)..(1087)
<223> OTHER INFORMATION: n is a, c, g, or t
<220> FEATURE:
<221> NAME/KEY: misc_feature
<222> LOCATION: (1097)..(1098)
<223> OTHER INFORMATION: n is a, c, g, or t
<220> FEATURE:
<221> NAME/KEY: misc_feature
<222> LOCATION: (1100)..(1100)
<223> OTHER INFORMATION: n is a, c, g, or t
<220> FEATURE:
<221> NAME/KEY: misc_feature
<222> LOCATION: (1103)..(1104)
<223> OTHER INFORMATION: n is a, c, g, or t
<220> FEATURE:
<221> NAME/KEY: misc_feature
<222> LOCATION: (1110)..(1110)
<223> OTHER INFORMATION: n is a, c, g, or t
<220> FEATURE:
<221> NAME/KEY: misc_feature
<222> LOCATION: (1117)..(1117)
<223> OTHER INFORMATION: n is a, c, g, or t
<220> FEATURE:
<221> NAME/KEY: misc_feature
<222> LOCATION: (1128)..(1128)
<223> OTHER INFORMATION: n is a, c, g, or t
<220> FEATURE:
<221> NAME/KEY: misc_feature
<222> LOCATION: (1131)..(1131)
<223> OTHER INFORMATION: n is a, c, g, or t
<220> FEATURE:
<221> NAME/KEY: misc_feature
<222> LOCATION: (1136)..(1136)
<223> OTHER INFORMATION: n is a, c, g, or t
<220> FEATURE:
<221> NAME/KEY: misc_feature
<222> LOCATION: (1140)..(1140)
<223> OTHER INFORMATION: n is a, c, g, or t
<220> FEATURE:
<221> NAME/KEY: misc_feature
<222> LOCATION: (1143)..(1143)
<223> OTHER INFORMATION: n is a, c, g, or t
<220> FEATURE:
<221> NAME/KEY: misc_feature
<222> LOCATION: (1145)..(1145)
<223> OTHER INFORMATION: n is a, c, g, or t
<220> FEATURE:
<221> NAME/KEY: misc_feature
<222> LOCATION: (1148)..(1148)
<223> OTHER INFORMATION: n is a, c, g, or t
<220> FEATURE:
<221> NAME/KEY: misc_feature
<222> LOCATION: (1151)..(1151)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1164)..(1165)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
```

-continued

```
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1171)..(1171)
<223> OTHER INFORMATION: n is a, c, g, or t
<220> FEATURE:
<221> NAME/KEY: misc_feature
<222> LOCATION: (1175)..(1176)
<223> OTHER INFORMATION: n is a, c, g, or t
<220> FEATURE:
<221> NAME/KEY: misc_feature
<222> LOCATION: (1180)..(1180)
<223> OTHER INFORMATION: n is a, c, g, or t
<220> FEATURE:
<221> NAME/KEY: misc_feature
<222> LOCATION: (1182)..(1184)
<223> OTHER INFORMATION: n is a, c, g, or t
<220> FEATURE:
<221> NAME/KEY: misc_feature
<222> LOCATION: (1188)..(1188)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1196)..(1196)
<223> OTHER INFORMATION: n is a, c, g, or t
<220> FEATURE:
<221> NAME/KEY: misc_feature
<222> LOCATION: (1201)..(1201)
<223> OTHER INFORMATION: n is a, c, g, or t
<220> FEATURE:
<221> NAME/KEY: misc_feature
<222> LOCATION: (1206)..(1206)
<223> OTHER INFORMATION: n is a, c, g, or t
<220> FEATURE:
<221> NAME/KEY: misc_feature
<222> LOCATION: (1208)..(1208)
<223> OTHER INFORMATION: n is a, c, g, or t
<220> FEATURE:
<221> NAME/KEY: misc_feature
<222> LOCATION: (1210)..(1210)
<223> OTHER INFORMATION: n is a, c, g, or t
<220> FEATURE:
<221> NAME/KEY: misc_feature
<222> LOCATION: (1214)..(1214)
<223> OTHER INFORMATION: n is a, c, g, or t
<220> FEATURE:
<221> NAME/KEY: misc_feature
<222> LOCATION: (1217)..(1221)
<223> OTHER INFORMATION: n is a, c, g, or t
<220> FEATURE:
<221> NAME/KEY: misc_feature
<222> LOCATION: (1223)..(1223)
<223> OTHER INFORMATION: n is a, c, g, or t
<220> FEATURE:
<221> NAME/KEY: misc_feature
<222> LOCATION: (1229)..(1229)
<223> OTHER INFORMATION: n is a, c, g, or t
<220> FEATURE:
<221> NAME/KEY: misc_feature
<222> LOCATION: (1231)..(1231)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1241)..(1243)
```

```
<223> OTHER INFORMATION: n is a, c, g, or t
<220> FEATURE:
<221> NAME/KEY: misc_feature
<222> LOCATION: (1255)..(1256)
<223> OTHER INFORMATION: n is a, c, g, or t
<220> FEATURE:
<221> NAME/KEY: misc_feature
<222> LOCATION: (1258)..(1260)
<223> OTHER INFORMATION: n is a, c, g, or t
<220> FEATURE:
<221> NAME/KEY: misc_feature
<222> LOCATION: (1262)..(1264)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
<222> LOCATION: (1270)..(1270)
<223> OTHER INFORMATION: n is a, c, g, or t
<220> FEATURE:
<221> NAME/KEY: misc_feature
<222> LOCATION: (1273)..(1273)
<223> OTHER INFORMATION: n is a, c, g, or t
<220> FEATURE:
<221> NAME/KEY: misc_feature
<222> LOCATION: (1282)..(1283)
<223> OTHER INFORMATION: n is a, c, g, or t
<220> FEATURE:
<221> NAME/KEY: misc_feature
<222> LOCATION: (1288)..(1288)
<223> OTHER INFORMATION: n is a, c, g, or t
<220> FEATURE:
<221> NAME/KEY: misc_feature
<222> LOCATION: (1291)..(1293)
<223> OTHER INFORMATION: n is a, c, g, or t
<220> FEATURE:
<221> NAME/KEY: misc_feature
<222> LOCATION: (1295)..(1295)
<223> OTHER INFORMATION: n is a, c, g, or t
<220> FEATURE:
<221> NAME/KEY: misc_feature
<222> LOCATION: (1300)..(1300)
<223> OTHER INFORMATION: n is a, c, g, or t

<400> SEQUENCE: 11
gttctgttta actttaagaa gggagatata catatgag cag att ctg ata ttn acn      56
                                         Gln Ile Leu Ile Xaa Thr
                                          1               5 tnn gcg acc ggt act aca gat att gga agc aat act aca gta aaa aca      104
Xaa Ala Thr Gly Thr Thr Asp Ile Gly Ser Asn Thr Thr Val Lys Thr
         10                  15                  20 ggt gat tta gtc act tat gat aaa gaa aat ggc atg cac aaa aaa gta      152
Gly Asp Leu Val Thr Tyr Asp Lys Glu Asn Gly Met His Lys Lys Val
     25                  30                  35 ttt tat agt ttt atc gat gat aaa aat cac aat aaa aaa ctg cta gtt      200
Phe Tyr Ser Phe Ile Asp Asp Lys Asn His Asn Lys Lys Leu Leu Val
 40                  45                  50 att aga aca aaa ggt acc att gct ggt caa tat aga gtt tat agc gaa      248
Ile Arg Thr Lys Gly Thr Ile Ala Gly Gln Tyr Arg Val Tyr Ser Glu
 55                  60                  65                  70 gaa ggt gct aac aaa agt ggt tta gcc tgg cct tca gcc ttt aag gta      296
Glu Gly Ala Asn Lys Ser Gly Leu Ala Trp Pro Ser Ala Phe Lys Val
                 75                  80                  85 cag ttg caa cta cct gat aat gaa gta gct caa ata tct gat tac tat      344
Gln Leu Gln Leu Pro Asp Asn Glu Val Ala Gln Ile Ser Asp Tyr Tyr
             90                  95                 100 ccg cgg aat tcg att gat aca aaa gag tat aac agt acg tta acg tac      392
Pro Arg Asn Ser Ile Asp Thr Lys Glu Tyr Asn Ser Thr Leu Thr Tyr
         105                 110                 115
```

```
gga ttc aac ggt aac ctt act ggt gat gat act agt aaa att gga ggc    440
Gly Phe Asn Gly Asn Leu Thr Gly Asp Asp Thr Ser Lys Ile Gly Gly
    120                 125                 130 ctt att ggg gcc cag gtt tcc cta ggt cat aca ctt aag tat gtt caa    488
Leu Ile Gly Ala Gln Val Ser Leu Gly His Thr Leu Lys Tyr Val Gln
135                 140                 145                 150 cct gat ttc aaa aca att ctc gag agc cca act gat aaa aaa gta ggc    536
Pro Asp Phe Lys Thr Ile Leu Glu Ser Pro Thr Asp Lys Lys Val Gly
                155                 160                 165 tgg aaa gtg ata ttt aac aat atg gtg aat caa aat tgg gga cca tac    584
Trp Lys Val Ile Phe Asn Asn Met Val Asn Gln Asn Trp Gly Pro Tyr
            170                 175                 180 gat cga gat tct tgg aac ccg gta tat ggc aat caa ctt ttc atg aag    632
Asp Arg Asp Ser Trp Asn Pro Val Tyr Gly Asn Gln Leu Phe Met Lys
        185                 190                 195 act aga aat ggt tct atg aaa gca gca gat aac ttc ctt gat cct aac    680
Thr Arg Asn Gly Ser Met Lys Ala Ala Asp Asn Phe Leu Asp Pro Asn
    200                 205                 210 aaa gca agt tcc cta tta tct tca ggg ttt tca cca gac ttc gct aca    728
Lys Ala Ser Ser Leu Leu Ser Ser Gly Phe Ser Pro Asp Phe Ala Thr
215                 220                 225                 230 gtt att act atg gat aga aaa gca tcc aaa caa caa aca aat ata gat    776
Val Ile Thr Met Asp Arg Lys Ala Ser Lys Gln Gln Thr Asn Ile Asp
                235                 240                 245 gta ata tac gaa cga gtt cgt gat gat tac caa ttg cat tgg act tca    824
Val Ile Tyr Glu Arg Val Arg Asp Asp Tyr Gln Leu His Trp Thr Ser
            250                 255                 260 cca aat tgg aaa ggt acc aat act aaa gat aaa tgg aca gat cgt tct    872
Pro Asn Trp Lys Gly Thr Asn Thr Lys Asp Lys Trp Thr Asp Arg Ser
        265                 270                 275 tca gaa aga tat aaa atc gat tgg gaa aaa gaa gaa atg aca aat taa    920
Ser Glu Arg Tyr Lys Ile Asp Trp Glu Lys Glu Glu Met Thr Asn
    280                 285                 290 tgtaanttat ttgtacatgt acaaataaat ataatttata actttagccg aagctggatc    980
cggctgctac naanccnaa ngnagctgan ttgnctgctg cccccctgac natactagca   1040
naccccttgg gncctaacg ggtctgnggg gttttttgctg aangngnact tttccgnnan   1100
tcnncccggn cccccngggt gaaatccnaa ncccnaacn gngngtgnta ncaantttan   1160
tggnncntna ntttnnaaan cnnntaantt ngnaanccc nttttncnan ggcnaannnn    1220 nanccttna naaaaanncc nnnggggggg tttcnntnnn annnccnttn aangggcccc   1280
cnnggggnaa nnntngggggn                                             1300
```

<210> SEQ ID NO 12
<211> LENGTH: 293
<212> TYPE: PRT
<213> ORGANISM: Artificial sequence
<220> FEATURE:
<221> NAME/KEY: misc_feature
<222> LOCATION: (5)..(5)
<223> OTHER INFORMATION: The 'Xaa' at location 5 stands for Leu, or Phe.
<220> FEATURE:
<221> NAME/KEY: misc_feature
<222> LOCATION: (7)..(7)
<223> OTHER INFORMATION: The 'Xaa' at location 7 stands for Tyr, Trp,
      Cys, Ser, Leu, or Phe.
<220> FEATURE:
<223> OTHER INFORMATION: Synthetic Construct

<400> SEQUENCE: 12

Gln Ile Leu Ile Xaa Thr Xaa Ala Thr Gly Thr Thr Asp Ile Gly Ser

```
              1               5              10              15
            Asn Thr Thr Val Lys Thr Gly Asp Leu Val Thr Tyr Asp Lys Glu Asn
                             20                  25                  30

Gly Met His Lys Lys Val Phe Tyr Ser Phe Ile Asp Asp Lys Asn His
                     35                  40                  45

Asn Lys Lys Leu Leu Val Ile Arg Thr Lys Gly Thr Ile Ala Gly Gln
                     50                  55                  60

Tyr Arg Val Tyr Ser Glu Glu Gly Ala Asn Lys Ser Gly Leu Ala Trp
            65                  70                  75                  80

Pro Ser Ala Phe Lys Val Gln Leu Gln Leu Pro Asp Asn Glu Val Ala
                             85                  90                  95

Gln Ile Ser Asp Tyr Tyr Pro Arg Asn Ser Ile Asp Thr Lys Glu Tyr
                            100                 105                 110

Asn Ser Thr Leu Thr Tyr Gly Phe Asn Gly Asn Leu Thr Gly Asp Asp
                            115                 120                 125

Thr Ser Lys Ile Gly Gly Leu Ile Gly Ala Gln Val Ser Leu Gly His
                        130                 135                 140

Thr Leu Lys Tyr Val Gln Pro Asp Phe Lys Thr Ile Leu Glu Ser Pro
            145                 150                 155                 160

Thr Asp Lys Lys Val Gly Trp Lys Val Ile Phe Asn Asn Met Val Asn
                            165                 170                 175

Gln Asn Trp Gly Pro Tyr Asp Arg Asp Ser Trp Asn Pro Val Tyr Gly
                        180                 185                 190

Asn Gln Leu Phe Met Lys Thr Arg Asn Gly Ser Met Lys Ala Ala Asp
                        195                 200                 205

Asn Phe Leu Asp Pro Asn Lys Ala Ser Ser Leu Leu Ser Ser Gly Phe
                        210                 215                 220

Ser Pro Asp Phe Ala Thr Val Ile Thr Met Asp Arg Lys Ala Ser Lys
            225                 230                 235                 240

Gln Gln Thr Asn Ile Asp Val Ile Tyr Glu Arg Val Arg Asp Asp Tyr
                            245                 250                 255

Gln Leu His Trp Thr Ser Pro Asn Trp Lys Gly Thr Asn Thr Lys Asp
                        260                 265                 270

Lys Trp Thr Asp Arg Ser Ser Glu Arg Tyr Lys Ile Asp Trp Glu Lys
                        275                 280                 285

Glu Glu Met Thr Asn
                        290

<210> SEQ ID NO 13
<211> LENGTH: 1284
<212> TYPE: DNA
<213> ORGANISM: Artificial sequence
<220> FEATURE:
<223> OTHER INFORMATION: M113C-D8RL2 alpha hemolysin mutant
<220> FEATURE:
<221> NAME/KEY: CDS
<222> LOCATION: (39)..(944)
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t
<220> FEATURE:
```

-continued

```
<221> NAME/KEY: misc_feature
<222> LOCATION: (950)..(950)
<223> OTHER INFORMATION: n is a, c, g, or t
<220> FEATURE:
<221> NAME/KEY: misc_feature
<222> LOCATION: (1015)..(1015)
<223> OTHER INFORMATION: n is a, c, g, or t
<220> FEATURE:
<221> NAME/KEY: misc_feature
<222> LOCATION: (1018)..(1018)
<223> OTHER INFORMATION: n is a, c, g, or t
<220> FEATURE:
<221> NAME/KEY: misc_feature
<222> LOCATION: (1022)..(1022)
<223> OTHER INFORMATION: n is a, c, g, or t
<220> FEATURE:
<221> NAME/KEY: misc_feature
<222> LOCATION: (1025)..(1025)
<223> OTHER INFORMATION: n is a, c, g, or t
<220> FEATURE:
<221> NAME/KEY: misc_feature
<222> LOCATION: (1027)..(1027)
<223> OTHER INFORMATION: n is a, c, g, or t
<220> FEATURE:
<221> NAME/KEY: misc_feature
<222> LOCATION: (1034)..(1034)
<223> OTHER INFORMATION: n is a, c, g, or t
<220> FEATURE:
<221> NAME/KEY: misc_feature
<222> LOCATION: (1038)..(1038)
<223> OTHER INFORMATION: n is a, c, g, or t
<220> FEATURE:
<221> NAME/KEY: misc_feature
<222> LOCATION: (1055)..(1055)
<223> OTHER INFORMATION: n is a, c, g, or t
<220> FEATURE:
<221> NAME/KEY: misc_feature
<222> LOCATION: (1065)..(1065)
<223> OTHER INFORMATION: n is a, c, g, or t
<220> FEATURE:
<221> NAME/KEY: misc_feature
<222> LOCATION: (1076)..(1076)
<223> OTHER INFORMATION: n is a, c, g, or t
<220> FEATURE:
<221> NAME/KEY: misc_feature
<222> LOCATION: (1091)..(1091)
<223> OTHER INFORMATION: n is a, c, g, or t
<220> FEATURE:
<221> NAME/KEY: misc_feature
<222> LOCATION: (1107)..(1107)
<223> OTHER INFORMATION: n is a, c, g, or t
<220> FEATURE:
<221> NAME/KEY: misc_feature
<222> LOCATION: (1109)..(1109)
<223> OTHER INFORMATION: n is a, c, g, or t
<220> FEATURE:
<221> NAME/KEY: misc_feature
<222> LOCATION: (1111)..(1111)
<223> OTHER INFORMATION: n is a, c, g, or t
<220> FEATURE:
<221> NAME/KEY: misc_feature
<222> LOCATION: (1121)..(1122)
<223> OTHER INFORMATION: n is a, c, g, or t
<220> FEATURE:
<221> NAME/KEY: misc_feature
<222> LOCATION: (1124)..(1124)
<223> OTHER INFORMATION: n is a, c, g, or t
<220> FEATURE:
<221> NAME/KEY: misc_feature
<222> LOCATION: (1127)..(1128)
<223> OTHER INFORMATION: n is a, c, g, or t
<220> FEATURE:
<221> NAME/KEY: misc_feature
<222> LOCATION: (1134)..(1134)
<223> OTHER INFORMATION: n is a, c, g, or t
<220> FEATURE:
<221> NAME/KEY: misc_feature
<222> LOCATION: (1141)..(1141)
<223> OTHER INFORMATION: n is a, c, g, or t
```

```
-continued

<220> FEATURE:
<221> NAME/KEY: misc_feature
<222> LOCATION: (1152)..(1152)
<223> OTHER INFORMATION: n is a, c, g, or t
<220> FEATURE:
<221> NAME/KEY: misc_feature
<222> LOCATION: (1155)..(1155)
<223> OTHER INFORMATION: n is a, c, g, or t
<220> FEATURE:
<221> NAME/KEY: misc_feature
<222> LOCATION: (1160)..(1160)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1167)..(1167)
<223> OTHER INFORMATION: n is a, c, g, or t
<220> FEATURE:
<221> NAME/KEY: misc_feature
<222> LOCATION: (1169)..(1169)
<223> OTHER INFORMATION: n is a, c, g, or t
<220> FEATURE:
<221> NAME/KEY: misc_feature
<222> LOCATION: (1172)..(1172)
<223> OTHER INFORMATION: n is a, c, g, or t
<220> FEATURE:
<221> NAME/KEY: misc_feature
<222> LOCATION: (1175)..(1175)
<223> OTHER INFORMATION: n is a, c, g, or t
<220> FEATURE:
<221> NAME/KEY: misc_feature
<222> LOCATION: (1179)..(1179)
<223> OTHER INFORMATION: n is a, c, g, or t
<220> FEATURE:
<221> NAME/KEY: misc_feature
<222> LOCATION: (1184)..(1184)
<223> OTHER INFORMATION: n is a, c, g, or t
<220> FEATURE:
<221> NAME/KEY: misc_feature
<222> LOCATION: (1188)..(1189)
<223> OTHER INFORMATION: n is a, c, g, or t
<220> FEATURE:
<221> NAME/KEY: misc_feature
<222> LOCATION: (1191)..(1191)
<223> OTHER INFORMATION: n is a, c, g, or t
<220> FEATURE:
<221> NAME/KEY: misc_feature
<222> LOCATION: (1193)..(1193)
<223> OTHER INFORMATION: n is a, c, g, or t
<220> FEATURE:
<221> NAME/KEY: misc_feature
<222> LOCATION: (1195)..(1195)
<223> OTHER INFORMATION: n is a, c, g, or t
<220> FEATURE:
<221> NAME/KEY: misc_feature
<222> LOCATION: (1199)..(1200)
<223> OTHER INFORMATION: n is a, c, g, or t
<220> FEATURE:
<221> NAME/KEY: misc_feature
<222> LOCATION: (1204)..(1204)
<223> OTHER INFORMATION: n is a, c, g, or t
<220> FEATURE:
<221> NAME/KEY: misc_feature
<222> LOCATION: (1206)..(1208)
<223> OTHER INFORMATION: n is a, c, g, or t
<220> FEATURE:
<221> NAME/KEY: misc_feature
<222> LOCATION: (1212)..(1212)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1217)..(1217)
```

<223> OTHER INFORMATION: n is a, c, g, or t
<220> FEATURE:
<221> NAME/KEY: misc_feature
<222> LOCATION: (1220)..(1220)
<223> OTHER INFORMATION: n is a, c, g, or t
<220> FEATURE:
<221> NAME/KEY: misc_feature
<222> LOCATION: (1225)..(1225)
<223> OTHER INFORMATION: n is a, c, g, or t
<220> FEATURE:
<221> NAME/KEY: misc_feature
<222> LOCATION: (1230)..(1230)
<223> OTHER INFORMATION: n is a, c, g, or t
<220> FEATURE:
<221> NAME/KEY: misc_feature
<222> LOCATION: (1232)..(1232)
<223> OTHER INFORMATION: n is a, c, g, or t
<220> FEATURE:
<221> NAME/KEY: misc_feature
<222> LOCATION: (1234)..(1234)
<223> OTHER INFORMATION: n is a, c, g, or t
<220> FEATURE:
<221> NAME/KEY: misc_feature
<222> LOCATION: (1238)..(1238)
<223> OTHER INFORMATION: n is a, c, g, or t
<220> FEATURE:
<221> NAME/KEY: misc_feature
<222> LOCATION: (1241)..(1245)
<223> OTHER INFORMATION: n is a, c, g, or t
<220> FEATURE:
<221> NAME/KEY: misc_feature
<222> LOCATION: (1247)..(1247)
<223> OTHER INFORMATION: n is a, c, g, or t
<220> FEATURE:
<221> NAME/KEY: misc_feature
<222> LOCATION: (1253)..(1253)
<223> OTHER INFORMATION: n is a, c, g, or t
<220> FEATURE:
<221> NAME/KEY: misc_feature
<222> LOCATION: (1255)..(1255)
<223> OTHER INFORMATION: n is a, c, g, or t
<220> FEATURE:
<221> NAME/KEY: misc_feature
<222> LOCATION: (1262)..(1262)
<223> OTHER INFORMATION: n is a, c, g, or t
<220> FEATURE:
<221> NAME/KEY: misc_feature
<222> LOCATION: (1265)..(1267)
<223> OTHER INFORMATION: n is a, c, g, or t
<220> FEATURE:
<221> NAME/KEY: misc_feature
<222> LOCATION: (1279)..(1280)
<223> OTHER INFORMATION: n is a, c, g, or t
<220> FEATURE:
<221> NAME/KEY: misc_feature
<222> LOCATION: (1282)..(1284)
<223> OTHER INFORMATION: n is a, c, g, or t

<400> SEQUENCE: 13

```
gttctgttta actttaagaa gggagatata catatgag cag att ctg ata ttn acn         56
                                         Gln Ile Leu Ile Xaa Thr
                                         1               5 tnn gcg acc ggt act aca gat att gga agc aat act aca gta aaa aca         104
Xaa Ala Thr Gly Thr Thr Asp Ile Gly Ser Asn Thr Thr Val Lys Thr
        10                  15                  20 ggt gat tta gtc act tat gat aaa gaa aat ggc atg cac aaa aaa gta        152
Gly Asp Leu Val Thr Tyr Asp Lys Glu Asn Gly Met His Lys Lys Val
    25                  30                  35 ttt tat agt ttt atc gat gat aaa aat cac aat aaa aaa ctg cta gtt        200
Phe Tyr Ser Phe Ile Asp Asp Lys Asn His Asn Lys Lys Leu Leu Val
40                  45                  50 att aga aca aaa ggt acc att gct ggt caa tat aga gtt tat agc gaa        248
Ile Arg Thr Lys Gly Thr Ile Ala Gly Gln Tyr Arg Val Tyr Ser Glu
55                  60                  65                  70
```

| | | | | | | | | | | | | | | |
|---|---|---|---|---|---|---|---|---|---|---|---|---|---|---|
| gaa | ggt | gct | aac | aaa | agt | ggt | tta | gcc | tgg | cct | tca | gcc | ttt | aag | gta | 296 |
| Glu | Gly | Ala | Asn | Lys | Ser | Gly | Leu | Ala | Trp | Pro | Ser | Ala | Phe | Lys | Val |
| | | | | 75 | | | | | 80 | | | | | 85 | |

```
gaa ggt gct aac aaa agt ggt tta gcc tgg cct tca gcc ttt aag gta      296
Glu Gly Ala Asn Lys Ser Gly Leu Ala Trp Pro Ser Ala Phe Lys Val
                75                  80                  85 cag ttg caa cta cct gat aat gaa gta gct caa ata tct gat tac tat      344
Gln Leu Gln Leu Pro Asp Asn Glu Val Ala Gln Ile Ser Asp Tyr Tyr
            90                  95                 100 ccg cgg aat tcg att gat aca aaa gag tat tgc agt acg tta acg tac      392
Pro Arg Asn Ser Ile Asp Thr Lys Glu Tyr Cys Ser Thr Leu Thr Tyr
        105                 110                 115 gga ttc aac ggt aac ctt act ggt gat gat act agt aaa att gga ggc      440
Gly Phe Asn Gly Asn Leu Thr Gly Asp Asp Thr Ser Lys Ile Gly Gly
    120                 125                 130 ctt att ggg gcc cag gtt tcc cta ggt cat aca ctt aag tat gtt caa      488
Leu Ile Gly Ala Gln Val Ser Leu Gly His Thr Leu Lys Tyr Val Gln
135                 140                 145                 150 cct gat ttc aaa aca att ctc gag agc cca act gat aaa aaa gta ggc      536
Pro Asp Phe Lys Thr Ile Leu Glu Ser Pro Thr Asp Lys Lys Val Gly
                155                 160                 165 tgg aaa gtg ata ttt aac aat atg gtg aat caa aat tgg gga cca tac      584
Trp Lys Val Ile Phe Asn Asn Met Val Asn Gln Asn Trp Gly Pro Tyr
            170                 175                 180 gat cga gat tct tgg aac ccg gta tat ggc aat caa ctt ttc atg aag      632
Asp Arg Asp Ser Trp Asn Pro Val Tyr Gly Asn Gln Leu Phe Met Lys
        185                 190                 195 act aga aat ggt tct atg aaa gca gca gat aac ttc ctt gat cct aac      680
Thr Arg Asn Gly Ser Met Lys Ala Ala Asp Asn Phe Leu Asp Pro Asn
    200                 205                 210 aaa gca agt tcc cta tta tct tca ggg ttt tca cca gac ttc gct aca      728
Lys Ala Ser Ser Leu Leu Ser Ser Gly Phe Ser Pro Asp Phe Ala Thr
215                 220                 225                 230 gtt att act atg gat aga aaa gca tcc aaa caa caa aca aat ata gat      776
Val Ile Thr Met Asp Arg Lys Ala Ser Lys Gln Gln Thr Asn Ile Asp
                235                 240                 245 gta ata tac gaa cga gtt cgt gat gat tac caa ttg cat tgg act tca      824
Val Ile Tyr Glu Arg Val Arg Asp Asp Tyr Gln Leu His Trp Thr Ser
            250                 255                 260 cca aat tgg aaa ggt acc aat act aaa gat aaa tgg aca gat cgt tct      872
Pro Asn Trp Lys Gly Thr Asn Thr Lys Asp Lys Trp Thr Asp Arg Ser
        265                 270                 275 tca gaa aga tat aaa atc gat tgg gaa aaa gaa gaa atg aca aat gat      920
Ser Glu Arg Tyr Lys Ile Asp Trp Glu Lys Glu Glu Met Thr Asn Asp
    280                 285                 290 gac gat gat gac gac gat gat taa tgtaanttat ttgtacatgt acaaataaat    974
Asp Asp Asp Asp Asp Asp Asp
295                 300 ataatttata actttagccg aagctggatc cggctgctac naanccccnaa ngnagctgan 1034 ttgnctgctg ccccccctgac natactagca naccccttgg gncctaacg ggtctgnggg  1094 gtttttgctg aangngnact tttccgnnan tcnncccggn ccccccnggt gaaatccnaa  1154 ncccccnaacn gggngntgnta ncaantttan tggnncntna ntttnnaaaan cnnntaantt  1214 ngnaanccccc nttttncnan ggcnaannnn nanccctttna naaaaaancc nnnggggggg  1274 tttcnntnnn                                                         1284

<210> SEQ ID NO 14
<211> LENGTH: 301
<212> TYPE: PRT
<213> ORGANISM: Artificial sequence
<220> FEATURE:
```

```
<221> NAME/KEY: misc_feature
<222> LOCATION: (5)..(5)
<223> OTHER INFORMATION: The 'Xaa' at location 5 stands for Leu, or Phe.
<220> FEATURE:
<221> NAME/KEY: misc_feature
<222> LOCATION: (7)..(7)
<223> OTHER INFORMATION: The 'Xaa' at location 7 stands for Tyr, Trp,
      Cys, Ser, Leu, or Phe.
<220> FEATURE:
<223> OTHER INFORMATION: Synthetic Construct

<400> SEQUENCE: 14

Gln Ile Leu Ile Xaa Thr Xaa Ala Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65              70                  75                  80

Pro Ser Ala Phe Lys Val Gln Leu Gln Leu Pro Asp Asn Glu Val Ala
            85                  90                  95

Gln Ile Ser Asp Tyr Tyr Pro Arg Asn Ser Ile Asp Thr Lys Glu Tyr
            100                 105                 110

Cys Ser Thr Leu Thr Tyr Gly Phe Asn Gly Asn Leu Thr Gly Asp Asp
        115                 120                 125

Thr Ser Lys Ile Gly Gly Leu Ile Gly Ala Gln Val Ser Leu Gly His
    130                 135                 140

Thr Leu Lys Tyr Val Gln Pro Asp Phe Lys Thr Ile Leu Glu Ser Pro
145             150                 155                 160

Thr Asp Lys Lys Val Gly Trp Lys Val Ile Phe Asn Asn Met Val Asn
            165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225             230                 235                 240

Gln Gln Thr Asn Ile Asp Val Ile Tyr Glu Arg Val Arg Asp Asp Tyr
            245                 250                 255

Gln Leu His Trp Thr Ser Pro Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Asp Asp Asp Asp Asp Asp
        290                 295                 300

<210> SEQ ID NO 15
<211> LENGTH: 937
<212> TYPE: DNA
<213> ORGANISM: Artificial sequence
<220> FEATURE:
<223> OTHER INFORMATION: T117C-D8RL3 alpha hemolysin mutant
<220> FEATURE:
<221>

<222> LOCATION: (13)..(918)

<400> SEQUENCE: 15

| | | | | | | | | | | | | |
|---|---|---|---|---|---|---|---|---|---|---|---|---|
| gatatacata tg | gca | gat | tct | gat | att | aat | att | aaa | acc | ggt | act | aca | gat | 51 |
| | Ala | Asp | Ser | Asp | Ile | Asn | Ile | Lys | Thr | Gly | Thr | Thr | Asp |
| | 1 | | | | 5 | | | | | 10 | | | |

| att | gga | agc | aat | act | aca | gta | aaa | aca | ggt | gat | tta | gtc | act | tat | gat | 99 |
|---|---|---|---|---|---|---|---|---|---|---|---|---|---|---|---|---|
| Ile | Gly | Ser | Asn | Thr | Thr | Val | Lys | Thr | Gly | Asp | Leu | Val | Thr | Tyr | Asp |
| 15 | | | | | 20 | | | | | 25 | | | | | |

| aaa | gaa | aat | ggc | atg | cac | aaa | aaa | gta | ttt | tat | agt | ttt | atc | gat | gat | 147 |
| Lys | Glu | Asn | Gly | Met | His | Lys | Lys | Val | Phe | Tyr | Ser | Phe | Ile | Asp | Asp |
| 30 | | | | 35 | | | | | 40 | | | | | 45 | |

| aaa | aat | cac | aat | aaa | aaa | ctg | cta | gtt | att | aga | aca | aaa | ggt | acc | att | 195 |
| Lys | Asn | His | Asn | Lys | Lys | Leu | Leu | Val | Ile | Arg | Thr | Lys | Gly | Thr | Ile |
| | | | 50 | | | | | 55 | | | | | 60 | | |

| gct | ggt | caa | tat | aga | gtt | tat | agc | gaa | gaa | ggt | gct | aac | aaa | agt | ggt | 243 |
| Ala | Gly | Gln | Tyr | Arg | Val | Tyr | Ser | Glu | Glu | Gly | Ala | Asn | Lys | Ser | Gly |
| | 65 | | | | | 70 | | | | | 75 | | | | |

| tta | gcc | tgg | cct | tca | gcc | ttt | aag | gta | cag | ttg | caa | cta | cct | gat | aat | 291 |
| Leu | Ala | Trp | Pro | Ser | Ala | Phe | Lys | Val | Gln | Leu | Gln | Leu | Pro | Asp | Asn |
| 80 | | | | | 85 | | | | | 90 | | | | | |

| gaa | gta | gct | caa | ata | tct | gat | tac | tat | ccg | cgg | aat | tcg | att | gat | aca | 339 |
| Glu | Val | Ala | Gln | Ile | Ser | Asp | Tyr | Tyr | Pro | Arg | Asn | Ser | Ile | Asp | Thr |
| 95 | | | | | 100 | | | | | 105 | | | | | |

| aaa | gag | tat | atg | agt | acg | tta | tgc | tac | gga | ttc | aac | ggt | aat | gtt | act | 387 |
| Lys | Glu | Tyr | Met | Ser | Thr | Leu | Cys | Tyr | Gly | Phe | Asn | Gly | Asn | Val | Thr |
| 110 | | | | | 115 | | | | | 120 | | | | | 125 |

| ggt | gat | gat | aca | gga | aaa | att | gga | ggc | ctt | att | ggt | gca | aat | gtt | tcg | 435 |
| Gly | Asp | Asp | Thr | Gly | Lys | Ile | Gly | Gly | Leu | Ile | Gly | Ala | Asn | Val | Ser |
| | | | 130 | | | | | 135 | | | | | 140 | | |

| att | ggt | cat | aca | ctt | aag | tat | gtt | caa | cct | gat | ttc | aaa | aca | att | ctc | 483 |
| Ile | Gly | His | Thr | Leu | Lys | Tyr | Val | Gln | Pro | Asp | Phe | Lys | Thr | Ile | Leu |
| | | 145 | | | | | 150 | | | | | 155 | | | |

| gag | agc | cca | act | gat | aaa | aaa | gta | ggc | tgg | aaa | gtg | ata | ttt | aac | aat | 531 |
| Glu | Ser | Pro | Thr | Asp | Lys | Lys | Val | Gly | Trp | Lys | Val | Ile | Phe | Asn | Asn |
| | 160 | | | | | 165 | | | | | 170 | | | | |

| atg | gtg | aat | caa | aat | tgg | gga | cca | tac | gat | cga | gat | tct | tgg | aac | ccg | 579 |
| Met | Val | Asn | Gln | Asn | Trp | Gly | Pro | Tyr | Asp | Arg | Asp | Ser | Trp | Asn | Pro |
| 175 | | | | | 180 | | | | | 185 | | | | | |

| gta | tat | ggc | aat | caa | ctt | ttc | atg | aaa | act | aga | aat | ggt | tct | atg | aaa | 627 |
| Val | Tyr | Gly | Asn | Gln | Leu | Phe | Met | Lys | Thr | Arg | Asn | Gly | Ser | Met | Lys |
| 190 | | | | | 195 | | | | | 200 | | | | | 205 |

| gca | gca | gat | aac | ttc | ctt | gat | cct | aac | aaa | gca | agt | tct | cta | tta | tct | 675 |
| Ala | Ala | Asp | Asn | Phe | Leu | Asp | Pro | Asn | Lys | Ala | Ser | Ser | Leu | Leu | Ser |
| | | | 210 | | | | | 215 | | | | | 220 | | |

| tca | ggg | ttt | tca | cca | gac | ttc | gct | aca | gtt | att | act | atg | gat | aga | aaa | 723 |
| Ser | Gly | Phe | Ser | Pro | Asp | Phe | Ala | Thr | Val | Ile | Thr | Met | Asp | Arg | Lys |
| | | 225 | | | | | 230 | | | | | 235 | | | |

| gca | tcc | aaa | caa | caa | aca | aat | ata | gat | gta | ata | tac | gaa | cga | gtt | cgt | 771 |
| Ala | Ser | Lys | Gln | Gln | Thr | Asn | Ile | Asp | Val | Ile | Tyr | Glu | Arg | Val | Arg |
| | 240 | | | | | 245 | | | | | 250 | | | | |

| gat | gat | tac | caa | ttg | cat | tgg | act | tca | aca | aat | tgg | aaa | ggt | acc | aat | 819 |
| Asp | Asp | Tyr | Gln | Leu | His | Trp | Thr | Ser | Thr | Asn | Trp | Lys | Gly | Thr | Asn |
| 255 | | | | | 260 | | | | | 265 | | | | | |

| act | aaa | gat | aaa | tgg | aca | gat | cgt | tct | tca | gaa | aga | tat | aaa | atc | gat | 867 |
| Thr | Lys | Asp | Lys | Trp | Thr | Asp | Arg | Ser | Ser | Glu | Arg | Tyr | Lys | Ile | Asp |
| 270 | | | | 275 | | | | | 280 | | | | | 285 | |

| tgg | gaa | aaa | gaa | gaa | atg | aca | aat | gat | gac | gat | gat | gac | gac | gat | gat | 915 |
| Trp | Glu | Lys | Glu | Glu | Met | Thr | Asn | Asp | Asp | Asp | Asp | Asp | Asp | Asp | Asp |
| | 290 | | | | | 295 | | | | | 300 | | | | | tga taagcttgga tccggctgc                    937

<210> SEQ ID NO 16
<211> LENGTH: 301
<212> TYPE: PRT
<213> ORGANISM: Artificial sequence
<220> FEATURE:
<223> OTHER INFORMATION: Synthetic Construct

<400> SEQUENCE: 16

```
Ala Asp Ser Asp Ile Asn Ile Lys Thr Gly Thr Thr Asp Ile Gly Ser
1               5                   10                  15

Asn Thr Thr Val Lys Thr Gly Asp Leu Val Thr Tyr Asp Lys Glu Asn
            20                  25                  30

Gly Met His Lys Lys Val Phe Tyr Ser Phe Ile Asp Asp Lys Asn His
        35                  40                  45

Asn Lys Lys Leu Leu Val Ile Arg Thr Lys Gly Thr Ile Ala Gly Gln
    50                  55                  60

Tyr Arg Val Tyr Ser Glu Glu Gly Ala Asn Lys Ser Gly Leu Ala Trp
65                  70                  75                  80

Pro Ser Ala Phe Lys Val Gln Leu Gln Leu Pro Asp Asn Glu Val Ala
                85                  90                  95

Gln Ile Ser Asp Tyr Tyr Pro Arg Asn Ser Ile Asp Thr Lys Glu Tyr
            100                 105                 110

Met Ser Thr Leu Cys Tyr Gly Phe Asn Gly Asn Val Thr Gly Asp Asp
        115                 120                 125

Thr Gly Lys Ile Gly Gly Leu Ile Gly Ala Asn Val Ser Ile Gly His
    130                 135                 140

Thr Leu Lys Tyr Val Gln Pro Asp Phe Lys Thr Ile Leu Glu Ser Pro
145                 150                 155                 160

Thr Asp Lys Lys Val Gly Trp Lys Val Ile Phe Asn Asn Met Val Asn
                165                 170                 175

Gln Asn Trp Gly Pro Tyr Asp Arg Asp Ser Trp Asn Pro Val Tyr Gly
            180                 185                 190

Asn Gln Leu Phe Met Lys Thr Arg Asn Gly Ser Met Lys Ala Ala Asp
        195                 200                 205

Asn Phe Leu Asp Pro Asn Lys Ala Ser Ser Leu Leu Ser Ser Gly Phe
    210                 215                 220

Ser Pro Asp Phe Ala Thr Val Ile Thr Met Asp Arg Lys Ala Ser Lys
225                 230                 235                 240

Gln Gln Thr Asn Ile Asp Val Ile Tyr Glu Arg Val Arg Asp Asp Tyr
                245                 250                 255

Gln Leu His Trp Thr Ser Thr Asn Trp Lys Gly Thr Asn Thr Lys Asp
            260                 265                 270

Lys Trp Thr Asp Arg Ser Ser Glu Arg Tyr Lys Ile Asp Trp Glu Lys
        275                 280                 285

Glu Glu Met Thr Asn Asp Asp Asp Asp Asp Asp
    290                 295                 300
```

<210> SEQ ID NO 17
<211> LENGTH: 228
<212> TYPE: PRT
<213> ORGANISM: Artificial sequence
<220> FEATURE:
<223> OTHER INFORMATION: Lambda exonuclease

<400> SEQUENCE: 17

Ser His Met Thr Pro Asp Ile Ile Leu Gln Arg Thr Gly Ile Asp Val
1               5                   10                  15

Arg Ala Val Glu Gln Gly Asp Ala Trp His Lys Leu Arg Leu Gly
            20                  25                  30

Val Ile Thr Ala Ser Glu Val His Asn Val Ile Ala Lys Pro Arg Ser
        35                  40                  45

Gly Lys Lys Trp Pro Asp Met Lys Met Ser Tyr Phe His Thr Leu Leu
    50                  55                  60

Ala Glu Val Cys Thr Gly Val Ala Pro Glu Val Asn Ala Lys Ala Leu
65              70                  75                  80

Ala Trp Gly Lys Gln Tyr Glu Asn Asp Ala Arg Thr Leu Phe Glu Phe
                85                  90                  95

Thr Ser Gly Val Asn Val Thr Glu Ser Pro Ile Ile Tyr Arg Asp Glu
            100                 105                 110

Ser Met Arg Thr Ala Cys Ser Pro Asp Gly Leu Cys Ser Asp Gly Asn
        115                 120                 125

Gly Leu Glu Leu Lys Cys Pro Phe Thr Ser Arg Asp Phe Met Lys Phe
    130                 135                 140

Arg Leu Gly Gly Phe Glu Ala Ile Lys Ser Ala Tyr Met Ala Gln Val
145                 150                 155                 160

Gln Tyr Ser Met Trp Val Thr Arg Lys Asn Ala Trp Tyr Phe Ala Asn
                165                 170                 175

Tyr Asp Pro Arg Met Lys Arg Glu Gly Leu His Tyr Val Val Ile Glu
            180                 185                 190

Arg Asp Glu Lys Tyr Met Ala Ser Phe Asp Glu Ile Val Pro Glu Phe
            195                 200                 205

Ile Glu Lys Met Asp Glu Ala Leu Ala Glu Ile Gly Phe Val Phe Gly
        210                 215                 220

Glu Gln Trp Arg
225

<210> SEQ ID NO 18
<211> LENGTH: 906
<212> TYPE: DNA
<213> ORGANISM: Artificial sequence
<220> FEATURE:
<223> OTHER INFORMATION: a-HL-D8RL3

<400> SEQUENCE: 18
gcagattctg atattaatat taaaaccggt actacagata ttggaagcaa tactacagta     60
aaaacaggtg atttagtcac ttatgataaa gaaaatggca tgcacaaaaa agtattttat    120
agttttatcg atgataaaaa tcacaataaa aaactgctag ttattagaac aaaaggtacc    180
attgctggtc aatatagagt ttatagcgaa gaaggtgcta caaaagtggt ttagcctgg     240 ccttcagcct ttaaggtaca gttgcaacta cctgataatg aagtagctca aatatctgat    300
tactatccgc ggaattcgat tgatacaaaa gagtatatga gtacgttaac gtacggattc    360
aacggtaatg ttactggtga tgatacagga aaaattggag gccttattgg tgcaaatgtt    420
tcgattggtc atacacttaa gtatgttcaa cctgatttca aaacaattct cgagagccca    480
actgataaaa aagtaggctg aaagtgata tttaacaata tggtgaatca aaattgggga    540
ccatacgatc gagattcttg gaacccggta tatggcaatc aacttttcat gaaaactaga    600
aatggttcta tgaaagcagc agataacttc cttgatccta caaagcaag ttctctatta    660 tcttcagggt tttcaccaga cttcgctaca gttattacta tggatagaaa agcatccaaa    720

```
caacaaacaa atatagatgt aatatacgaa cgagttcgtg atgattacca attgcattgg         780
acttcaacaa attggaaagg taccaatact aaagataaat ggacagatcg ttcttcagaa         840
agatataaaa tcgattggga aaaagaagaa atgacaaatg atgacgatga tgacgacgat         900
gattga                                                                    906
```